United States Patent
Caravano et al.

(10) Patent No.: US 10,072,006 B2
(45) Date of Patent: Sep. 11, 2018

(54) HETEROCYCLIC COMPOUNDS AND THEIR USE IN PREVENTING OR TREATING BACTERIAL INFECTIONS

(71) Applicant: MUTABILIS, Paris (FR)

(72) Inventors: Audrey Caravano, Enghien les Bains (FR); Sophie Chasset, Nandy (FR); Francis Chevreuil, Chantilly (FR); Fabien Faivre, Drancy (FR); Nicolas Lecointe, Paris (FR); Benoit Ledoussal, Pommerit Jaudy (FR); Frédéric Le Strat, Combs la Ville (FR); Sébastien Richard, Paris (FR); Christophe Simon, Chevilly Larue (FR); Sophie Vomscheid, Paris (FR); Julie Brias, Paris (FR); Julien Barbion, Sannois (FR)

(73) Assignee: MUTABILIS, Paris (FR)

( * ) Notice: Subject to any disclaimer, the term of this patent is extended or adjusted under 35 U.S.C. 154(b) by 0 days.

(21) Appl. No.: 15/563,519

(22) PCT Filed: Mar. 30, 2016

(86) PCT No.: PCT/EP2016/056847
§ 371 (c)(1),
(2) Date: Sep. 29, 2017

(87) PCT Pub. No.: WO2016/156348
PCT Pub. Date: Oct. 6, 2016

(65) Prior Publication Data
US 2018/0086761 A1     Mar. 29, 2018

(30) Foreign Application Priority Data

Mar. 31, 2015 (EP) .................................... 15305473
Jan. 26, 2016 (EP) .................................... 16305073

(51) Int. Cl.
C07D 471/08      (2006.01)
A61K 31/529      (2006.01)
A61K 45/06       (2006.01)
A61K 31/546      (2006.01)

(52) U.S. Cl.
CPC .......... *C07D 471/08* (2013.01); *A61K 31/529* (2013.01); *A61K 31/546* (2013.01); *A61K 45/06* (2013.01); *A61K 2300/00* (2013.01)

(58) Field of Classification Search
CPC .................................................... C07D 471/08
See application file for complete search history.

(56) References Cited

FOREIGN PATENT DOCUMENTS

| WO | 2010/038115 A1 | 4/2010 |
| WO | 2013/150296 A1 | 10/2013 |
| WO | 2014/141132 A1 | 9/2014 |

OTHER PUBLICATIONS

International Search Report and Written Opinion for PCT/EP2016/056847 dated May 27, 2016.
Extended European Search Report for EP 15305473.9 dated Jun. 5, 2015.

*Primary Examiner* — Bruck Kifle
(74) *Attorney, Agent, or Firm* — Thompson Coburn LLP

(57) ABSTRACT

The present invention relates to heterocyclic compounds, their process of preparation, pharmaceutical compositions comprising these compounds and use thereof, optionally in combination with other antibacterial agents and/or beta-lactam compounds, for the prevention or treatment of bacterial infections. The present invention also relates to the use of these compounds as β-lactamase inhibitors and/or as antibacterial agents.

22 Claims, No Drawings

HETEROCYCLIC COMPOUNDS AND THEIR USE IN PREVENTING OR TREATING BACTERIAL INFECTIONS

CROSS-REFERENCE TO RELATED APPLICATIONS

This application is a U.S. National Phase application of PCT/EP2016/056847, filed on Mar. 30, 2016, claiming the benefit of European Application No. 15305473.9, filed on Mar. 31, 2015, and European Application No. 16305073.5, filed on Jan. 26, 2016, all of which are incorporated herein by reference in their entireties.

The present invention relates to heterocyclic compounds, their process of preparation, the pharmaceutical compositions comprising these compounds and use thereof, optionally in combination with other antibacterial agents and/or beta-lactams, for the prevention or treatment of bacterial infections. The present invention also relates to the use of these compounds as beta-lactamase inhibitors and/or antibacterial agent.

It has been described that there is a continuous evolution of antibacterial resistance which could lead to bacterial strains against which known antibacterial compounds are inefficient.

There is thus a need to provide novel compounds and composition that can overcome bacterial antibiotic resistance.

The objective of the present invention is to provide new heterocyclic compounds that can be used as antibacterial agent and/or beta-lactamase inhibitor.

An objective of the present invention is also to provide new heterocyclic compounds that can be used for the prevention or treatment of bacterial infections.

Another objective of the present invention is to provide such new compounds which can overcome bacterial antibiotic resistance.

An objective of the invention is also to provide composition comprising these new heterocyclic compounds, optionally in combination with one or more other antibacterial agent, for the prevention or treatment of bacterial infections and which can overcome bacterial antibiotic resistance.

Other objectives will appear throughout the following description of the invention.

The present invention relates to compound of formula (I)

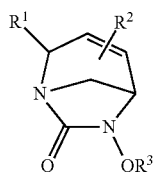

(I)

wherein $R^1$ represents a carbon-linked 4-, 5- or 6-membered heterocycle saturated, partially or totally unsaturated or aromatic comprising at least one nitrogen atom, —CN, —$(CH_2)_m$—$OQ^1$, —$(CH_2)_m$—$OC(O)Q^1$, —$C(O)OQ^1$, —$(CH_2)_m$—$OC(O)OQ^1$, —$(CH_2)_m$—$OC(O)NQ^1Q^2$, —$C(O)NHQ^1$, —$C(O)NHOQ^1$, —$(CH_2)_m$—$NHS(O)_2NQ^1Q^2$, —$C(O)NH$—$NHQ^1$, —$C(O)O$—$NHQ^1$, —$(CH_2)_m$—$NHC(O)Q^1$, —$(CH_2)_m$—$NHS(O)_2Q^1$, —$(CH_2)_m$—$NHC(O)OQ^1$, —$(CH_2)_m$—$NHC(O)NQ^1Q^2$, —$(CH_2)_m$—$NHQ^3$, —$(CH_2)_m$—NH—$C(NHQ^3)$=$NQ^4$, —$(CH_2)_m$—NH—CH=$NQ^3$, —$C(NHQ^3)$=$NQ^4$, wherein the heterocycle is optionally substituted by one or more $T^1$;

$R^2$ represents a 4- to 10-membered heterocycle saturated, partially or totally unsaturated or aromatic optionally substituted by one or more $T^2$;

$R^3$ represents —$SO_3H$, —CFHCOOH or —$CF_2COOH$;

$T^1$, identical or different independently represents a fluorine atom, a ($C_1$-$C_3$)-alkyl, a ($C_1$-$C_3$)-fluoroalkyl, O—($C_1$-$C_3$)fluoroalkyl, —$(CH_2)_n$-heterocycle wherein the heterocycle is a 4-, 5- or 6-membered heterocycle saturated, partially or totally unsaturated or aromatic comprising at least one nitrogen atom, —$(CH_2)_n OQ^1$, —$(CH_2)_n$—$C(O)ONHQ^1$, —$(CH_2)_n$—CN, —$(CH_2)_n$—$OC(O)Q^1$, —$(CH_2)_n$—$C(O)OQ^1$, —$(CH_2)_n$—$NHS(O)_2NQ^1Q^2$, —$(CH_2)_n$—$OC(O)OQ^1$, —$(CH_2)_n$—$OC(O)NHQ^1$, —$(CH_2)_n$—$C(O)NHQ^1$, —$(CH_2)_n$—$C(O)NHOQ^1$, —$(CH_2)_n$—$C(O)NH$—$NHQ^1$, —$(CH_2)_n$—$NHC(O)Q^1$, —$(CH_2)_n$—$NHS(O)_2Q^1$, —$(CH_2)_n$—$NHC(O)OQ^1$, —$(CH_2)_n$—$NHC(O)NQ^1Q^2$, —$(CH_2)_n$—$NHQ^1$, —$(CH_2)_n$—NH—$C(NHQ^3)$=$NQ^4$, —$(CH_2)_n$—NH—CH=$NQ^3$, $(CH_2)_n$—$C(NHQ^3)$=$NQ^4$, wherein the alkyl, fluoroalkyl, O-fluoroalkyl, and —$(CH_2)_n$-heterocycle are independently optionally substituted by one or more $T^3$;

$Q^1$ and $Q^2$, identical or different independently represent a hydrogen atom, ($C_1$-$C_3$)alkyl, —$(CH_2)_q$—$NHQ^3$, —$(CH_2)_q$—NH—$C(NHQ^3)$=$NQ^4$, $(CH_2)_q$—NH—CH=$NQ^3$, $(CH_2)_r$—$C(NHQ^3)$=$NQ^4$, —$(CH_2)_q$—$OQ^3$, —$(CH_2)_r$—$CONHQ^3$, —$(CH_2)_n$-heterocycle, wherein the heterocycle is a 4-, 5- or 6-membered heterocycle saturated, partially or totally unsaturated or aromatic comprising at least one nitrogen atom; wherein the alkyl and —$(CH_2)_n$-heterocycle are independently optionally substituted by one or more $T^3$; or $Q^1$ and $Q^2$ and the nitrogen atom to which they are bonded form together a saturated or partially unsaturated 4-, 5- or 6-membered heterocycle optionally substituted by one or more $T^3$;

$Q^3$ and $Q^4$, identical or different, independently represent a hydrogen atom or ($C_1$-$C_3$)alkyl;

$T^2$, identical or different, independently represents a fluorine atom, ($C_1$-$C_3$)alkyl, ($C_1$-$C_3$)fluoroalkyl, O—($C_1$-$C_3$)fluoroalkyl, —$(X)_p$—$(CH_2)_n$—($C_3$-$C_6$)cycloalkyl, —$(X)_p$—$(CH_2)_n$—($C_3$-$C_6$)cyclofluoroalkyl, —$(X)_p$—$(CH_2)_n$-heterocycle wherein the heterocycle is a 4-, 5- or 6-membered heterocycle, saturated, partially or totally unsaturated or aromatic, —$(X)_p(CH_2)_tOQ^5$, —$(X)_p$—$(CH_2)_u$—CN, —$(X)_p$—$(CH_2)_t$—$OC(O)Q^5$, —$(X)_p$—$(CH_2)_u$—$C(O)OQ^5$, —$(X)_p$—$(CH_2)_t$—$OC(O)OQ^5$, —$(X)_p$-$(CH_2)_t$—$OC(O)NQ^5Q^6$, —$(X)_p$—$(CH_2)_u$—$C(O)NQ^5Q^6$, —$(X)_p$—$(CH_2)_u$—$C(O)ONQ^5Q^6$, —$(X)_p$—$(CH_2)_u$—$C(O)NQ^5OQ^6$, —$(X)_p$—$(CH_2)_u$—$C(O)NQ^5$-$NQ^5Q^6$, —$(X)_p$—$(CH_2)_t$-$NQ^5C(O)Q^6$, —$(X)_p$—$(CH_2)_t$-$NQ^5S(O)_2NQ^5Q^6$, —$(X)_p$—$(CH_2)_t$-$NQ^5S(O)_2Q^6$, —$(X)_p$—$(CH_2)_t$-$NQ^5C(O)OQ^6$, —$(X)_p$—$(CH_2)_t$-$NQ^5C(O)NQ^5Q^6$, —$(X)_p$—$(CH_2)_t$-$NQ^5Q^6$, —$(X)_p$—$(CH_2)_t$—NH—$C(NHQ^3)$=$NQ^4$, —$(X)_p$—$(CH_2)_t$—NH—CH=$NQ^3$, —$(X)_p$—$(CH_2)_u$—$C(NHQ^3)$=$NQ^4$, wherein the alkyl, fluoroalkyl, O-fluoroalkyl, —$(X)_p$—$(CH_2)_n$-cycloalkyl, —$(X)_p$—$(CH_2)_n$-cyclofluoroalkyl, —$(X)_p$—$(CH_2)_n$-heterocycle are independently optionally substituted by one or more $T^3$;

$Q^5$ and $Q^6$, identical or different independently represent a hydrogen atom, ($C_1$-$C_3$)alkyl, —$(CH_2)_q$—$NHQ^3$, —$(CH_2)_q$—NH—$C(NHQ^3)$=$NQ^4$, $(CH_2)_q$—NH—CH=$NQ^3$, $(CH_2)_r$—$C(NHQ^3)$=$NQ^4$, —$(CH_2)_q$—$OQ^3$, —$(CH_2)_r$—$CONHQ^3$-$(CH_2)_n$-heterocycle, wherein the heterocycle is a 4-, 5- or 6-membered heterocycle saturated, partially or totally unsaturated or aromatic comprising at least one nitrogen atom; wherein the alkyl and —(CH$_2$)$_n$-heterocycle are independently optionally substituted by one or more T$^3$; or Q$^5$ and Q$^6$ and the nitrogen atom to which they are bonded form together a saturated or partially unsaturated 4-, 5- or 6-membered heterocycle optionally substituted by one or more T$^3$;

T$^3$, identical or different, independently represents —OH, —NH$_2$, —CONH$_2$;

m, identical or different, independently represents 1 or 2;

n, identical or different, independently represents 0, 1, 2 or 3;

t, identical or different, independently represents 0, 1, 2 or 3;

u, identical or different, independently represents 0, 1, 2 or 3;

q, identical or different, independently represents 2 or 3;

r, identical or different, independently represents 1, 2 or 3;

p, identical or different, independently represents 0 or 1 and when p is 0 t, identical or different is 0, 1, 2 or 3 and u, identical or different, is 0, 1, 2 or 3 and when p is 1 t, identical or different, independently represents 2 or 3 and u, identical or different, represents 1, 2 or 3;

X, identical or different, independently represents O, S, S(O), S(O)$_2$ or N(Q$^3$);

wherein
any carbon atom present within a group selected from alkyl; cycloalkyl; fluoroalkyl; cyclofluoroalkyl; heterocycle can be oxidized to form a C(O) group;
any sulphur atom present within an heterocycle can be oxidized to form a S(O) group or a S(O)$_2$ group;
any nitrogen atom present within a group wherein it is trisubstituted (thus forming a tertiary amine) or within an heterocycle can be further quaternized by a methyl group;

or their pharmaceutically acceptable salts, their corresponding zwitterion, or their optical isomers, racemates, diastereoisomers, enantiomers or tautomers.

Preferably, the compounds of formula (I) are chosen among compounds of formula (I*)

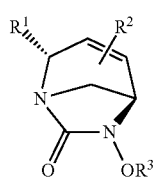

(I*)

wherein R$^1$, R$^2$ and R$^3$ are as defined for compounds of formula (I).

Preferably, the compounds of formula (I) are chosen among compounds of formula (A) or (B)

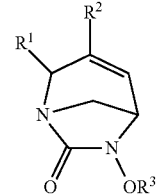

(A)

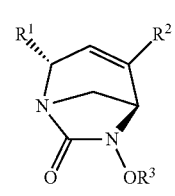

(B)

wherein R$^1$, R$^2$ and R$^3$ are as defined for compounds of formula (I).

Preferably, the compounds of formula (I) are chosen among compounds of formula (A*) or (B*)

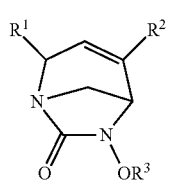

(A*)

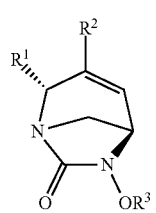

(B*)

wherein R$^1$, R$^2$ and R$^3$ are as defined for compounds of formula (I).

In one embodiment of the present invention, in the compounds of formula (I), (I*), (A), (A*), (B) and (B*), R$^1$ preferably represents a carbon-linked 4-, 5- or 6-membered heterocycle saturated, partially or totally unsaturated or aromatic comprising at least one nitrogen atom, —CN, —(CH$_2$)$_m$—OQ$^1$, —(CH$_2$)$_m$—OC(O)Q$^1$, —C(O)OQ$^1$, —(CH$_2$)$_m$—OC(O)OQ$^1$, —(CH$_2$)$_m$—OC(O)NQ$^1$Q$^2$, —C(O)NHQ$^1$, —(CH$_2$)$_m$—NHS(O)$_2$NQ$_1$Q$^2$, —C(O)NHOQ$^1$, —C(O)NH—NHQ$^1$, —C(O)O—NHQ$^1$, —(CH$_2$)$_m$—NHC(O)Q$^1$, —(CH$_2$)$_m$—NHS(O)$_2$Q$^1$, —(CH$_2$)$_m$—NHC(O)OQ$^1$, —(CH$_2$)$_m$—NHC(O)NQ$^1$Q$^2$, wherein the heterocycle is optionally substituted by one or more T$^1$, wherein m, Q$^1$, Q$^2$ and T$^1$ are as defined above. Preferably R$^1$ represents a carbon-linked 4-, 5- or 6-membered heterocycle saturated, partially or totally unsaturated or aromatic comprising at least one nitrogen atom, CN, —C(O)NHQ$^1$, —C(O)NHOQ$^1$, —C(O)NH—NHQ$^1$ or —(CH$_2$)$_m$OQ$^1$ wherein the heterocycle is optionally substituted by one or more T$^1$, wherein m, Q$^1$ and T$^1$ are as defined in the invention.

In another embodiment of the present invention, in the compounds of formula (I), (I*), (A), (A*), (B) and (B*), R$^1$ preferably represents —(CH$_2$)$_m$NHQ$^3$, —(CH$_2$)$_m$—NH—C(NHQ$^3$)=NQ$^4$, (CH$_2$)$_m$—NH—CH=NQ$^3$, —C(NHQ$^3$)=NQ$^4$, wherein m, Q$^3$ and Q$^4$ are as defined above. Preferably R$^1$ represents —(CH$_2$)$_m$NHQ$^3$, —(CH$_2$)$_m$—NH—C(NHQ$^3$)= NQ$^4$, wherein m, Q$^3$ and Q$^4$ are as defined in the invention, preferably Q$^3$ and Q$^4$ are H or methyl, preferably H, and m is preferably 1; preferably R$^1$ represents —(CH$_2$) NHQ$^3$; —(CH$_2$)NH—C(NHQ$^3$)=NQ$^4$, Q$^3$ and Q$^4$ are as defined in the invention, preferably Q$^3$ and Q$^4$ are H or methyl, preferably H.

In the compounds of formula (I), (I*), (A), (A*), (B) and (B*), $R^1$ preferably represents —CN, —C(O)OQ$^1$, —C(O)NHQ$^1$, —C(O)NHOQ$^1$, —C(O)NH—NHQ$^1$, —C(O)O—NHQ$^1$, preferably —CN; C(O)NHQ$^1$, —C(O)NHOQ$^1$, —C(O)NH—NHQ$^1$, wherein $Q^1$ is as defined in the invention.

In the compounds of formula (I), (I*), (A), (A*), (B) and (B*), $R^1$ preferably represents —(CH$_2$)$_m$—OQ$^1$, —(CH$_2$)$_m$—OC(O)Q$^1$, —(CH$_2$)$_m$—OC(O)OQ$^1$, —(CH$_2$)$_m$—OC(O)NQ$^1$Q$^2$, —(CH$_2$)$_m$—NHS(O)$_2$NQ$^1$Q$^2$, —(CH$_2$)$_m$—NHC(O)Q$^1$, —(CH$_2$)$_m$—NHS(O)$_2$Q$^1$, —(CH$_2$)$_m$—NHC(O)OQ$^1$, —(CH$_2$)$_m$—NHC(O)NQ$^1$Q$^2$, preferably —(CH$_2$)$_m$—OQ$^1$, —(CH$_2$)$_m$—OC(O)Q$^1$, —(CH$_2$)$_m$—NHS(O)$_2$NQ$^1$Q$^2$, —(CH$_2$)$_m$—NHC(O)Q$^1$, —(CH$_2$)$_m$—NHC(O)OQ$^1$ or —(CH$_2$)$_m$—NHC(O)NQ$^1$Q$^2$, more preferably —(CH$_2$)$_m$—OQ$^1$, —(CH$_2$)$_m$—NHC(O)Q$^1$, —(CH$_2$)$_m$—NHC(O)OQ$^1$, —(CH$_2$)$_m$—NHC(O)NQ$^1$Q$^2$ wherein $Q^1$ and $Q^2$ are as defined in the invention.

In the compounds of formula (I), (I*), (A), (A*), (B) and (B*), $R^1$ preferably represents a carbon-linked 4-, 5- or 6-membered heterocycle saturated, partially or totally unsaturated or aromatic comprising at least one nitrogen atom and optionally substituted by one or more $T^1$, it can comprise other heteroatoms, for example at least one further heteroatoms, for example 1, 2 or 3 further heteroatoms, the further heteroatom being preferably chosen among N, O, S, S(O) or S(O)$_2$. It is preferably a monocyclic heterocycle.

In the compounds of formula (I), (I*), (A), (A*), (B) and (B*), $R^1$ preferably represents —(CH$_2$)$_m$NHQ$^3$, —(CH$_2$)$_m$—NH—C(NHQ$^3$)=NQ$^4$, —CN, —C(O)NHQ$^1$, —C(O)NHOQ$^1$, —C(O)NH—NHQ$^1$, —(CH$_2$)$_m$—OQ$^1$, —(CH$_2$)$_m$—NHC(O)Q$^1$, —(CH$_2$)$_m$—NHC(O)OQ$^1$, —(CH$_2$)$_m$—NHC(O)NQ$^1$Q$^2$, a carbon-linked 4-, 5- or 6-membered heterocycle saturated, partially or totally unsaturated or aromatic comprising at least one nitrogen atom and optionally substituted by one or more $T^1$, it can comprise other heteroatoms, for example at least one further heteroatoms, for example 1, 2 or 3 further heteroatoms, the further heteroatom being preferably chosen among N, O, S, S(O) or S(O)$_2$, wherein $T^1$, m, $Q^1$ and $Q^2$ are as defined in the invention, and $Q^3$ and $Q^4$ are as defined in the invention, preferably $Q^3$ and $Q^4$ are H or methyl, preferably H.

In the compounds of formula (I), (I*), (A), (A*), (B) and (B*), $R^1$ preferably represents —(CH$_2$)$_m$NHQ$^3$, —(CH$_2$)$_m$—NH—C(NHQ$^3$)=NQ$^4$, —(CH$_2$)$_m$—OQ$^1$, —(CH$_2$)$_m$—NHC(O)NQ$^1$Q$^2$, —(CH$_2$)$_m$—NHC(O)OQ$^1$, —(CH$_2$)$_m$—NHC(O)NQ$^1$Q$^2$, (CH$_2$)$_m$—NHCOQ$^1$, a carbon-linked 4-, 5- or 6-membered heterocycle saturated, partially or totally unsaturated or aromatic comprising at least one nitrogen atom and optionally substituted by one or more $T^1$, it can comprise other heteroatoms, for example at least one further heteroatoms, for example 1, 2 or 3 further heteroatoms, the further heteroatom being preferably chosen among N, O, S, S(O) or S(O)$_2$, wherein $T^1$, m, $Q^1$ and $Q^2$ are as defined in the invention, and $Q^3$ and $Q^4$ are as defined in the invention, preferably $Q^3$ and $Q^4$ are H or methyl, preferably H.

In the compounds of formula (I), (I*), (A), (A*), (B) and (B*), $R^1$ preferably represents —(CH$_2$)$_m$NHQ$^3$, —(CH$_2$)$_m$—NH—C(NHQ$^3$)=NQ$^4$, —(CH$_2$)$_m$—OQ$^1$, —(CH$_2$)$_m$—NHC(O)NQ$^1$Q$^2$, —(CH$_2$)$_m$—NHC(O)OQ$^1$, —(CH$_2$)$_m$—NHC(O)NQ$^1$Q$^2$, a carbon-linked 4-, 5- or 6-membered heterocycle saturated, partially or totally unsaturated or aromatic comprising at least one nitrogen atom and optionally substituted by one or more $T^1$, it can comprise other heteroatoms, for example at least one further heteroatoms, for example 1, 2 or 3 further heteroatoms, the further heteroatom being preferably chosen among N, O, S, S(O) or S(O)$_2$, wherein $T^1$, m, $Q^1$ and $Q^2$ are as defined in the invention, and $Q^3$ and $Q^4$ are as defined in the invention, preferably $Q^3$ and $Q^4$ are H or methyl, preferably H.

According to another embodiment of the present invention, in the compounds of formula (I), (I*), (A), (A*), (B) and (B*), $R^1$ preferably represents a carbon-linked 4-, 5- or 6-membered heterocycle saturated, partially or totally unsaturated or aromatic comprising at least one nitrogen atom, —(CH$_2$)$_m$OC(O)Q$^1$, —C(O)OQ$^1$, —(CH$_2$)$_m$—NHS(O)$_2$NQ$^1$Q$^2$, —(CH$_2$)$_m$—OC(O)OQ$^1$, —C(O)NHOQ$^1$, —C(O)NH—NHQ$^1$, —C(O)O—NHQ$^1$, —(CH$_2$)$_m$—NHC(O)Q$^1$, —(CH$_2$)$_m$NHS(O)$_2$Q$_1$, —(CH$_2$)$_m$—NHC(O)OQ$^1$, —(CH$_2$)$_m$—NHC(O)NQ$^1$Q$^2$, —(CH$_2$)$_m$—NH—C(NHQ$^3$)=NQ$^4$, (CH$_2$)$_m$—NH—CH=NQ$^3$ or —C(NHQ$^3$)=NQ$^4$, wherein the heterocycle is optionally substituted by one or more $T^1$, wherein m, $Q^1$, $Q^2$, $Q^3$, $Q^4$ and $T^1$ are as defined above.

According to one embodiment of the present invention, in the compounds of formula (I), (I*), (A), (A*), (B) and (B*), $R^1$ preferably represents —(CH$_2$)$_m$—NH—C(NHQ$^3$)=NQ$^4$, (CH$_2$)$_m$—NH—CH=NQ$^3$, —C(NHQ$^3$)=NQ$^4$, wherein m, $Q^3$ and $Q^4$ are as defined above. Preferably $R^1$ represents —C(NHQ$^3$)=NQ$^4$, wherein m, $Q^3$ and $Q^4$ are as defined above.

According to a further embodiment of the present invention, in the compounds of formula (I), (I*), (A), (A*), (B) and (B*), $R^1$ preferably represents a carbon-linked 4-, 5- or 6-membered heterocycle saturated, partially or totally unsaturated or aromatic comprising at least one nitrogen atom, —(CH$_2$)$_m$OC(O)Q$^1$, —C(O)OQ$^1$, —(CH$_2$)$_m$—OC(O)OQ$^1$, —(CH$_2$)$_m$—NHS(O)$_2$NQ$^1$Q$^2$, —C(O)NHOQ$^1$, —C(O)NH—NHQ$^1$, —C(O)O—NHQ$^1$, —(CH$_2$)$_m$—NHC(O)Q$^1$, —(CH$_2$)$_m$NHS(O)$_2$Q$^1$, —(CH$_2$)$_m$—NHC(O)OQ$^1$, —(CH$_2$)$_m$—NHC(O)NQ$^1$Q$^2$ wherein the heterocycle is optionally substituted by one or more $T^1$ wherein m, $Q^1$, $Q^2$ and $T^1$ are as defined above. Preferably, $R^1$ represents a carbon-linked 4-, 5- or 6-membered heterocycle saturated, partially or totally unsaturated or aromatic comprising at least one nitrogen atom, —C(O)NHOQ$^1$ or —C(O)NH—NHQ$^1$, wherein the heterocycle is optionally substituted by one or more $T^1$, wherein m, $Q^1$ and $T^1$ are as defined above.

In the compounds of formula (I), (I*), (A), (A*), (B) and (B*) according to the invention, when $R^1$ is a carbon-linked 4-, 5- or 6-membered heterocycle saturated, partially or totally unsaturated or aromatic comprising at least one nitrogen atom and optionally substituted by one or more $T^1$, it can comprise other heteroatoms, for example at least one further heteroatoms, for example 1, 2 or 3 further heteroatoms, the further heteroatom being preferably chosen among N, O, S, S(O) or S(O)$_2$. It is preferably a monocyclic heterocycle.

Preferably, in the compounds of formula (I), (I*), (A), (A*), (B) and (B*) according to the invention, $R^1$ represents a carbon-linked 4-, 5- or 6-membered heterocycle saturated, partially or totally unsaturated or aromatic comprising at least one nitrogen atom, optionally substituted by one or more $T^1$; —C(O)NHQ$^1$, —(CH$_2$)$_m$—NH—C(NHQ$^3$)=NQ$^4$ or —(CH$_2$)$_m$NHQ$^3$, wherein $Q^1$, $Q^3$, $Q^4$, $T^1$ and m are as defined above.

In the compounds of formula (I), (I*), (A), (A*), (B) and (B*) according to the invention, preferably $R^2$ is a monocyclic or bicyclic 4- to 10-membered heterocycle, saturated, partially or totally unsaturated or aromatic, optionally substituted by one or more $T^2$. Preferably, this heterocycle comprises at least one nitrogen atom and can comprise further heteroatoms, for example at least one further heteroatoms, for example 1, 2 or 3 further heteroatoms, the further heteroatom being preferably chosen among N, O, S, S(O) or S(O)$_2$.

Preferably, R$^2$ is a monocyclic 4-, 5- or 6-membered heterocycle, saturated, partially or totally unsaturated or aromatic, optionally substituted by one or more T$^2$. Preferably, this heterocycle comprises at least one nitrogen atom and can comprise further heteroatoms, for example at least one further heteroatoms, for example 1, 2 or 3 further heteroatoms, the further heteroatom being preferably chosen among N, O, S, S(O) or S(O)$_2$. Preferably, the heterocycle is a carbon-linked heterocycle.

Preferably, in the compounds of formula (I), (I*), (A), (A*), (B) and (B*) according to the invention, R$^2$ represents a 4-, 5- or 6-membered heterocycle, saturated, partially or totally unsaturated or aromatic, comprising at least one nitrogen atom and optionally another heteroatom chosen among O, S, S(O), S(O)$_2$ or N, optionally substituted by one or more T$^2$.

Preferably, in the compounds of formula (I), (I*), (A), (A*), (B) and (B*) according to the invention, R$^3$ represent SO$_3$H or CF$_2$COOH.

Preferably, in the compounds of formula (I), (I*), (A), (A*), (B) and (B*), Q$^3$ and Q$^4$, identical or different independently represent H or methyl, preferably H.

Preferably, in the compounds of formula (I), (I*), (A), (A*), (B) and (B*), Q$^1$ and Q$^2$, identical or different independently represent H, methyl, —CH$_2$—CH$_2$—NH$_2$, —CH$_2$—CH$_2$—NH—CNH$_2$=NH, —CH$_2$—CH$_2$—NH—CH=NH, —CH$_2$—C(NH$_2$)=NH, CH$_2$—CH$_2$—OH, —CH$_2$—CONH$_2$, a —(CH$_2$)$_n$-heterocycle, wherein the heterocycle is a 4-, 5- or 6-membered heterocycle saturated, partially or totally unsaturated or aromatic comprising at least one nitrogen atom; wherein the heterocycle is independently optionally substituted by one or more T$^3$, wherein n and T$^3$ are as defined above.

Preferably, in the compounds of formula (I), (I*), (A), (A*), (B) and (B*), Q$^1$ and Q$^2$, identical or different independently represent H, methyl, —CH$_2$—CH$_2$—NH$_2$, —CH$_2$—CH$_2$—NH—CNH$_2$=NH, —CH$_2$—CH$_2$—NH—CH=NH, —CH$_2$—C(NH$_2$)=NH, CH$_2$—CH$_2$—OH, —CH$_2$—CONH$_2$, a saturated 4-membered heterocycle comprising one nitrogen atom, a saturated 5-membered heterocycle comprising one nitrogen atom, a saturated 6-membered heterocycle comprising one nitrogen atom; wherein the heterocycle is independently optionally substituted by one or more T$^3$, wherein n and T$^3$ are as defined above, preferably not substituted.

Preferably, in the compounds of formula (I), (I*), (A), (A*), (B) and (B*):
R$^2$ is a monocyclic or bicyclic 4- to 10-membered heterocycle, saturated, partially or totally unsaturated or aromatic, optionally substituted by one or more T$^2$; and
R$^1$ represents —(CH$_2$)$_m$NHQ$^3$, —(CH$_2$)$_m$—NH—C(NHQ$^3$)=NQ$^4$, (CH$_2$)$_m$—NH—CH=NQ$^3$, —C(NHQ$^3$)=NQ$^4$, wherein m, Q$^3$ and Q$^4$ are as defined above. Preferably R$^1$ represents —(CH$_2$)$_m$NHQ$^3$, —(CH$_2$)$_m$—NH—C(NHQ$^3$)=NQ$^4$, wherein m, Q$^3$ and Q$^4$ are as defined in the invention, preferably Q$^3$ and Q$^4$ are H or methyl, preferably H, and m is preferably 1; preferably R$^1$ represents —(CH$_2$)NHQ$^3$; —(CH$_2$)NH—C(NHQ$^3$)=NQ$^4$, Q$^3$ and Q$^4$ are as defined in the invention, preferably Q$^3$ and Q$^4$ are H or methyl, preferably H; or
R$^1$ preferably represents —CN, —C(O)OQ$^1$, —C(O)NHQ$^1$, —C(O)NHOQ$^1$, —C(O)NH—NHQ$^1$, —C(O)O—NHQ$^1$, preferably —CN; C(O)NHQ$^1$, —C(O)NHOQ$^1$, —C(O)NH—NHQ$^1$, wherein Q$^1$ is as defined in the invention; or
R$^1$ preferably represents —(CH$_2$)$_m$—OQ$^1$, —(CH$_2$)$_m$—OC(O)Q$^1$, —(CH$_2$)$_m$—OC(O)OQ$^1$, —(CH$_2$)$_m$—OC(O)NQ$^1$Q$^2$, —(CH$_2$)$_m$—NHS(O)$_2$NQ$^1$Q$^2$, —(CH$_2$)$_m$—NHC(O)Q$^1$, —(CH$_2$)$_m$—NHS(O)$_2$Q$^1$, —(CH$_2$)$_m$—NHC(O)OQ$^1$, —(CH$_2$)$_m$—NHC(O)NQ$^1$Q$^2$, preferably —(CH$_2$)$_m$—OQ$^1$, —(CH$_2$)$_m$—OC(O)Q$^1$, —(CH$_2$)$_m$—NHS(O)$_2$NQ$^1$Q$^2$, —(CH$_2$)$_m$—NHC(O)Q$^1$, —(CH$_2$)$_m$—NHC(O)OQ$^1$ or —(CH$_2$)$_m$—NHC(O)NQ$^1$Q$^2$, more preferably —(CH$_2$)$_m$—OQ$^1$, —(CH$_2$)$_m$—NHC(O)Q$^1$, —(CH$_2$)$_m$—NHC(O)OQ$^1$, —(CH$_2$)$_m$—NHC(O)NQ$^1$Q$^2$ wherein Q$^1$ and Q$^2$ are as defined in the invention; or
R$^1$ preferably represents a carbon-linked 4-, 5- or 6-membered heterocycle saturated, partially or totally unsaturated or aromatic comprising at least one nitrogen atom and optionally substituted by one or more T$^1$, it can comprise other heteroatoms, for example at least one further heteroatoms, for example 1, 2 or 3 further heteroatoms, the further heteroatom being preferably chosen among N, O, S, S(O) or S(O)$_2$. It is preferably a monocyclic heterocycle; or
R$^1$ preferably represents —(CH$_2$)$_m$NHQ$^3$, —(CH$_2$)$_m$—NH—C(NHQ$^3$)=NQ$^4$, —(CH$_2$)$_m$—OQ$^1$, —(CH$_2$)$_m$—NHC(O)Q$^1$, —(CH$_2$)$_m$—NHC(O)OQ$^1$, —(CH$_2$)$_m$—NHC(O)NQ$^1$Q$^2$, a carbon-linked 4-, 5- or 6-membered heterocycle saturated, partially or totally unsaturated or aromatic comprising at least one nitrogen atom and optionally substituted by one or more T$^1$, it can comprise other heteroatoms, for example at least one further heteroatoms, for example 1, 2 or 3 further heteroatoms, the further heteroatom being preferably chosen among N, O, S, S(O) or S(O)$_2$, wherein T$^1$, m, Q$^1$ and Q$^2$ are as defined in the invention, and Q$^3$ and Q$^4$ are as defined in the invention, preferably Q$^3$ and Q$^4$ are H or methyl, preferably H.

Preferably, in the compounds of formula (I), (I*), (A), (A*), (B) and (B*):
R$^2$ is a monocyclic or bicyclic 4- to 10-membered heterocycle, saturated, partially or totally unsaturated or aromatic, optionally substituted by one or more T$^2$; and
R$^1$ represents —(CH$_2$)$_m$NHQ$^3$, —(CH$_2$)$_m$—NH—C(NHQ$^3$)=NQ$^4$, wherein m, is as defined in the invention, preferably m is 1 or
R$^1$ represents —CN; C(O)NHQ$^1$, —C(O)NHOQ$^1$, —C(O)NH—NHQ$^1$; or
R$^1$ represents —(CH$_2$)$_m$—OQ$^1$, —(CH$_2$)$_m$—OC(O)Q$^1$, —(CH$_2$)$_m$—NHS(O)$_2$NQ$^1$Q$^2$, —(CH$_2$)$_m$—NHC(O)Q$^1$, —(CH$_2$)$_m$—NHC(O)OQ$^1$ or —(CH$_2$)$_m$—NHC(O)NQ$^1$Q$^2$, more preferably —(CH$_2$)$_m$—OQ$^1$, —(CH$_2$)$_m$—NHC(O)Q$^1$, —(CH$_2$)$_m$—NHC(O)OQ$^1$, —(CH$_2$)$_m$—NHC(O)NQ$^1$Q$^2$; or
R$^1$ represents a carbon-linked 4-, 5- or 6-membered heterocycle saturated, partially or totally unsaturated or aromatic comprising at least one nitrogen atom and optionally substituted by one or more T$^1$, it can comprise other heteroatoms, for example at least one further heteroatoms, for example 1, 2 or 3 further heteroatoms, the further heteroatom being preferably chosen among N, O, S, S(O) or S(O)$_2$. It is preferably a monocyclic heterocycle; or
R$^1$ represents —(CH$_2$)$_m$NHQ$^3$, —(CH$_2$)$_m$—NH—C(NHQ$^3$)=NQ$^4$, —(CH$_2$)$_m$—OQ$^1$, —(CH$_2$)$_m$—NHC(O)Q$^1$, —(CH$_2$)$_m$—NHC(O)OQ$^1$, —(CH$_2$)$_m$—NHC(O)NQ$^1$Q$^2$, a carbon-linked 4-, 5- or 6-membered heterocycle saturated, partially or totally unsaturated or aromatic comprising at least one nitrogen atom and optionally substituted by one or more $T^1$, it can comprise other heteroatoms, for example at least one further heteroatoms, for example 1, 2 or 3 further heteroatoms, the further heteroatom being preferably chosen among N, O, S, S(O) or S(O)$_2$, wherein $T^1$, m, are as defined in the invention; and $Q^1$ and $Q^2$, identical or different independently represent H, methyl, —CH$_2$—CH$_2$—NH$_2$, —CH$_2$—CH$_2$—NH—CNH$_2$=NH, —CH$_2$—CH$_2$—NH—CH=NH, —CH$_2$—C(NH$_2$)=NH, CH$_2$—CH$_2$—OH, —CH$_2$—CONH$_2$, a —(CH$_2$)$_n$-heterocycle, wherein the heterocycle is a 4-, 5- or 6-membered heterocycle saturated, partially or totally unsaturated or aromatic comprising at least one nitrogen atom; wherein the heterocycle is independently optionally substituted by one or more $T^3$, wherein n and $T^3$ are as defined above; and $Q^3$ and $Q^4$ represent H.

Preferably, in the compounds of formula (I), (I*), (A), (A*), (B) and (B*):

$R^2$ is a monocyclic or bicyclic 4- to 10-membered heterocycle, saturated, partially or totally unsaturated or aromatic, optionally substituted by one or more $T^2$; and $R^1$ represents —(CH$_2$)$_m$NHQ$^3$, —(CH$_2$)$_m$—NH—C(NHQ$^3$)=NQ$^4$, wherein m, is as defined in the invention, preferably m is 1, or $R^1$ represents —CN; C(O)NHQ$^1$, —C(O)NHOQ$^1$, —C(O)NH—NHQ$^1$; or $R^1$ represents —(CH$_2$)$_m$—OQ$^1$, —(CH$_2$)$_m$—OC(O)Q$^1$, —(CH$_2$)$_m$—NHS(O)$_2$NQ$^1$Q$^2$, —(CH$_2$)$_m$—NHC(O)Q$^1$, —(CH$_2$)$_m$—NHC(O)OQ$^1$ or —(CH$_2$)$_m$—NHC(O)NQ$^1$Q$^2$, more preferably —(CH$_2$)$_m$—OQ$^1$, —(CH$_2$)$_m$—NHC(O)Q$^1$, —(CH$_2$)$_m$—NHC(O)OQ$^1$; more preferably —(CH$_2$)$_m$—OQ$^1$, —(CH$_2$)$_m$—NHC(O)OQ$^1$; or $R^1$ represents a carbon-linked 4-, 5- or 6-membered heterocycle saturated, partially or totally unsaturated or aromatic comprising at least one nitrogen atom and optionally substituted by one or more $T^1$, it can comprise other heteroatoms, for example at least one further heteroatoms, for example 1, 2 or 3 further heteroatoms, the further heteroatom being preferably chosen among N, O, S, S(O) or S(O)$_2$. It is preferably a monocyclic heterocycle; or $R^1$ represents —(CH$_2$)$_m$NHQ$^3$, —(CH$_2$)$_m$—NH—C(NHQ$^3$)=NQ$^4$, —(CH$_2$)$_m$—OQ$^1$, —(CH$_2$)$_m$—NHC(O)Q$^1$, —(CH$_2$)$_m$—NHC(O)OQ$^1$, —(CH$_2$)$_m$—NHC(O)NQ$^1$Q$^2$, a carbon-linked 4-, 5- or 6-membered heterocycle saturated, partially or totally unsaturated or aromatic comprising at least one nitrogen atom and optionally substituted by one or more $T^1$, it can comprise other heteroatoms, for example at least one further heteroatoms, for example 1, 2 or 3 further heteroatoms, the further heteroatom being preferably chosen among N, O, S, S(O) or S(O)$_2$, wherein $T^1$, m, are as defined in the invention; and $Q^1$ and $Q^2$, identical or different independently represent H, methyl, —CH$_2$—CH$_2$—NH$_2$, —CH$_2$—CH$_2$—NH—CNH$_2$=NH, —CH$_2$—CH$_2$—NH—CH=NH, —CH$_2$—C(NH$_2$)=NH, CH$_2$—CH$_2$—OH, —CH$_2$—CONH$_2$, a —(CH$_2$)$_n$-heterocycle, wherein the heterocycle is a 4-, 5- or 6-membered heterocycle saturated, partially or totally unsaturated or aromatic comprising at least one nitrogen atom; wherein the heterocycle is independently optionally substituted by one or more $T^3$, wherein n and $T^3$ are as defined above; and $Q^3$ and $Q^4$ represent H; and $R^3$ represent SO$_3$H or CF$_2$COOH.

The invention relates also to compounds of formula

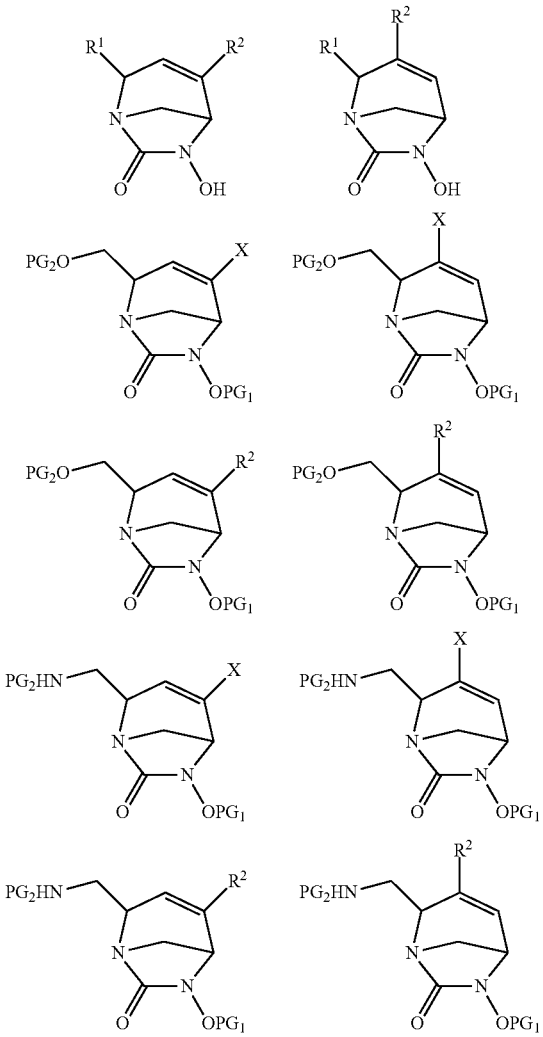

preferably of formula

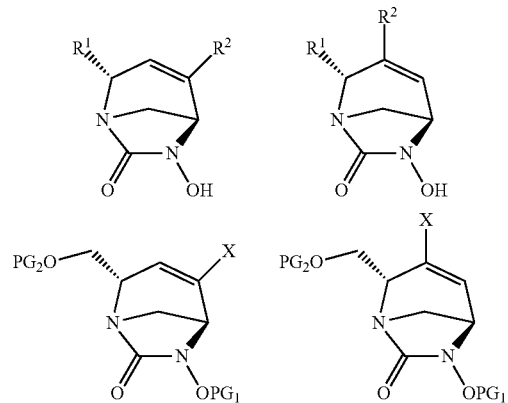

-continued

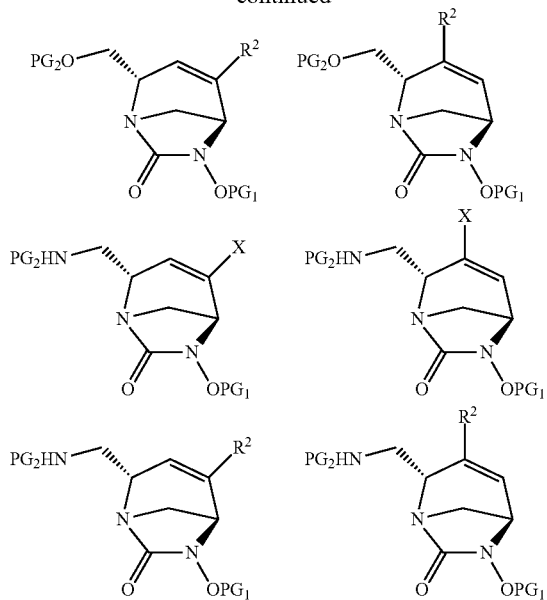

wherein

R¹ and R² are as defined above;

X is halogen, B(OR)₂; —OTf; —SnR₃ wherein R is alkyl or the OR are linked together with the B to form a cycle comprising for example 5 members;

PG₁ and PG₂, which are different, are protective groups, for example chosen among allyl, benzyl, tertbutyldimethylsilyl (TBDMS), tert-butoxycarbonyl (Boc), etc.

The compounds are especially intermediates compounds for the preparation of compounds of formula (I), (I*), (A), (A*), (B) or (B*) according to the invention.

The term "alkyl", as used herein, refers to an aliphatic-hydrocarbon group which may be straight or branched, having 1 to 3 carbon atoms in the chain unless specified otherwise. Preferred alkyl groups have 1 or 2 carbon atoms in the chain. Specific examples of alkyl groups include, but are not limited to, methyl, ethyl, n-propyl, iso propyl. Preferably, the alkyl group is methyl or ethyl.

The term "fluoroalkyl", as used herein, refers to an alkyl group substituted with at least one fluorine atom. The term "alkyl" is as defined above. Specific examples of fluoroalkyl groups include but are not limited to trifluoromethyl, difluoromethyl, fluoromethyl.

The term "cycloalkyl" refers to a saturated monocyclic or bicyclic non-aromatic hydrocarbon ring of 3 to 6 carbon atoms, preferably 3 to 4 carbon atoms, which can comprise one or more unsaturation. Specific examples of monocyclic cycloalkyl groups include cyclopropyl, cyclobutyl, cyclopentyl, cyclohexyl. Preferably, the cycloalkyl group is cyclopropyl or cyclobutyl.

The term "fluorocycloalkyl" refers to a cycloalkyl group substituted with at least one fluorine atom. The term "cycloalkyl" is as defined above. Specific examples of fluorocycloalkyl groups include fluorocyclopropyl, difluorocyclopropyl, fluorocyclobutyl, difluorocyclobutyl.

The term "heterocycle", as used herein and without contrary definition specifically mentioned, either alone or in combination with another radical, refers to a monocyclic or bicyclic saturated, partially or totally unsaturated or aromatic hydrocarbon radical, preferably 4 to 10-membered, comprising at least one heteroatom, such as N, O, S, S(O) or S(O)₂. Preferably, the heterocycle is a monocyclic saturated, partially or totally unsaturated or aromatic hydrocarbon radical, preferably 4, 5- or 6-membered, comprising at least one nitrogen atom and which can comprise at least one further heteroatom, such as N, O, S, S(O) or S(O)₂, the carbon atoms of the heterocycle can also be oxidized as C(O). Suitable heterocycles are also disclosed in the Handbook of Chemistry and Physics, 76th Edition, CRC Press, Inc., 1995-1996, pages 2 25 to 2-26. Examplary heterocycle groups include, but are not limited to, azetidinyl, oxetanyl, oxazolyl, oxazolidinyl, oxadiazolyl, pyrrolyl, pyrrolidinyl, pyridyl, tetrahydropyridinyl, piperidinyl, morpholinyl, pyrazolyl, pyrimidinyl, pyrazinyl, tetrazolyl, imidazolyl, thienyl, thiazolyl, furanyl, thiadiazolyl, isothiazolyl, triazolyl, tetrazolyl, pyrazolyl, isoxazolyl, 2-pyrrolidinonyl, imidazol-2,4-dione, 1,2,4-oxadiazolyl-5-one, 1,5-dihydropyrrolyl-2-one, pyrazinone, pyridazinone, pyridone, pyrimidone, dioxanyl, pyrrolidinyl, imidazolidinyl, pyranyl, tetrahydrofuranyl, dioxolanyl, tetrahydropyranyl. Preferably, in the compounds according to the invention, the heterocycle is linked to the structure of the compounds by a carbon atom of the heterocycle (also said carbon-linked heteroatom).

Moreover some compounds according to this invention may contain a basic amino group and thus may form an inner zwitterionic salt (or zwitterion) with the acidic group (R³)—OSO₃H, —OCFHCO₂H or —OCF₂CO₂H and such inner zwitterionic salts are also included in this invention.

The term "optionally substituted" means "non-substituted or substituted".

The term "racemate" is employed herein to refer to an equal amount of two specific enantiomers.

The term "enantiomer" is employed herein to refer to one of the two specific stereoisomers which is a non-superimposable mirror image with one other but is related to one other by reflection.

The compounds of the invention can possess one or more asymmetric carbon atoms and are thus capable of existing in the form of optical isomers as well as in the form of racemic or non-racemic mixtures thereof. The compounds of the invention can be used in the present invention as a single isomer or as a mixture of stereochemical isomeric forms. Diastereoisomers, i.e., nonsuperimposable stereochemical isomers can be separated by conventional means such as chromatography, distillation, crystallization or sublimation. The optical isomers (enantiomers) can be obtained by using optically active starting materials, by resolution of the racemic mixtures according to conventional processes, for example by formation of diastereoisomeric salts by treatment with an optically active acid or base or by using chiral chromatography column.

The expression "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the expression "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention can be synthesized from the parent compound which comprises a basic or an acidic moiety, by conventional chemical methods. Furthermore, the expression "pharmaceutically acceptable salt" refers to relatively non-toxic, inorganic and organic acid or base addition salts of the compounds of the present invention. These salts can be prepared in situ during the final isolation and purification of the compounds. In particular, the acid addition salts can be prepared by separately reacting the purified compound in its purified form with an organic or inorganic acid and by isolating the salt thus formed. Among the examples of acid addition salts are the hydrobromide, hydrochloride, hydroiodide, sulfamate, sulfate, bisulfate, phosphate, nitrate, acetate, propionate, succinate, oxalate, valerate, oleate, palmitate, stearate, laurate, borate, benzoate, lactate, tosylate, citrate, maleate, fumarate, tartrate, naphthylate, mesylate, glucoheptanate, glucoronate, glutamate, lactobionate, malonate, salicylate, methylenebis-b-hydroxynaphthoate, gentisic acid, isethionate, di-p-toluoyltartrate, ethanesulfonate, benzenesulfonate, cyclohexyl sulfamate, quinateslaurylsulfonate salts, and the like. Examples of base addition salts include ammonium salts such as tromethamine, meglumine, epolamine, etc, metal salts such as sodium, lithium, potassium, calcium, zinc or magnesium salts with organic bases such as dicyclohexylamine salts, N-methyl-D-glucamine. Lists of suitable salts may be found in Remington's Pharmaceutical Sciences, 17th ed., Mack Publishing Company, Easton, Pa., 1985, p. 1418, P. H. Stahl, C. G. Wermuth, Handbook of Pharmaceutical salts—Properties, Selection and Use, Wiley-VCH, 2002 and S. M. Berge et al. "Pharmaceutical Salts" J. Pharm. Sci, 66: p.1-19 (1977).

Compounds according to the invention also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described above and are not limited to $^{2}H$, $^{3}H$, $^{11}C$, $^{13}C$, $^{14}C$, $^{19}F$, $^{18}F$, $^{15}N$, $^{13}N$, $^{33}S$, $^{34}S$, $^{35}S$, $^{36}S$, $^{17}O$ or $^{18}O$. In one embodiment, isotopically-labeled compounds are useful in drug and/or substrate tissue distribution studies. In another embodiment, substitution with heavier isotopes such as deuterium ($^{2}H$) affords greater metabolic stability (for example increased in vivo half-life or reduced dosage requirements). Isotopically-labeled compounds are prepared by any suitable method or by processes using an appropriate isotopically-labeled reagent in place of the non-labeled reagent otherwise employed.

The present invention also relates to a composition, preferably a pharmaceutical composition, comprising at least one compound of formula (I), (I*), (A), (A*), (B) or (B*) as defined above, with a pharmaceutically acceptable excipient.

The composition according to the invention can further comprise at least one or more antibacterial agent(s), preferably at least one of these antibacterial agents is a beta-lactam.

The term "beta-lactam" or "β-lactam" refers to antibacterial compounds comprising a β-lactam unit, i.e. a group.

The term "pharmaceutically acceptable carrier" or "pharmaceutically acceptable excipient" is employed for any excipient, solvent, dispersion medium, absorption retardant, diluent or adjuvant etc., such as preserving or antioxidant agents, fillers, binders, disintegrating agents, wetting agents, emulsifying agents, suspending agents, solvents, dispersion media, coatings, antibacterial agents, isotonic and absorption delaying agents and the like, that does not produce a secondary reaction, for example an allergic reaction, in humans or animals.

Typical, non-limiting examples of excipients include mannitol, lactose, magnesium stearate, sodium saccharide, talcum, cellulose, sodium croscarmellose, glucose, gelatin, starch, lactose, dicalcium phosphate, sucrose, kaolin, magnesium carbonate, wetting agents, emulsifying agents, solubilizing agents, sterile water, saline, pH buffers, non-ionic surfactants, lubricants, stabilizing agents, binding agents and edible oils such as peanut oil, sesame oils and the like. In addition, various excipients commonly used in the art may be included. Pharmaceutically acceptable carriers or excipients are well known to a person skilled in the art, and include those described in Remington's Pharmaceutical Sciences (Mack Publishing Company, Easton, USA, 1985), Merck Index (Merck & Company, Rahway, N.J.), Gilman et al (Eds. The pharmacological basis of therapeutics, 8th Ed., pergamon press., 1990). Except insofar as any conventional media or adjuvant is incompatible with the active ingredient according to the invention, its use in the therapeutic compositions is contemplated.

The expression "antibacterial agent" as used herein, refers to any substance, compound or their combination capable of inhibiting, reducing or preventing growth of bacteria, inhibiting or reducing ability of bacteria to produce infection in a subject, or inhibiting or reducing ability of bacteria to multiply or remain infective in the environment, or decreasing infectivity or virulence of bacteria.

The antibacterial agent is selected among the following families: aminoglycosides, beta-lactams, glycylcyclines, tetracyclines, quinolones, fluoroquinolones, glycopeptides, lipopeptides, macrolides, ketolides, lincosamides, streptogramins, oxazolidinones and polymyxins alone or in mixture.

Preferably, the further antibacterial agent is selected among the beta-lactam families, and more preferably among penicillin, cephalosporins, penems, carbapenems and monobactam, alone or in mixture.

Among the penicillin the antibacterial agent is preferably selected in the group consisting of amoxicillin, ampicillin, azlocillin, mezocillin, apalcillin, hetacillin, bacampicillin, carbenicillin, sulbenicillin, temocillin, ticarcillin, piperacillin, mecillinam, pivmecillinam, methicillin, ciclacillin, talampacillin, aspoxicillin, oxacillin, cloxacillin, dicloxacillin, flucloxacillin, nafcillin, and pivampicillin, alone or in mixture.

Among the cephalosporin, the antibacterial agent is preferably selected in the group consisting of cefatriazine, cefazolin, cefoxitin, cephalexin, cephradine, ceftizoxime, cephacetrile, cefbuperazone, cefprozil, ceftobiprole, ceftobiprole medocaril, ceftaroline, ceftaroline fosaminyl, cefalonium, cefminox, ceforanide, cefotetan, ceftibuten, cefcapene pivoxil, cefditoren pivoxil, cefdaloxime cefroxadine, ceftolozane and S-649266, cephalothin, cephaloridine, cefaclor, cefadroxil, cefamandole, cefazolin, cephalexin, cephradine, ceftizoxime, cephacetrile, cefotiam, cefotaxime, cefsulodin, cefoperazone, cefmenoxime, cefmetazole, cephaloglycin, cefonicid, cefodizime, cefpirome, ceftazidime, ceftriaxone, cefpiramide, cefbuperazone, cefozopran, cefepime, cefoselis, cefluprenam, cefuzonam, cefpimizole, cefclidine, cefixime, ceftibuten, cefdinir, cefpodoxime axetil, cefpodoxime proxetil, cefteram pivoxil, cefetamet pivoxil, cefcapene pivoxil, cefditoren pivoxil, cefuroxime, cefuroxime axetil, loracarbef, and latamoxef, alone or in mixture.

Among the carbapenem, the antibacterial agent is preferably selected in the group consisting of imipenem, doripenem, meropenem, biapenem, ertapenem and panipenem, alone or in mixture.

Among the monobactam the antibacterial agent is preferably selected in the group consisting of aztreonam, tigemonam, carumonam, BAL30072 and nocardicin A, alone or in mixture.

Preferably, the invention relates to a pharmaceutical composition comprising
  a single compound of formula (I), (I*), (A), (A*), (B) and (B*);
  a compound of formula (I), (I*), (A), (A*), (B) and (B*) and one or more antibacterial compound;
  a compound of formula (I), (I*), (A), (A*), (B) and (B*) and one or more β-lactam compound;
  a compound of formula (I), (I*), (A), (A*), (B) and (B*), one or more antibacterial compound and one or more β-lactam compound.

The present invention also relates to a composition comprising at least a compound of formulae (I), (A), (B), (I*), (A*), (B*) according to the invention and ceftazidime.

The present invention also relates to a kit comprising:
  a pharmaceutical composition according to the invention, and
  at least one other composition comprising one or more antibacterial agent(s), preferably at least one of these antibacterial agent(s) is a beta-lactam.

The present invention also relates to a kit comprising:
  a pharmaceutical composition comprising at least a compound of formulae (I), (A), (B), (I*), (A*), (B*), (A1*), (A2*), (B1*) and (B2*) according to the invention; and
  a pharmaceutical composition comprising ceftazidime.

The two composition can be prepared separately each with one specific pharmaceutically acceptable carrier, and can be mix especially extemporaneity.

The present invention also refer to a compound of formula (I), (I*), (A), (A*), (B) or (B*) according to the invention for use as a medicine.

The present invention also refer to the use of a compound of formula (I), (I*), (A), (A*), (B) or (B*) according to the invention or of a composition according to the invention for the preparation of a medicine.

The present invention also provides the use of the compounds of formula (I), (I*), (A), (A*), (B) and (B*) on the control of bacteria. The compound according to the invention is usually used in combination with pharmaceutically acceptable excipient.

The present invention also refer to a compound of formula (I), (I*), (A), (A*), (B) or (B*) according to the invention for use as antibacterial agent.

The present invention also refer to the use of a compound of formula (I), (I*), (A), (A*), (B) or (B*) according to the invention or of a composition according to the invention for the preparation of an antibacterial agent medicine.

The present invention also refer to the use of a compound of formula (I), (I*), (A), (A*), (B) or (B*) according to the invention or of a composition according to the invention for the preparation of an inhibitor of beta-lactamase medicine.

The present invention also refer to the use of a compound of formula (I), (I*), (A), (A*), (B) or (B*) according to the invention or of a composition according to the invention for the preparation of an antibacterial agent and inhibitor of beta-lactamase medicine.

The present invention also refer to a compound of formula (I), (I*), (A), (A*), (B) or (B*) or a composition according to the invention or a kit according to the invention for use for the treatment or prevention of bacterial infections.

The present invention also refer to the use of a compound of formula (I), (I*), (A), (A*), (B) or (B*) or a composition according to the invention for the preparation of a medicine for the treatment or prevention of bacterial infections.

The terms "prevention", "prevent" and "preventing" as used herein are intended to mean the administration of a compound or composition according to the invention in order to prevent infection by bacteria or to prevent occurrence of related infection and/or diseases. The terms "prevention", "prevent" and "preventing" also encompass the administration of a compound or composition according to the present invention in order preventing at least one bacterial infection, by administration to a patient susceptible to be infected, or otherwise at a risk of infection by this bacteria.

The terms "treatment", "treat" and "treating" as used herein are intended to mean in particular the administration of a treatment comprising a compound or composition according to the present invention to a patient already suffering from an infection. The terms "treatment", "treat" and "treating" as used herein, also refer to administering a compound or composition according to the present invention, optionally with one or more antibacterial agent, in order to:
  reduce or eliminate either a bacterial infection or one or more symptoms associated with bacterial infection, or
  retard the progression of a bacterial infection or of one or more symptoms associated with bacterial infection, or
  reduce the severity of a bacterial infection or of one or more symptoms associated with the bacterial infection, or
  suppress the clinical manifestation of a bacterial infection, or
  suppress the manifestation of adverse symptoms of the bacterial infection.

The expression "infection" or "bacterial infection" as used herein, includes the presence of bacteria, in or on a subject, which, if its growth were inhibited, would result in a benefit to the subject. As such, the term "infection" or "bacterial infection" in addition to referring to the presence of bacteria also refers to normal flora, which is not desirable. The term "infection" includes infection caused by bacteria. Exemplary of such bacterial infection are urinary tract infection (UTI), kidney infections (pyelonephritis), gynecological and obstetrical infections, respiratory tract infection (RTI), acute exacerbation of chronic bronchitis (AECB), Community-acquired pneumonia (CAP), hospital-acquired pneumonia (HAP), ventilator associated pneumonia (VAP), intra-abdominal pneumonia (IAI), acute otitis media, acute sinusitis, sepsis, catheter-related sepsis, chancroid, chlamydia, skin infections, bacteremia.

The term "growth" as used herein, refers to the growth of one or more microorganisms and includes reproduction or population expansion of the microorganism, such as bacteria. The term also includes maintenance of on-going metabolic processes of a microorganism, including processes that keep the microorganism alive.

The bacteria are chosen amongst gram-positive bacteria or gram-negative bacteria, preferably the gram-negative bacteria.

The bacteria can be also chosen among bacteria producing "beta-lactamase" or "β-lactamase". These bacteria are well known by the skilled person.

The term "beta-lactamase" or "β-lactamase" as used herein, refers to any enzyme or protein or any other substance that is able to break down a beta-lactam ring. The term "beta-lactamase" or "β-lactamase" includes enzymes that are produced by bacteria and that have the ability to hydrolyze, either partially or completely, the beta-lactam ring present in a compound such as an antibacterial agent.

Among the gram-positive bacteria, the bacteria according to the invention is preferably chosen among *Staphylococcus, Streptococcus, Staphylococcus* species (including *Staphylococcus aureus, Staphylococcus epidermidis*), *Streptococcus* species (including *Streptococcus pneumonia, Streptococcus agalactiae*), *Enterococcus* species (including *Enterococcus faecalis* and *Enterococcus faecium*).

Among the gram-negative bacteria, the bacteria according to the invention is preferably chosen among *Acinetobacter* species (including *Acinetobacter baumannii*), *Citrobacter* species, *Escherichia* species (including *Escherichia coli*), *Haemophilus* influenza, *Morganella morganii, Klebsiella* species (including *Klebsiella pneumonia*), *Enterobacter* species (including *Enterobacter cloacae*), *Neisseria gonorrhoeae, Burkholderia* species (including *Burkholderia cepacia*), (*Proteus* species (including *Proteus mirabilis*), *Serratia* species (including *Serratia marcescens*), *Pseudomonas aeruginosa*.

The invention thus preferably refers to a compound of formula (I), (I*), (A), (A*), (B) or (B*), or a composition according to the invention or a kit according to the invention for use for the treatment or prevention of bacterial infection, preferably caused by bacteria producing one or more beta-lactamase(s). Preferably, the bacteria are chosen amongst gram-positive bacteria or gram-negative bacteria, preferably gram-negative bacteria.

The present invention also refer to the use of a compound of formula (I), (I*), (A), (A*), (B) or (B*) or a composition according to the invention for the preparation of a medicine for the treatment or prevention of bacterial infection, preferably caused by bacteria producing one or more beta-lactamase(s). Preferably, the bacteria are chosen amongst gram-positive bacteria or gram-negative bacteria, preferably gram-negative bacteria.

The present invention also refers to the kit as defined above, for a simultaneous, separated or sequential administration to a patient in need thereof for use for the treatment or prevention of bacterial infections, preferably caused by bacteria producing one or more beta-lactamase(s). Preferably, the bacteria are chosen amongst gram-positive bacteria or gram-negative bacteria, preferably gram-negative bacteria.

The present invention also refers to compound of formula (I), (I*), (A), (A*), (B) or (B*) for use in combination with one or more further antibacterial agent, preferably at least one of the further antibacterial agent is a beta lactam, for the treatment or prevention of bacterial infections, preferably caused by bacteria producing one or more beta-lactamase(s). Preferably, the bacteria are chosen amongst gram-positive bacteria or gram-negative bacteria, preferably gram-negative bacteria. Wherein the compounds of formula (I), (I*), (A), (A*), (B) or (B*) and the further antibacterial agent are administered simultaneously, separately or sequentially.

The present invention also refers to the use of a compound of formula (I), (I*), (A), (A*), (B) or (B*) or a composition according to the invention or a kit according to the invention for the prevention or treatment of bacterial infections, preferably of bacterial infection, preferably caused by bacteria producing one or more beta-lactamase(s). Preferably, the bacteria are chosen amongst gram-positive bacteria or gram-negative bacteria, preferably gram-negative bacteria.

The present invention also relates to a method for the treatment or prevention of bacterial infections, preferably caused by bacteria producing one or more beta-lactamase(s) comprising the administration of a therapeutically effective amount of compound of formula (I), (I*), (A), (A*), (B) or (B*), a composition according to the invention or a kit according to the invention to a patient in need thereof. Preferably, the bacteria are chosen amongst gram-positive bacteria or gram-negative bacteria, preferably gram-negative bacteria.

The term "patient" means a person or an animal at risk of being infected by bacteria or, a person or an animal being infected by bacteria, preferably by gram-positive and/or by gram-negative bacteria. As used herein, the term "patient" refers to a warm-blooded animal such as a mammal, preferably a human or a human child, who is afflicted with, or has the potential to be afflicted with one or more infections and conditions described herein. The identification of those subjects who are in need of treatment of herein-described diseases and conditions is well within the ability and knowledge of one skilled in the art. A veterinarian or a physician skilled in the art can readily identify, by the use of clinical tests, physical examination, medical/family history or biological and diagnostic tests, those subjects who are in need of such treatment.

The expression "therapeutically effective amount" or "pharmaceutically effective amount" as used herein, refer to an amount of a compound according to the invention, which when administered to a patient in need thereof, is sufficient to effect treatment for disease-states, conditions, or disorders for which the compound has utility. Such an amount would be sufficient to elicit the biological or medical response of a tissue system, or patient that is sought by a researcher or a clinician. The amount of a compound according to the invention which constitutes a "therapeutically effective amount" will vary, notably depending on the compound itself and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a "therapeutically effective amount" can be determined by one of ordinary skilled in the art having regard to its own knowledge, and this disclosure. Preferably, the compounds according to the invention are administered in an amount comprised between 0.1 to 30 g per day.

The compounds according to the invention may be provided in an aqueous physiological buffer solution for parenteral administration.

The compounds of the present invention are also capable of being administered in unit dose forms, wherein the expression "unit dose" means a single dose which is capable of being administered to a patient, and which can be readily handled and packaged, remaining as a physically and chemically stable unit dose comprising either the active compound itself, or as a pharmaceutically acceptable composition, as described hereinafter. Compounds provided herein can be formulated into pharmaceutical compositions by admixture with one or more pharmaceutically acceptable excipients. Such unit dose compositions may be prepared for use by oral administration, particularly in the form of tablets, simple capsules or soft gel capsules; or intranasally, particularly in the form of powders, nasal drops, or aerosols; or dermally, for example, topically in ointments, creams, lotions, gels or sprays, or via trans-dermal patches.

The compositions may conveniently be administered in unit dosage form and may be prepared by any of the methods well-known in the pharmaceutical art, for example, as described in *Remington: The Science and Practice of Pharmacy*, 20$^{th}$ ed.; Gennaro, A. R., Ed.; Lippincott Williams & Wilkins: Philadelphia, Pa., 2000.

Preferred formulations include pharmaceutical compositions in which a compound of the present invention is formulated for oral or parenteral administration.

For oral administration, tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolved, modified-release or sustained-release preparations and formulations, and wherein such sustained-release formulations are preferably bi-modal. Preferred tablets contain lactose, cornstarch, magnesium silicate, croscarmellose sodium, povidone, magnesium stearate, or talc in any combination.

Liquid preparations for parenteral administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, vegetable oils such as olive oil, and organic esters such as ethyl oleate. Aqueous carriers include mixtures of alcohols and water, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, and liposomes.

Alternative modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations. Formulations suitable for transdermal administration can be presented as discrete patches and can be lipophilic emulsions or buffered, aqueous solutions, dissolved and/or dispersed in a polymer or an adhesive.

The present invention also relates to process for the preparation of compounds of formula (I), (I*), (A), (A*), (B) and (B*) as defined above.

Preparation of the Compounds and Biological Activity:
Abbreviations or symbols used herein include:
ACHN: 1,1'-azobis(cyclohexanecarbonitrile)
ACN: acetonitrile
AcOH: acetic acid
Bn: benzyl
Boc: tert-butoxycarbonyl
Boc2O: tert-butoxycarbonyl anhydride
BocON: [2-(tert-butoxycarbonyloxyimino)-2-phenylacetonitrile]
Bromodan: 1,3-Dibromo-5,5-dimethylhydantoin
bs: broad singlet
Burgess reagent: methyl N-(triethylammoniosulfonyl)carbamate
CFU: colony-forming units
CLSI: clinical laboratory standards institute
d: doublet
DBU: 1,8-diazabicyclo[5.4.0]undec-7-ene
DCM: dichloromethane
dd: doublet of doublet
ddd: doublet of doublet
dq: doublet of quadruplet
dt: doublet of triplet
DTA: di-tert-butylazodicarboxylate
DEAD: diethyl azodicarboxylate
DIAD: diisopropyl azodicarboxylate
DIPEA: diisopropylethylamine
DMF: N,N-dimethylformamide
DMAP: 4-dimethylaminopyridine
DMSO: dimethylsulfoxide
EDCI: 1-ethyl-3-(3-dimethylaminopropyl)carbodiimide
EtOAc: ethyl acetate
Et$_2$O: diethyl ether
h: hours
HATU: 1-[Bis(dimethylamino)methylene]-1H-1,2,3-triazolo[4,5-b]pyridinium 3-oxid hexafluorophosphate
HOBt: N-hydroxybenzotriazole
IC$_{50}$: concentration of inhibitor responsible for 50% of inhibition
iPrOH: isopropanol
KOAc: potassium acetate
m: massif
min: minutes
MeOH: methanol
MeONa: sodium methoxide
MIC: minimum inhibitory concentration
MS: mass spectrometry
MsCl: methanesulfonyl chloride
MTBE: methyl tert-butyl ether
NBS: N-bromosuccinimide
Ni(COD)$_2$: Bis(1,5-cyclooctadiene)nickel(0)
NMR: nuclear magnetic resonance spectroscopy
Ns: nosyl, nitrobenzenesulfonyl
Pd(dppf)Cl$_2$: [1,1'-bis(diphenylphosphino)ferrocene]dichloropalladium Pd(PPh₃)₄: tetrakis(triphenylphosphine)palladium(0)
PEPPSI: [1,3-bis(2,6-diisopropylphenyl)imidazol-2-ylidene](3-chloropyridyl)palladium(II) dichloride
PG: protective group
PMe₃: trimethylphosphine
PPh₃: triphenylphosphine
Ppm: parts per million
q: quadruplet
qd: doublet of quadruplet
rt: room temperature
s: singlet
SEM: 2-(trimethylsilyl)ethoxy]methyl acetal
t: triplet
TBAF: tetrabutylammonium fluoride
TBDMS: tert-butyldimethylsilyl
TBDMSOTf: tert-butyldimethylsilyl trifluoromethanesulfonate
TBS: tert-butylsilyl TEA: trimethylamine
Tf: trifluoromethanesulfonyl
TEMPO: 2,2,6,6-tetramethyl-1-piperidinyloxy, free radical, 2,2,6,6-Tetramethylpiperidine 1-oxyl
TFA: trifluoroacetic acid
THF: tetrahydrofuran
THP: tetrahydropyranyl acetal
TLC: thin layer chromatography
TMSI: iodotrimethylsilane
Tr: trityl The compounds of the present invention of formula (I), (I*), (A), (A*), (B) or (B*) can be prepared respectively by the following reaction schemes 1 to 10 depending on R¹.

It should be understood that the processes of schemes 1 to 9 can be adapted for preparing further compounds according to the invention. Further processes for the preparation of compounds according to the invention can be derived from the processes of schemes 1 to 11.

Scheme 1

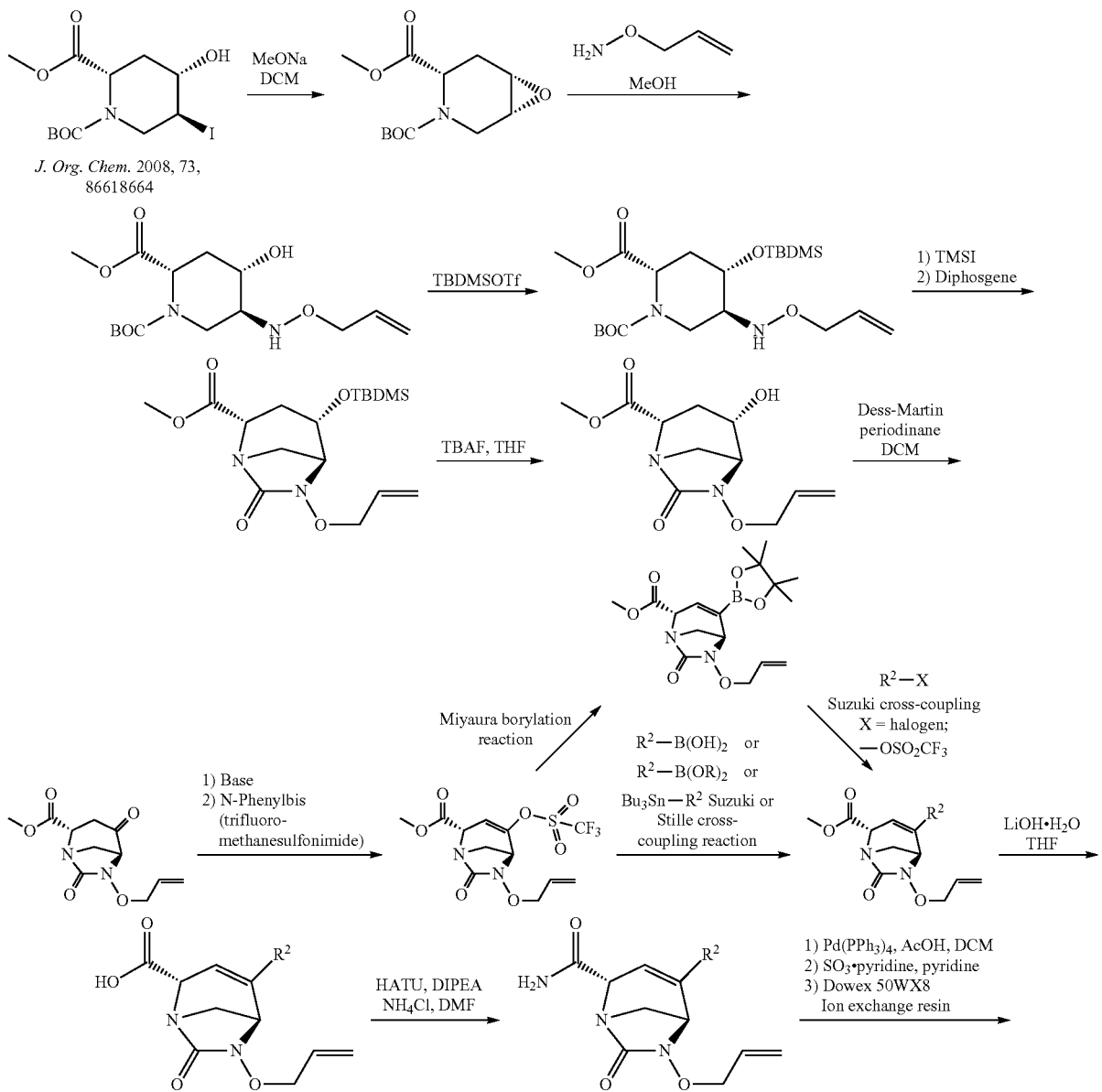

*J. Org. Chem.* 2008, 73, 86618664

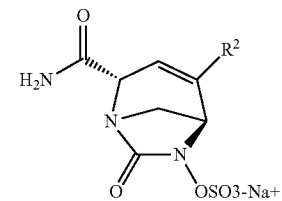
where R1 = —CONH₂
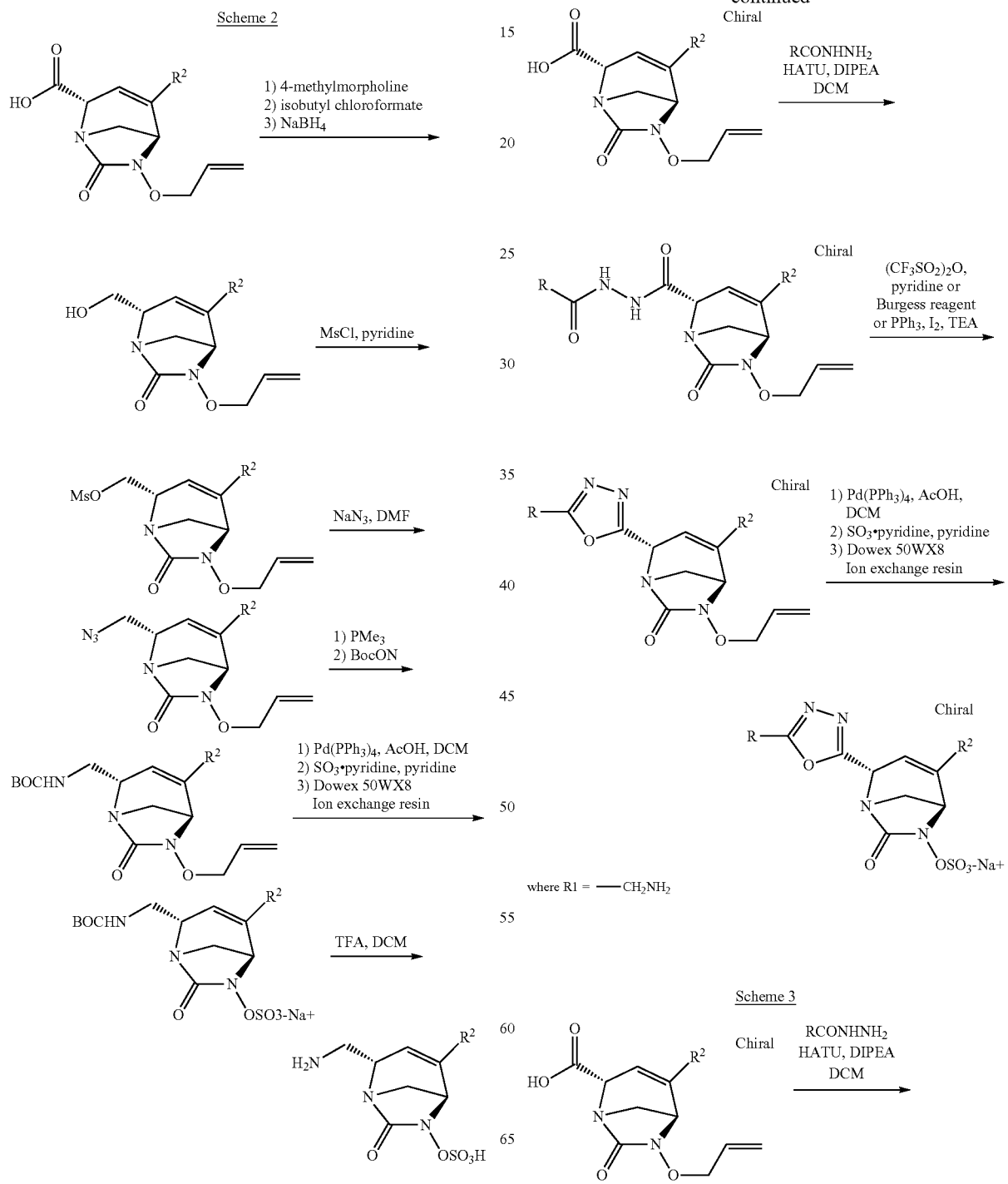

25
-continued
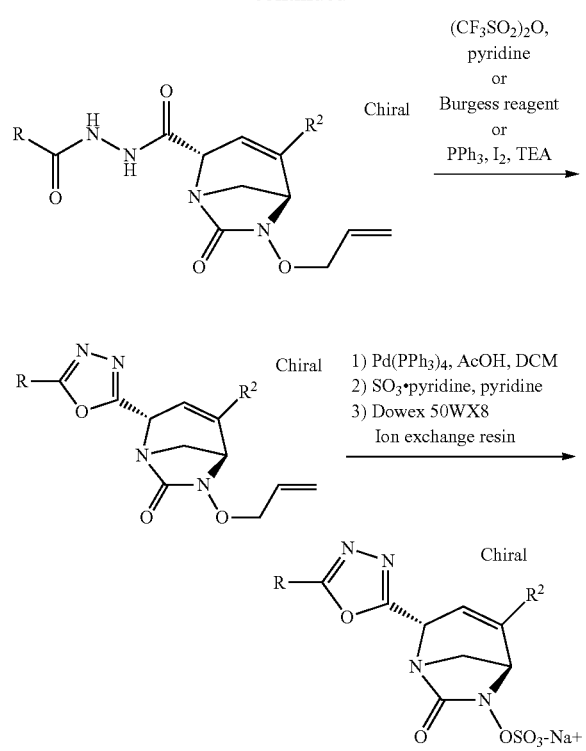
where R1 = heterocycle
Scheme 4
26
-continued
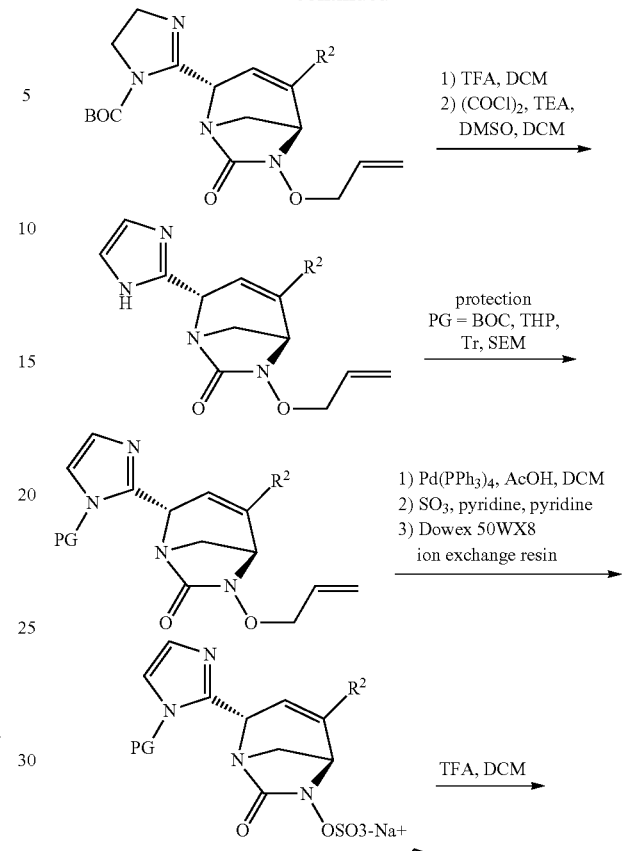
where R1 = heterocycle
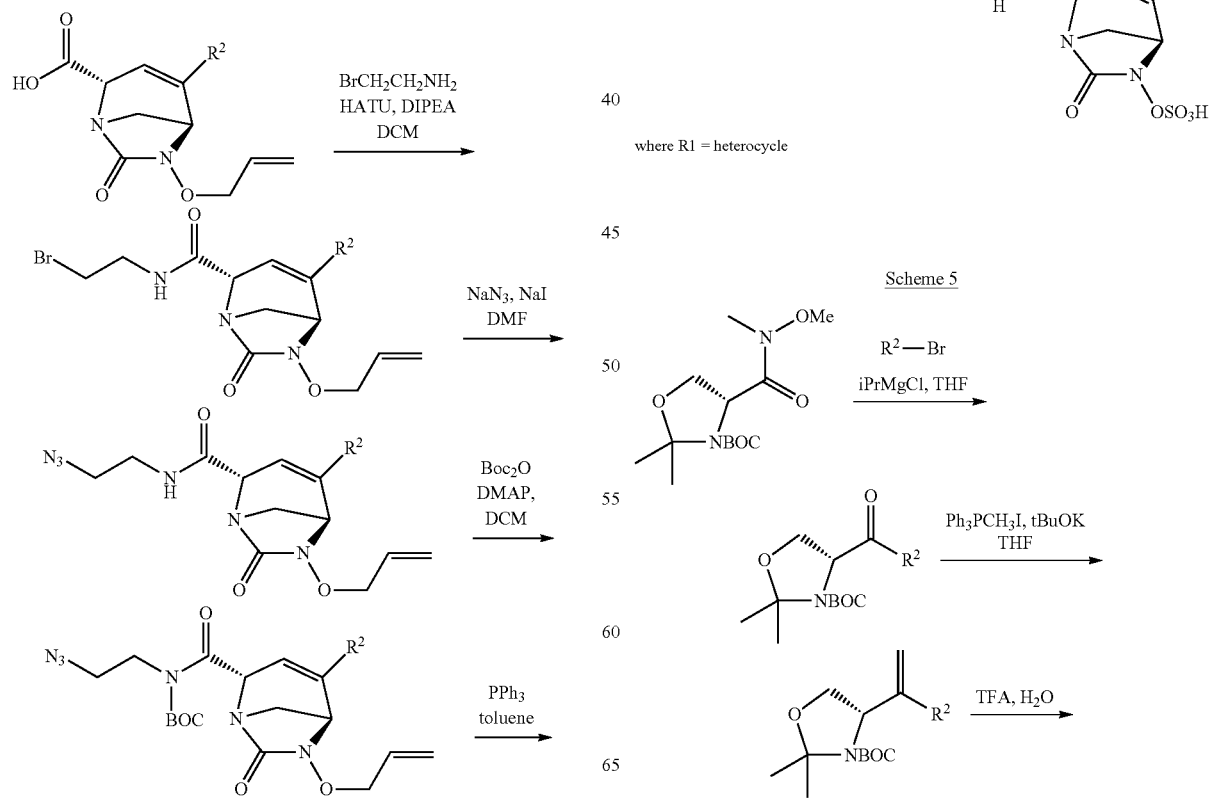
Scheme 5

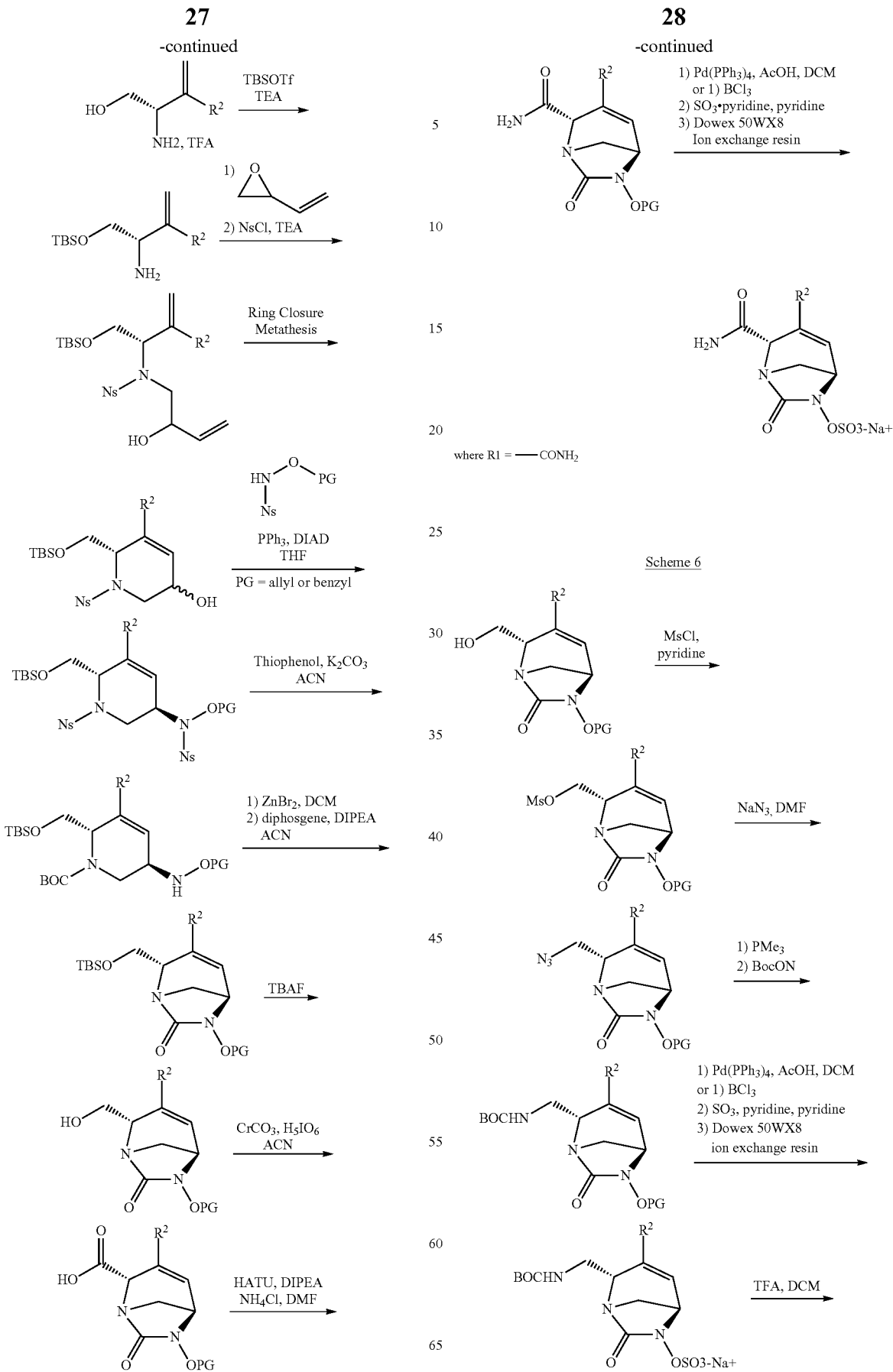

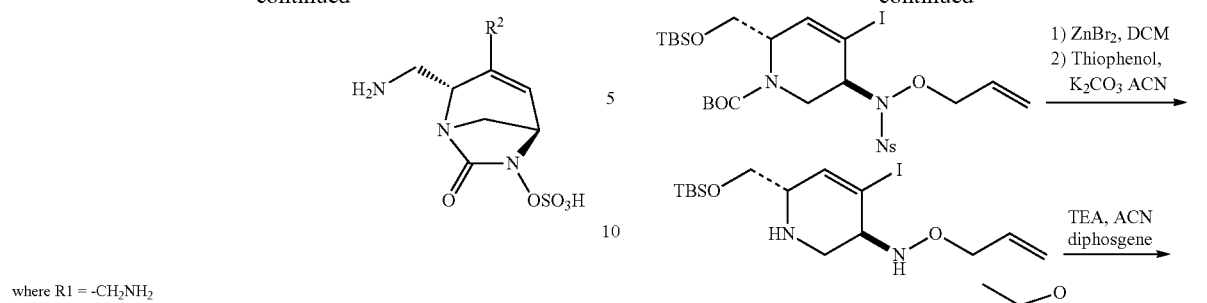
where R1 = -CH$_2$NH$_2$
Scheme 7
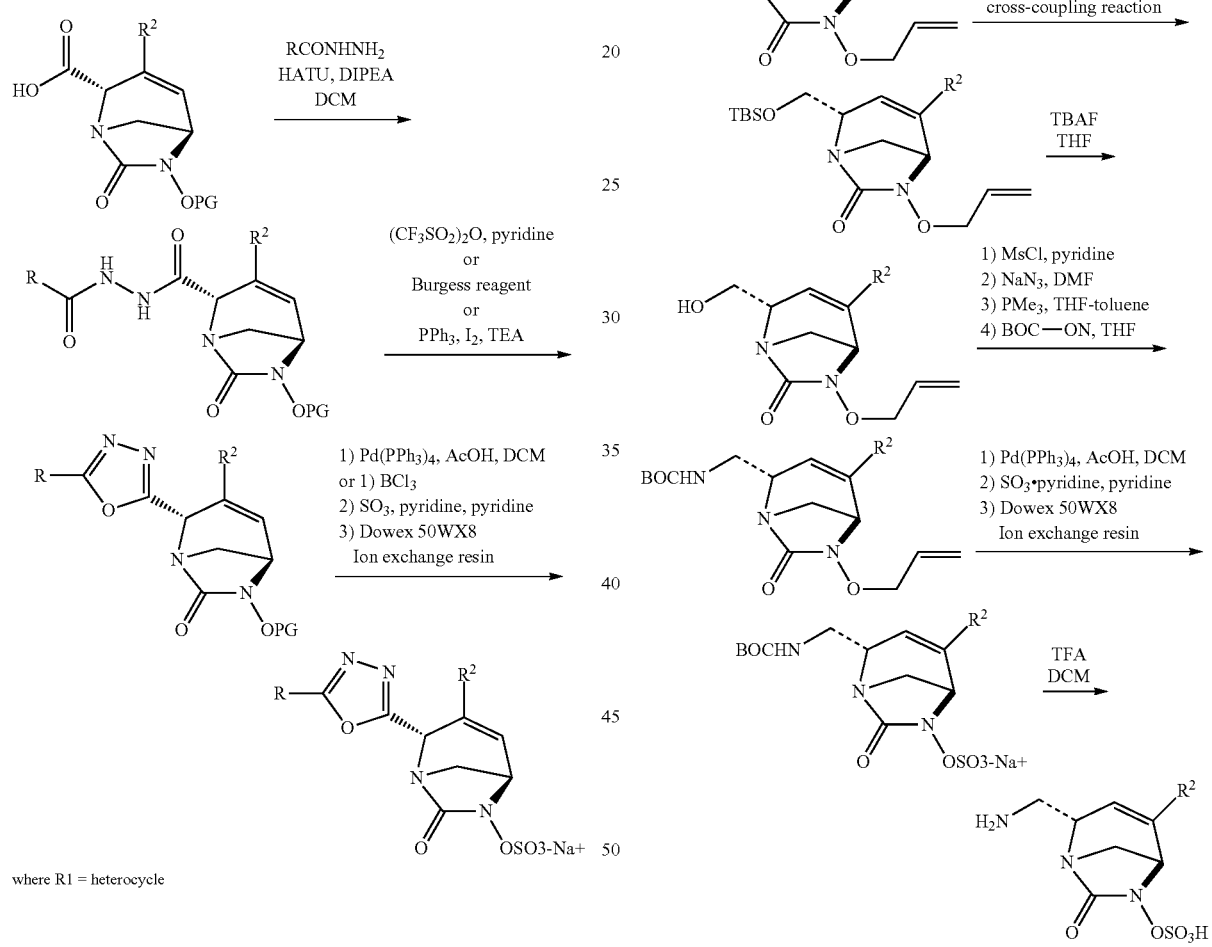
where R1 = heterocycle
where R1 = —CH$_2$NH$_2$
Scheme 8a
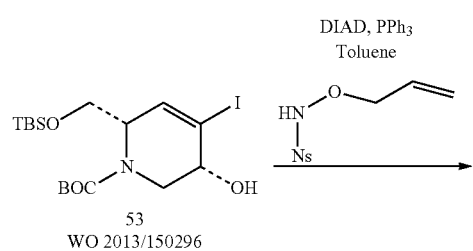
53
WO 2013/150296
Scheme 8b
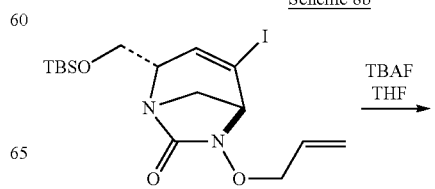

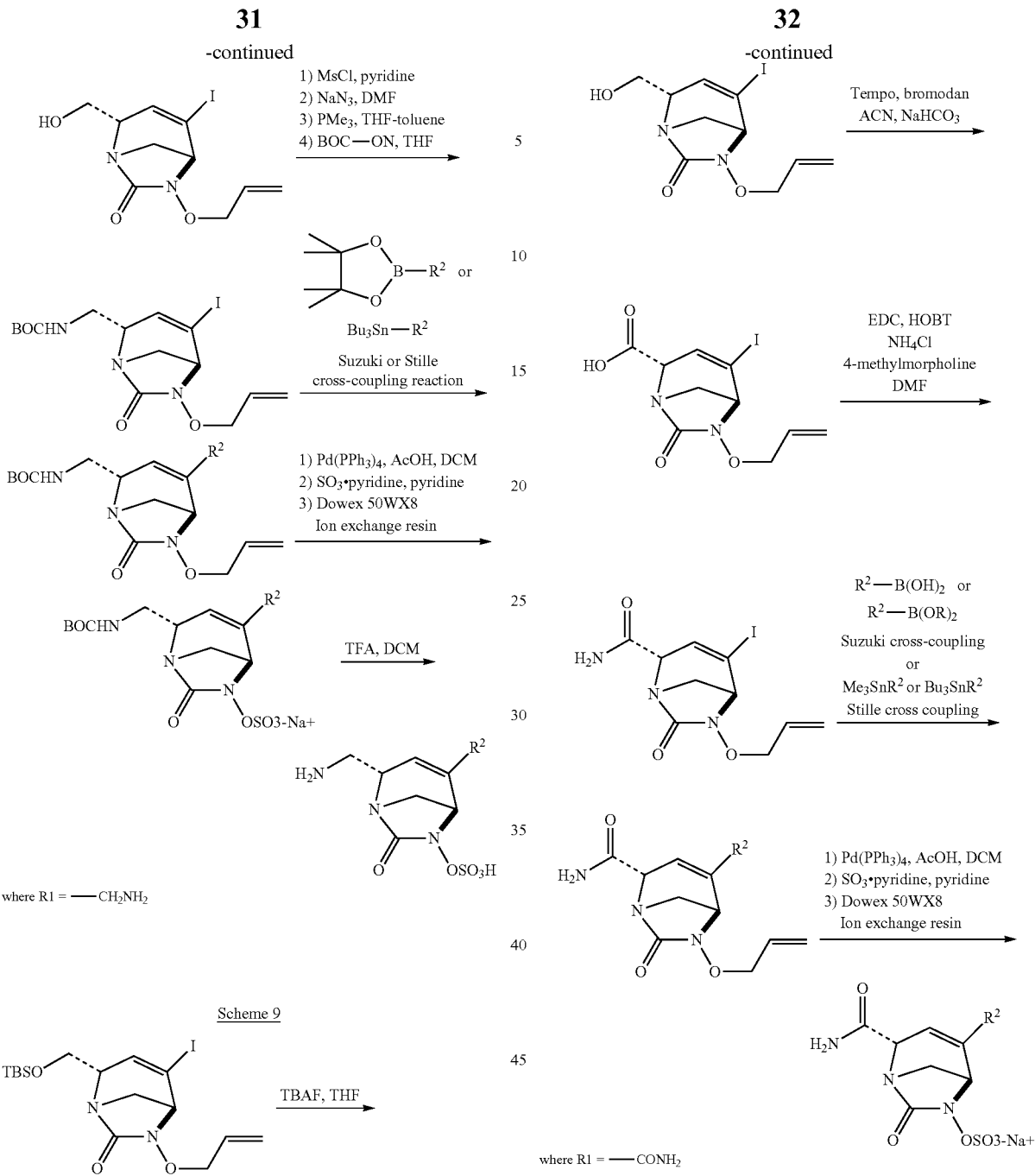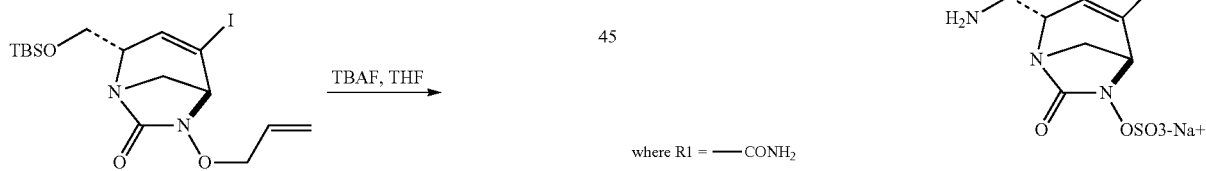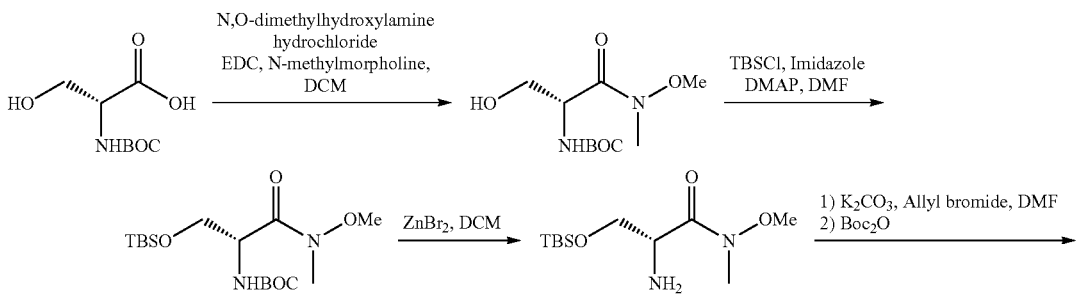

33
34
-continued
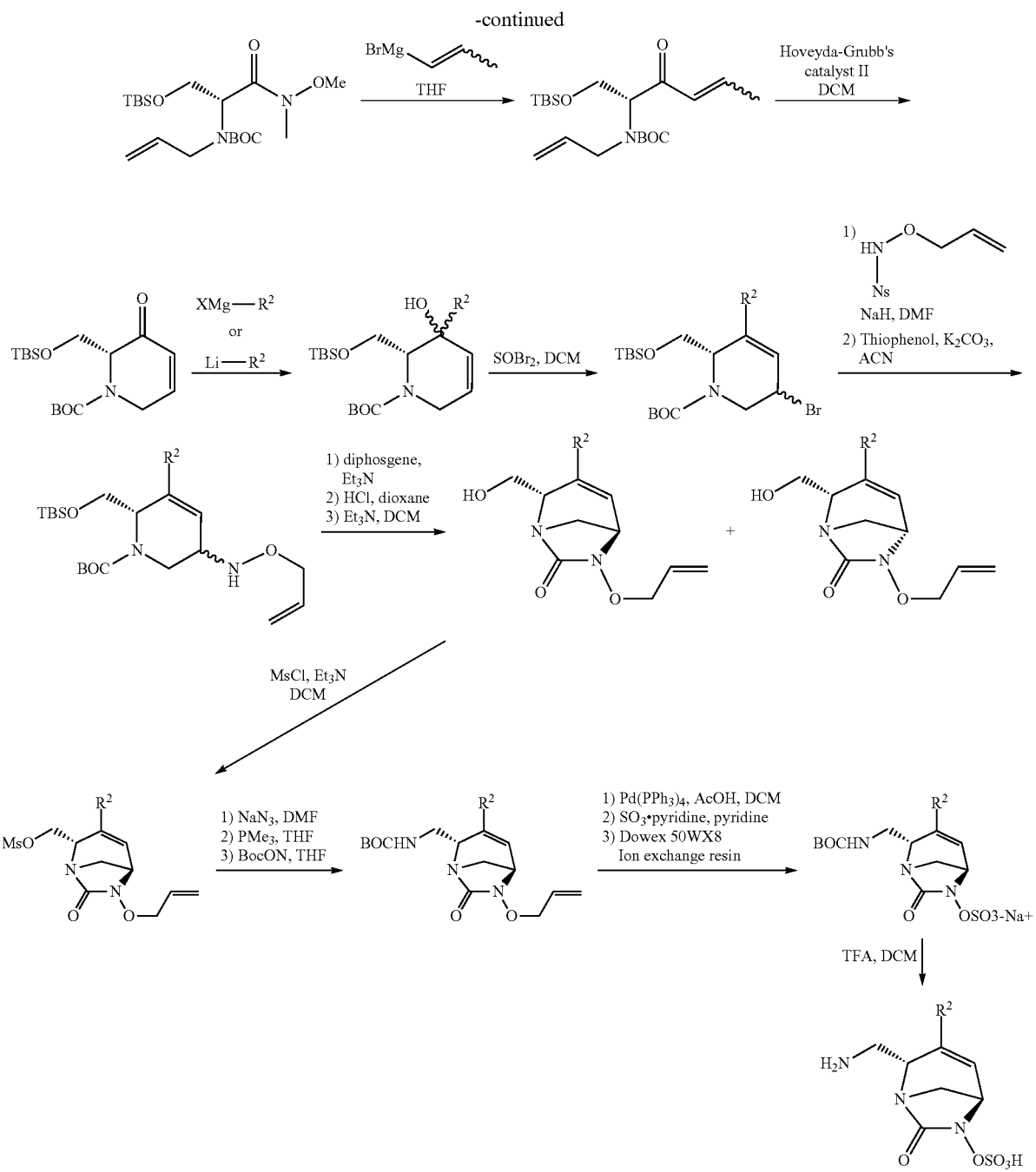
where R1 = —CH₂NH₂
Scheme 10b
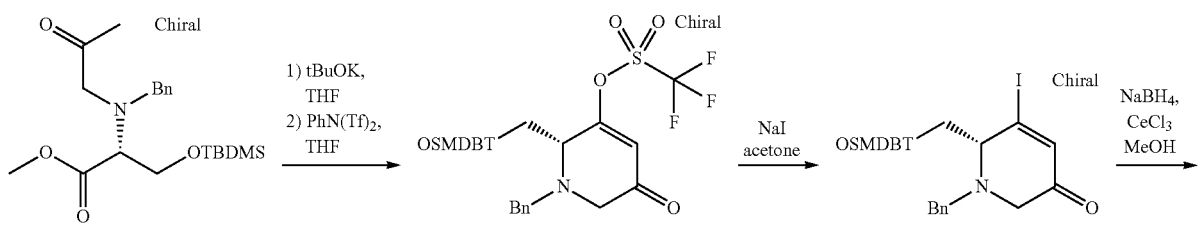

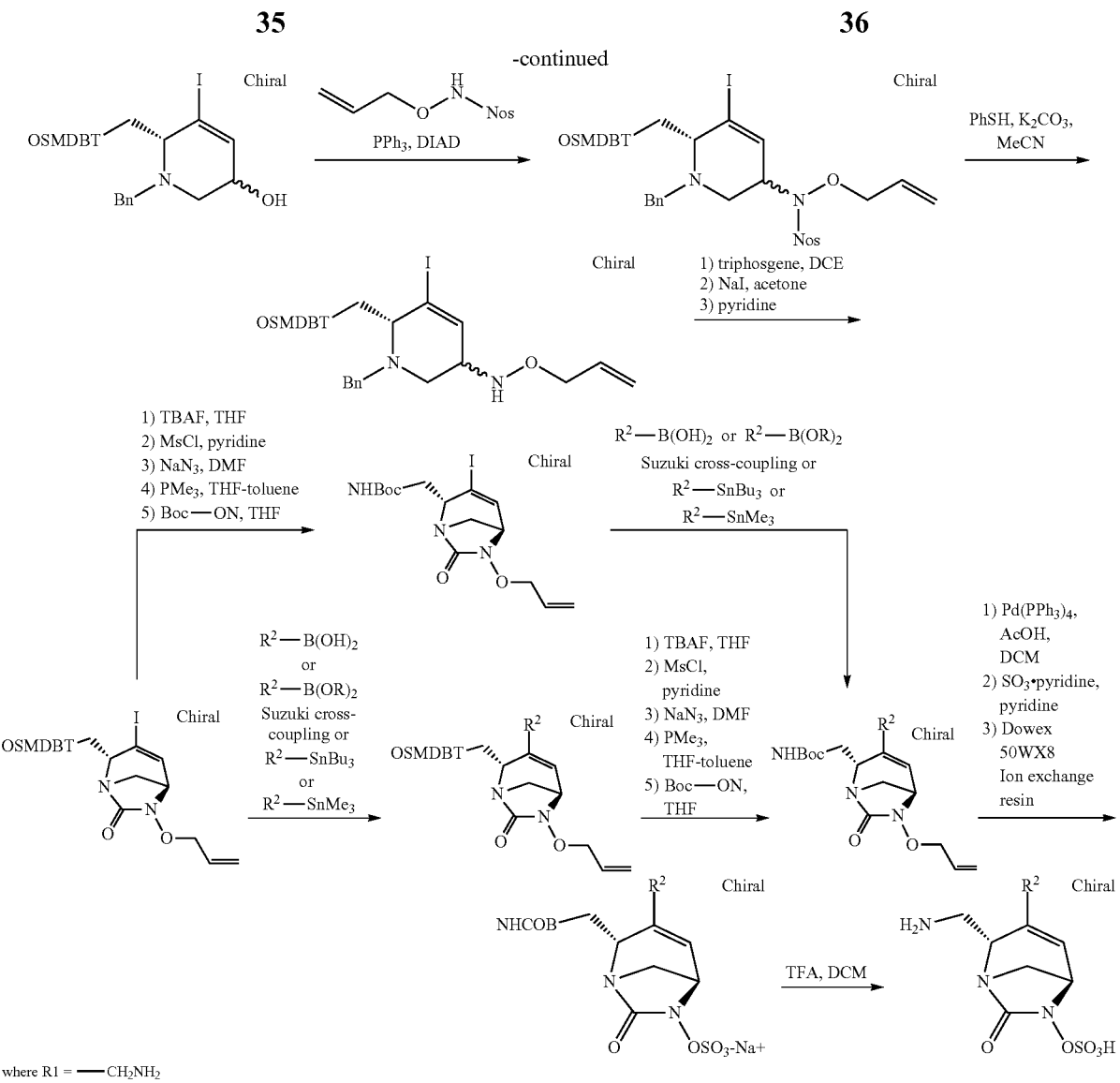
where R1 = —CH₂NH₂
Scheme 11a
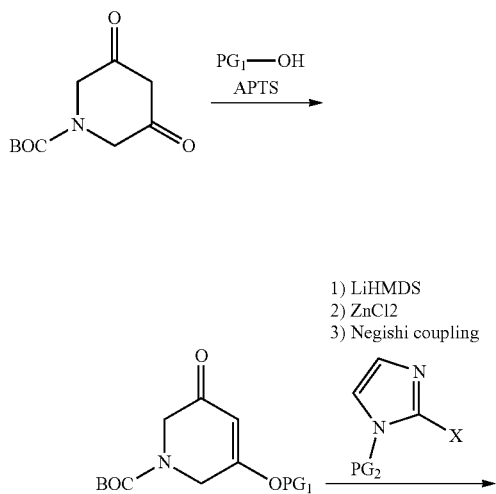
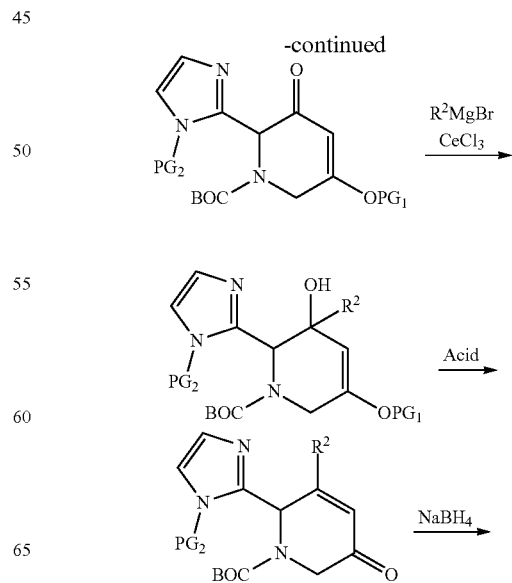

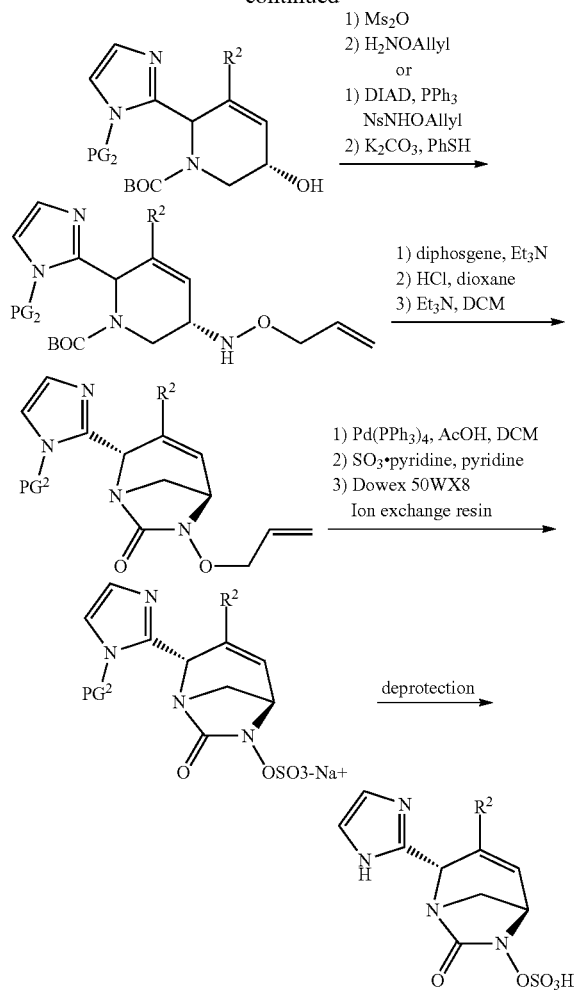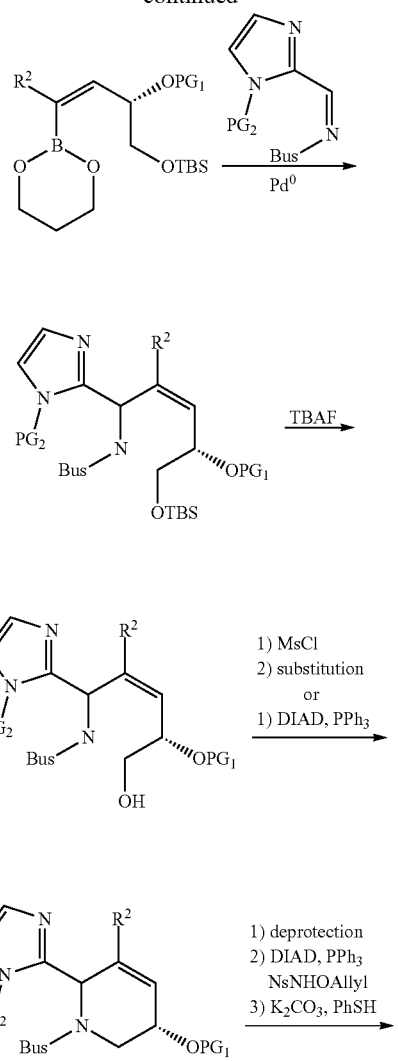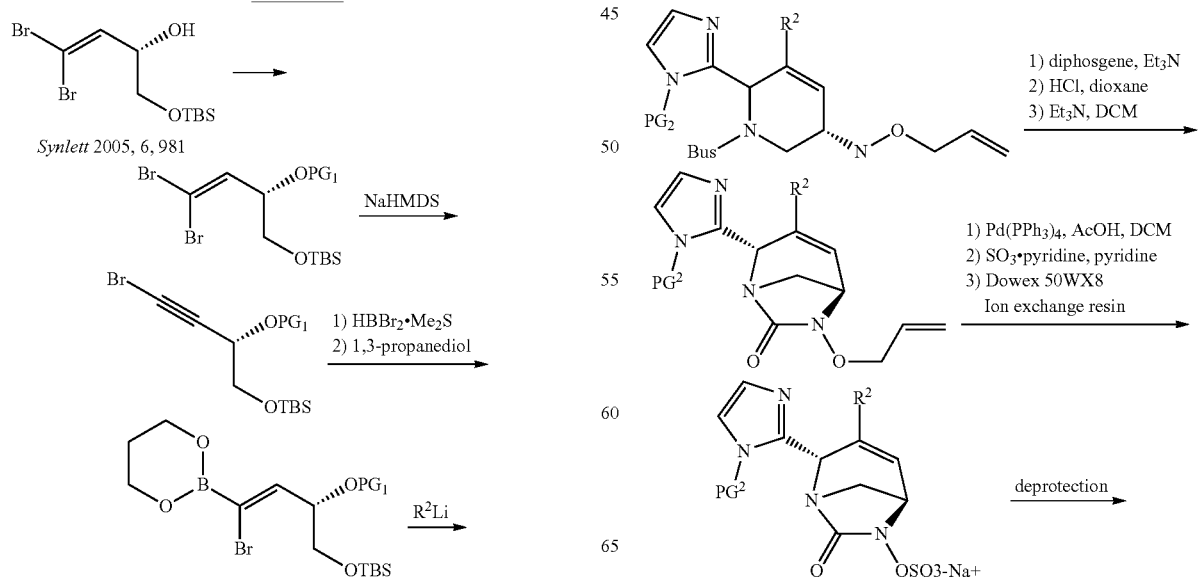

-continued

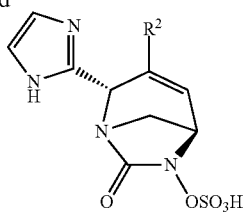

where R1 = heterocycle

EXAMPLES

The following examples are provided for the purpose of illustrating the present invention and by no means should be interpreted to limit the scope of the present invention.

The first part represents the preparation of the compounds (intermediates and final compounds) whereas the second part describes the evaluation of antibacterial activity of compounds according to the invention.

Example 1

Synthesis of Sodium and 2,2,2-trifluoroacetate [trans-2-(azaniumylmethyl)-4-oxazol-5-yl-7-oxo-1, 6-diazabicyclo[3.2.1]oct-3-en-6-yl] sulfate

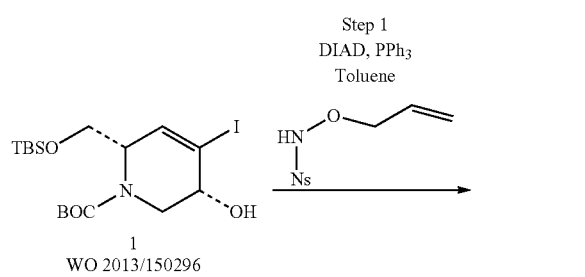

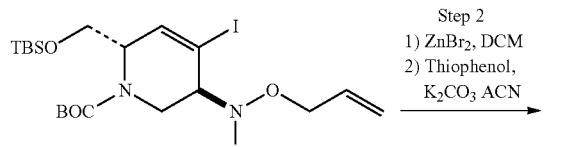

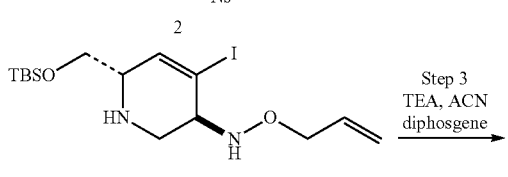

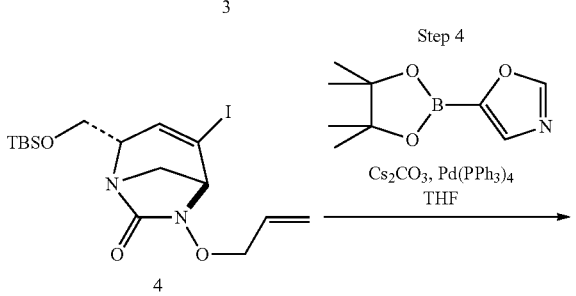

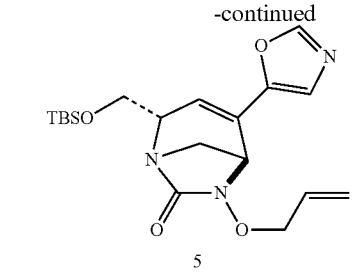

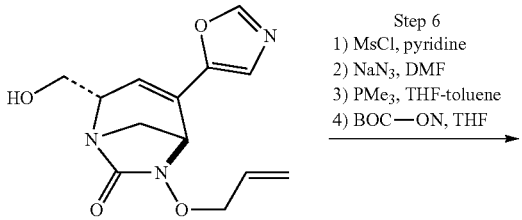

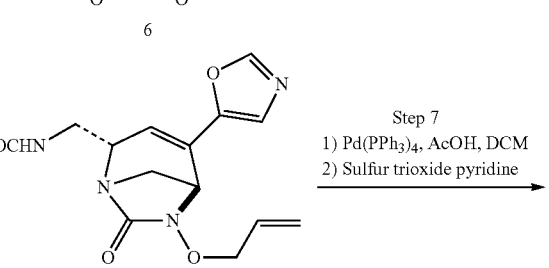

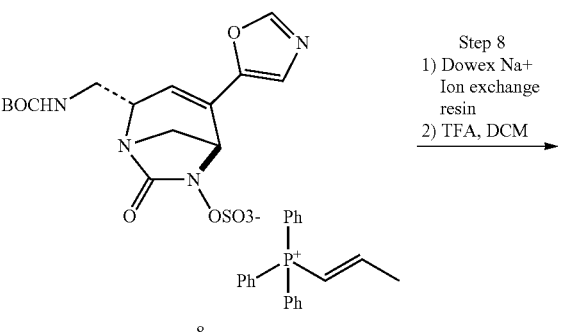

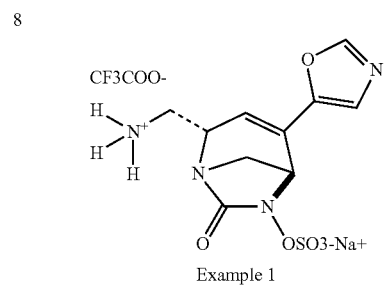

Step 1: Preparation of Intermediate tert-butyl trans-3-[allyloxy-(2-nitrophenyl)sulfonyl-amino]-6-[[tert-butyl(dimethyl)silyl]oxymethyl]-4-iodo-3,6-dihydro-2H-pyridine-1-carboxylate (2)

To a solution of tert-butyl cis-6-[[tert-butyl(dimethyl)silyl]oxymethyl]-3-hydroxy-4-iodo-3,6-dihydro-2H-pyridine-1-carboxylate (1, prepared according to WO 2013/150296) (12.05 g, 25.67 mmol) in toluene (170 mL) at rt was added triphenylphosphine (8.08 g, 30.80 mmol), N-(allyloxy)-2-nitrobenzenesulfonamide (6.63 g, 25.67 mmol) and DIAD (6.06 mL, 30.80 mmol). The reaction mixture was stirred at rt overnight and concentrated in vacuo. The crude was purified by flash chromatography on silica gel (cyclohexane/EtOAc 100/0 to 85/15) to give tert-butyl trans-3-[allyloxy-(2-nitrophenyl)sulfonyl-amino]-6-[[tert-butyl(dimethyl)silyl]oxymethyl]-4-iodo-3,6-dihydro-2H-pyridine-1-carboxylate (2) (17.0 g, 23.95 mmol, 93%).

$^1$H NMR (300 MHz, CDCl$_3$): δ (ppm) 0.03 (s, 6H), 0.88 (s, 9H), 1.35 (s, 9H), 3.16-3.75 (m, 3H), 3.93-4.78 (m, 5H), 5.12-5.38 (m, 2H), 5.68-5.89 (m, 1H), 6.73 (d, J=4.1 Hz, 1H), 7.54-7.66 (m, 1H), 7.69-7.84 (m, 2H), 8.06-8.19 (m, 1H).

Step 2: Preparation of Intermediate trans-N-allyloxy-6-[[tert-butyl(dimethyl)silyl]oxymethyl]-4-iodo-1,2,3,6-tetrahydropyridin-3-amine (3)

To a solution of tert-butyl trans-3-[allyloxy-(2-nitrophenyl)sulfonyl-amino]-6-[[tert-butyl(dimethyl)silyl]oxymethyl]-4-iodo-3,6-dihydro-2H-pyridine-1-carboxylate (2) (17.0 g, 23.95 mmol) in DCM (177 mL) was added ZnBr$_2$ (16.2 g, 71.86 mmol). The reaction mixture was stirred at rt overnight then diluted with DCM and successively washed with saturated and brine. The organic layer was dried over Na$_2$SO$_4$, filtered and concentrated in vacuo. The crude was diluted with ACN (177 mL). K$_2$CO$_3$ (16.6 g, 119.77 mmol) was added, followed by thiophenol (12.3 mL, 119.77 mmol). The reaction mixture was stirred at rt for 1 h and concentrated in vacuo. DCM was added and the resulting solids were removed by filtration. The filtrate was concentrated in vacuo. The crude was purified by flash chromatography on silica gel (DCM/MeOH 100/0 to 90/10) to give trans-N-allyloxy-6-[[tert-butyl(dimethyl)silyl]oxymethyl]-4-iodo-1,2,3,6-tetrahydropyridin-3-amine (3) (7.99 g, 18.83 mmol, 78%).

MS m/z ([M+H]$^+$) 425.

$^1$H NMR (300 MHz, CDCl$_3$): δ (ppm) 0.06 (s, 6H), 0.89 (s, 9H), 1.82 (bs, 1H), 3.14 (dd, J=12.6, 5.1 Hz, 1H), 3.21 (dd, J=12.6, 3.9 Hz, 1H), 3.37-3.45 (m, 2H), 3.53-3.60 (m, 2H), 4.22 (dq, J=6.0, 1.2 Hz, 2H), 5.18-5.25 (m, 1H), 5.25-5.35 (m, 1H), 5.88-5.35 (m, 2H), 6.53-6.56 (m, 1H).

Step 3: Preparation of Intermediate trans-6-allyloxy-2-[[tert-butyl(dimethyl)silyl]oxymethyl]-4-iodo-1,6-diazabicyclo[3.2.1]oct-3-en-7-one (4)

To a solution of trans-N-allyloxy-6-[[tert-butyl(dimethyl)silyl]oxymethyl]-4-iodo-1,2,3,6-tetrahydropyridin-3-amine (3) (7.99 g, 18.83 mmol) in anhydrous ACN (980 mL) at 0° C. under inert atmosphere was added TEA (10.56 mL, 75.31 mmol). A solution of diphosgene (1.14 mL, 9.41 mmol) in anhydrous ACN (20 mL) was dropwise added over 5 h. Once the addition finished, the reaction mixture is allowed to reach rt and stirred for 3 days. H$_2$O was added and the mixture was extracted with EtOAc. The organic layer was dried over Na$_2$SO$_4$, filtered and evaporated in vacuo. The crude was purified by flash chromatography on silica gel (cyclohexane/EtOAc 100/0 to 80/20) to give trans-6-allyloxy-2-[[tert-butyl(dimethyl)silyl]oxymethyl]-4-iodo-1,6-diazabicyclo[3.2.1]oct-3-en-7-one (4) (7.25 g, 16.10 mmol, 85%).

MS m/z ([M+H]$^+$) 451.

$^1$H NMR (300 MHz, CDCl$_3$): δ (ppm) 0.06 (s, 6H), 0.88 (s, 9H), 3.19 (dd, J=11.1, 3.0 Hz, 1H), 3.57 (d, J=11.1 Hz, 1H), 3.80-3.90 (m, 3H), 4.05-4.08 (m, 1H), 4.35-4.53 (m, 2H), 5.28-5.34 (m, 1H), 5.34-5.43 (m, 1H), 5.97-6.12 (m, 1H), 6.37-6.41 (m, 1H).

Step 4: Preparation of Intermediate trans-6-allyloxy-2-[[tert-butyl(dimethyl)silyl]oxymethyl]-4-oxazol-5-yl-1,6-diazabicyclo[3.2.1]oct-3-en-7-one (5)

In a sealed flask, a mixture of trans-6-allyloxy-2-[[tert-butyl(dimethyl)silyl]oxymethyl]-4-iodo-1,6-diazabicyclo[3.2.1]oct-3-en-7-one (4) (5.20 g, 11.55 mmol), 5-(4,4,5,5-tetramethyl-1,2,3-dioxaborolan-2-yl)oxazole (2.70 g, 13.86 mmol) and CsCO$_3$ (7.52 g, 23.09 mmol) in anhydrous THF (100 mL) was degassed under argon for 5 min and Pd(PPh$_3$)$_4$ (400 mg, 0.35 mmol) was added. The mixture was heated at 60° C. overnight. H$_2$O was added and the mixture was extracted with EtOAc. The organic layer was dried over Na$_2$SO$_4$, filtered and concentrated in vacuo. The crude was purified by flash chromatography on silica gel (cyclohexane/EtOAc 100/0 to 70/30) to give trans-6-allyloxy-2-[[tert-butyl(dimethyl)silyl]oxymethyl]-4-oxazol-5-yl-1,6-diazabicyclo[3.2.1]oct-3-en-7-one (5) (3.64 g, 9.30 mmol, 80%).

MS m/z ([M+H]$^+$) 392.

$^1$H NMR (300 MHz, CDCl$_3$): δ (ppm) 0.07 (s, 6H), 0.88 (s, 9H), 3.37 (dd, J=11.0, 3.0 Hz, 1H), 3.54 (d, J=11.0 Hz, 1H), 3.87-4.06 (m, 3H), 4.11-4.14 (m, 1H), 4.33-4.50 (m, 2H), 5.27-5.40 (m, 2H), 5.92-6.08 (m, 1H), 6.15 (d, J=3.0 Hz, 1H), 7.03 (s, 1H), 7.83 (s, 1H).

Step 5: Preparation of Intermediate trans-6-allyloxy-2-(hydroxymethyl)-4-oxazol-5-yl-1,6-diazabicyclo[3.2.1]oct-3-en-7-one (6)

To a solution of trans-6-allyloxy-2-[[tert-butyl(dimethyl)silyl]oxymethyl]-4-oxazol-5-yl-1,6-diazabicyclo[3.2.1]oct-3-en-7-one (5) (3.64 g, 9.30 mmol) in THF (45 mL) at 0° C. was added tetrabutylammonium fluoride (1M in tetrahydrofuran) (13.9 mL, 13.94 mmol). The reaction mixture was stirred at 0° C. for 1 h and concentrated in vacuo. The crude was purified by flash chromatography on silica gel (EtOAc 100%) to give trans-6-allyloxy-2-(hydroxymethyl)-4-oxazol-5-yl-1,6-diazabicyclo[3.2.1]oct-3-en-7-one (6) (1.53 g, 5.52 mmol, 57%).

MS m/z ([M+H]$^+$) 278.

$^1$H NMR (400 MHz, CDCl$_3$): δ (ppm) 3.32 (d, J=11.2 Hz, 1H), 3.40 (dd, J=11.2, 2.9 Hz, 1H), 3.69-3.87 (m, 2H), 4.12-4.19 (m, 2H), 4.36-4.50 (m, 2H), 5.28-5.39 (m, 3H), 5.94-6.06 (m, 2H), 7.06 (s, 1H), 7.83 (s, 1H).

Step 6: Preparation of Intermediate tert-butyl N-[[trans-6-allyloxy-4-oxazol-5-yl-7-oxo-1,6-diazabicyclo[3.2.1]oct-3-en-2-yl]methyl]carbamate (7)

A solution of (trans-6-allyloxy-2-(hydroxymethyl)-4-oxazol-5-yl-1,6-diazabicyclo[3.2.1]oct-3-en-7-one (6) (1.53 g, 5.52 mmol) in pyridine (17 mL) was cooled to 0° C. Methanesulfonyl chloride (0.67 mL, 8.61 mmol) was added and the reaction mixture was stirred at the same temperature for 2 h. After concentrating in vacuo, the crude was dissolved in DCM and successively washed with a solution of 1N HCl and brine. The organic layer was dried over Na$_2$SO$_4$, filtered and evaporated in vacuo. The crude was dissolved in DMF (29 mL) and NaN$_3$ (1.79 g, 27.59 mmol) was added. The reaction mixture was heated at 65° C. overnight and concentrated in vacuo. H$_2$O was added to the crude, which was extracted with EtOAc. The organic layer was washed with brine, dried over Na$_2$SO$_4$, filtered and concentrated in vacuo. The crude was dissolved in a mixture of THF and toluene (16.7 mL/16.7 mL) and trimethylphosphine (1M in tetrahydrofuran) (8.28 mL, 8.28 mmol) was added at 0° C. After 1 h stirring at rt, the mixture was cooled to 0° C. and a solution of 2-(Boc-oxyimino)-2-phenylacetonitrile (2.04 g, 8.28 mmol) in THF (11 mL) was dropwise added. The mixture was stirred at rt for 1 h and concentrated in vacuo. The crude was purified by flash chromatography on silica gel (cyclohexane/EtOAc 95/5 to 0/100) to give tert-butyl N-[[trans-6-allyloxy-4-oxazol-5-yl-7-oxo-1,6-diazabicyclo[3.2.1]oct-3-en-2-yl]methyl]carbamate (7) (440 mg, 1.17 mmol, 21%).

$^1$H NMR (300 MHz, CDCl$_3$): δ (ppm) 1.45 (s, 9H), 3.11-3.30 (m, 1H), 3.37 (dd, J=11.3, 2.9 Hz, 1H), 3.53-3.67 (m, 1H), 3.98-4.07 (m, 1H), 4.15 (d, J=2.9 Hz, 1H), 4.33-4.50 (m, 2H), 4.99-5.12 (m, 2H), 5.28-5.41 (m, 2H), 5.92-6.07 (m, 2H), 7.05 (s, 1H), 7.83 (s, 1H).

MS m/z ([M+H]$^+$) 377.

Step 7: Preparation of Intermediate triphenyl-[(E)-prop-1-enyl]phosphonium [trans-2-[(tert-butoxycarbonylamino)methyl]-4-oxazol-5-yl-7-oxo-1,6-diazabicyclo[3.2.1]oct-3-en-6-yl]sulfate (8)

To a solution of tert-butyl N-[[trans-6-allyloxy-4-oxazol-5-yl-7-oxo-1,6-diazabicyclo[3.2.1]oct-3-en-2-yl]methyl]carbamate (7) (440 mg, 1.17 mmol) and glacial acetic acid (134 µL, 2.34 mmol) in anhydrous DCM (13 mL) was added in one portion Pd(PPh$_3$)$_4$ (675 mg, 0.58 mmol). After stirring for 2 h, a solution of sulfur trioxide pyridine complex (753 mg, 4.73 mmol) in dry pyridine (15 mL) was added and the resulting mixture was stirred overnight. The reaction mixture was concentrated in vacuo, diluted with DCM and filtered. The filtrate was concentrated in vacuo. The crude was purified by flash chromatography on silica gel (DCM/acetone 97/3 to 20/80) to give triphenyl-[(E)-prop-1-enyl]phosphonium [trans-2-[(tert-butoxycarbonylamino)methyl]-4-oxazol-5-yl-7-oxo-1,6-diazabicyclo[3.2.1]oct-3-en-6-yl]sulfate (8) (560 mg, 0.78 mmol, 67%).

$^1$H NMR (300 MHz, CDCl$_3$): δ (ppm) 1.45 (s, 9H), 2.23-2.28 (m, 3H), 3.07-3.31 (m, 2H), 3.46-3.67 (m, 2H), 3.91-4.01 (m, 1H), 4.77 (bs, 1H), 5.10-5.27 (m, 1H), 5.85 (bs, 1H), 6.52-6.70 (m, 1H), 7.11-7.24 (m, 1H), 7.60-7.82 (m, 1H).

Step 8: Preparation of Sodium and 2,2,2-trifluoroacetate [trans-2-(azaniumylmethyl)-4-oxazol-5-yl-7-oxo-1,6-diazabicyclo[3.2.1]oct-3-en-6-yl] sulfate (Example 1)

A solution of triphenyl-[(E)-prop-1-enyl]phosphonium [trans-2-[(tertbutoxycarbonylamino) methyl]-4-oxazol-5-yl-7-oxo-1,6-diazabicyclo[3.2.1]oct-3-en-6-yl] sulfate (8) (560 mg, 0.78 mmol) dissolved in a mixture of H$_2$O/THF 7/3 (1 mL) was applied on a Dowex sodium form column (Dowex® 50WX8 hydrogen form stored with an aqueous solution of 2N NaOH and washed until neutral pH with H$_2$O). The fractions containing the desired compound were combined and concentrated in vacuo. The product was dissolved in ACN and the remaining precipitate was filtered off. The filtrate was concentrated in vacuo. The crude was dissolved in DCM (28 mL), cooled to 0° C., and trifluoroacetic acid (18.5 mL) was dropwise added. After 1 h stirring at the same temperature, the reaction mixture was concentrated in vacuo, dissolved in a minimum of H$_2$O, freezed and lyophilized to afford sodium and 2,2,2-trifluoroacetate [trans-2-(azaniumylmethyl)-4-oxazol-5-yl-7-oxo-1,6-diazabicyclo[3.2.1]oct-3-en-6-yl] sulfate (example 1) (350 mg, 0.77 mmol, 99%).

$^1$H NMR (300 MHz, DMSO-d$_6$): δ (ppm) 3.10-3.26 (m, 1H), 3.29 (dd, J=11.7, 2.9 Hz, 1H), 3.46 (d, J=11.7 Hz, 1H), 4.02-4.11 (m, 1H), 4.59 (d, J=2.2 Hz, 1H), 6.00 (d, J=3.3 Hz, 1H), 7.30 (s, 1H), 8.09 (bs, 3H), 8.42 (s, 1H).

Example 2

Synthesis of Sodium and 2,2,2-trifluoroacetate [(2S,5R)-2-(azaniumylmethyl)-7-oxo-3-thiazol-2-yl-1,6-diazabicyclo[3.2.1]oct-3-en-6-yl] sulfate

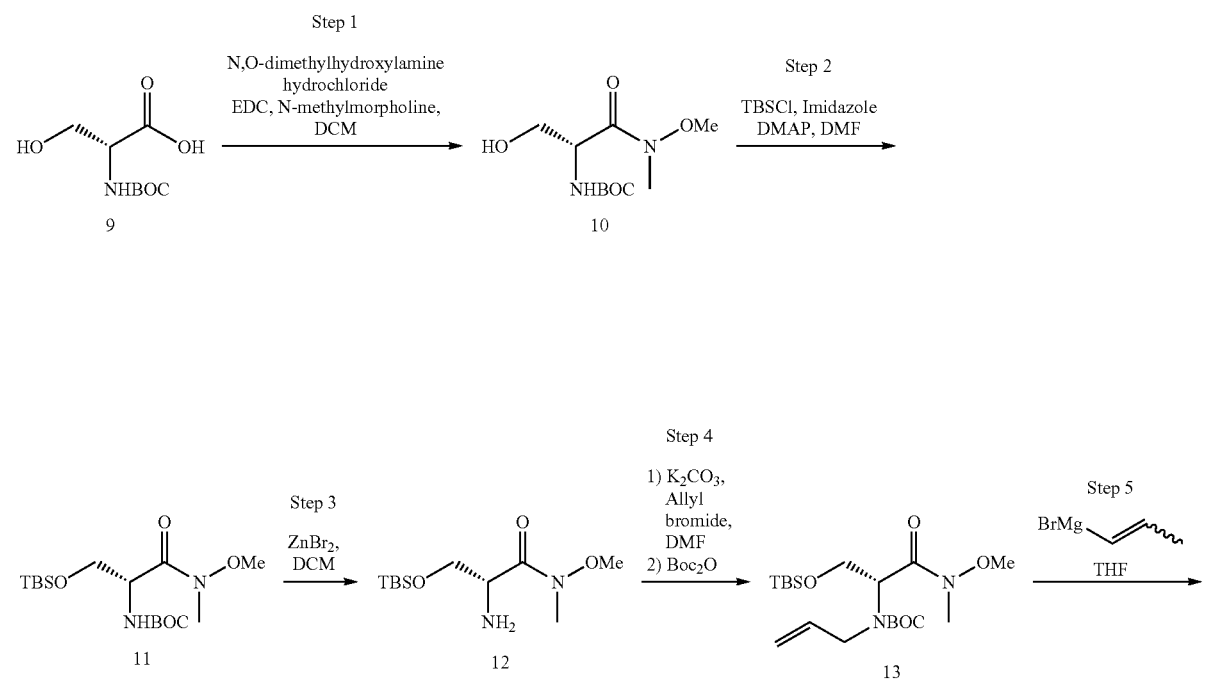

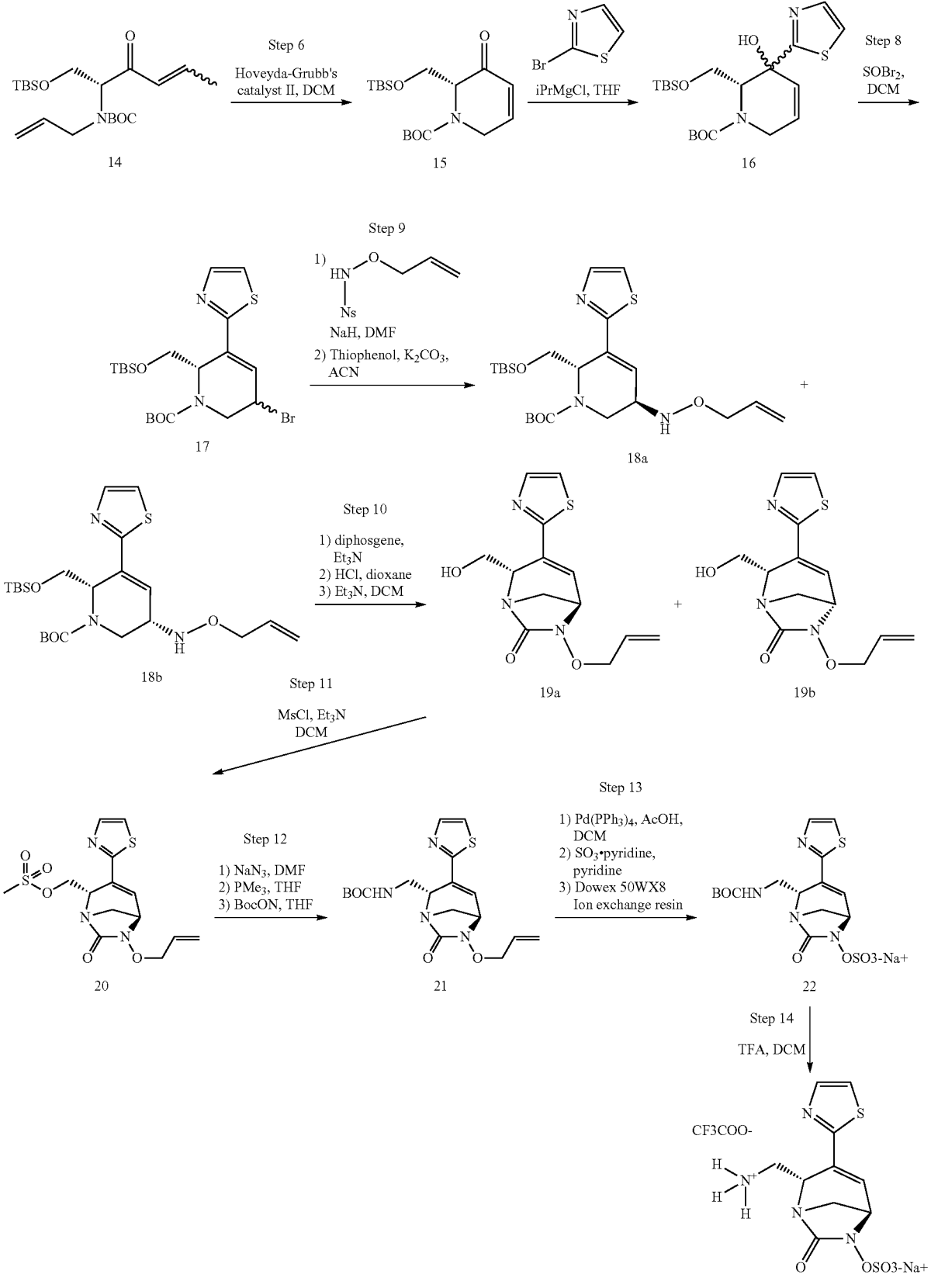

Step 1: Preparation of Intermediate tert-butyl N-[(1R)-1-(hydroxymethyl)-2-[methoxy(methyl) amino]-2-oxo-ethyl]carbamate (10)

To a solution of Boc-D-Ser-OH (9) (5 g, 24.37 mmol) in anhydrous DCM (100 mL) at −15° C. were added N,O-dimethylhydroxylamine hydrochloride (2.54 g, 26.07 mmol) and N-methylmorpholine (2.87 mL, 26.07 mmol). N-(3-Dimethylaminopropyl)-N'-ethylcarbodiimide hydrochloride (5.00 g, 26.07 mmol) was then added portionwise (5 portions) over 20 min. The mixture was stirred at −15° C. for 40 min. A 1M HCl solution (50 mL) was added. The mixture was extracted with DCM (2×25 mL). The organic layer was washed with a saturated solution of NaHCO$_3$ (50 mL), H$_2$O (50 mL), dried over Na$_2$SO$_4$ and concentrated in vacuo to provide the tert-butyl N-[(1R)-1-(hydroxymethyl)-2-[methoxy(methyl)amino]-2-oxo-ethyl]carbamate (10) (5.42 g, 21.83 mmol, 89%) as a white solid.

$^1$H NMR (400 MHz, CDCl$_3$) δ 1.44 (s, 9H), 2.65 (s, 1H), 3.23 (s, 3H), 3.62-3.97 (m, 5H), 4.79 (s, 1H), 5.60 (d, J=8.4 Hz, 1H).

Step 2: Preparation of Intermediate tert-butyl N-[(1R)-1-[[tert-butyl(dimethyl)silyl]oxymethyl]-2-[methoxy(methyl)amino]-2-oxo-ethyl]carbamate (11)

To a solution of compound (10) (5.42 g, 21.8 mmol), imidazole (4.46 g, 65.5 mmol) and DMAP (133 mg, 1.1 mmol) in anhydrous DMF (17 mL) at rt was portionwise added tert-butyldimethylsilyl chloride (3.95 g, 26.2 mmol). The mixture was stirred for 2 h then poured in H$_2$O (50 mL). The aqueous layer was extracted with EtOAc (2×40 mL). The organic layer was washed with 1 M HCl (50 mL), brine (40 mL), dried over Na$_2$SO$_4$ and concentrated in vacuo. The residue was purified by flash chromatography on silica gel (cyclohexane/EtOAc 100/0 to 50/50) to provide tert-butyl N-[(1R)-1-[[tert-butyl(dimethyl)silyl]oxymethyl]-2-[methoxy(methyl)amino]-2-oxo-ethyl]carbamate (11) (7.09 g, 19.5 mmol, 89%) as a colorless oil.

MS m/z ([M+Na]$^+$) 385, ([M+H]$^+$) 363.

$^1$H NMR (400 MHz, CDCl$_3$) δ 0.03 (s, 6H), 0.87 (s, 9H), 1.44 (s, 9H), 3.21 (s, 3H), 3.64-3.94 (m, 5H), 4.75 (s, 1H), 5.35 (d, J=9.0 Hz, 1H).

Step 3: Preparation of Intermediate (2R)-2-amino-3-[tert-butyl(dimethyl)silyl]oxy-N-methoxy-N-methyl-propanamide (12)

A solution of compound (11) (4.60 g, 12.69 mmol) and ZnBr$_2$ (5.71 g, 25.38 mmol) in DCM (37 mL) was stirred at room temperature for 2 h30. A 2M NaOH solution (25 mL) was added followed by H$_2$O (25 mL). The suspension was filtrated. The solid was washed with H$_2$O and DCM. The filtrate was extracted with DCM. The organic layer was washed with brine, dried over Na$_2$SO$_4$ and concentrated in vacuo to provide (2R)-2-amino-3-[tert-butyl(dimethyl)silyl]oxy-N-methoxy-N-methyl-propanamide (12) (3.17 g, 12.08 mmol, 96%) as a colorless oil.

MS m/z ([2M+H]$^+$) 525, ([M+H]$^+$) 263.

$^1$H NMR (400 MHz, CDCl$_3$) δ 0.07 (s, 6H), 0.90 (s, 9H), 1.71 (bs, 2H), 3.23 (s, 3H), 3.63 (dd, J=9.6, 6.6 Hz, 1H), 3.74 (s, 3H), 3.81 (dd, J=9.6, 5.4 Hz, 1H), 3.87-3.96 (m, 1H).

Step 4: Preparation of Intermediate tert-butyl N-allyl-N-[(1R)-1-[[tert-butyl(dimethyl)silyl]oxymethyl]-2-[methoxy(methyl)amino]-2-oxo-ethyl]carbamate (13)

To a solution of compound (12) (3.17 g, 12.08 mmol) in anhydrous DMF (24 mL) at 0° C. was added K$_2$CO$_3$ (3.34 g, 24.16 mmol). The mixture was stirred at this temperature for 20 min before adding allyl bromide (1.15 mL, 13.29 mmol). The mixture was stirred for 1 h at 0° C. then 2 h at rt. Di-tert-butyl dicarbonate (3.95 g, 18.12 mmol) was added and the mixture maintained at rt overnight. H$_2$O (50 mL) was added. The mixture was extracted with EtOAc (2×30 mL). The organic layer was washed with brine (40 mL), dried over Na$_2$SO$_4$ and concentrated in vacuo. The residue was purified by flash chromatography on silica gel (cyclohexane/EtOAc: 90/10) to provide tert-butyl N-allyl-N-[(1R)-1-[[tert-butyl(dimethyl)silyl]oxymethyl]-2-[methoxy(methyl)amino]-2-oxo-ethyl]carbamate (13) (2.06 g, 5.11 mmol, 42%) as a colorless oil.

MS m/z ([M+Na]$^+$) 425, ([M+H]$^+$) 403.

$^1$H NMR (400 MHz, CDCl$_3$) δ 0.05 (s, 6H), 0.87 (s, 9H), 1.38-1.60 (m, 9H), 3.16 (s, 3H), 3.73 (s, 3H), 3.78-4.07 (m, 4H), 4.87-5.40 (m, 3H), 5.68-5.96 (m, 1H).

Step 5: Preparation of Intermediate tert-butyl N-allyl-N-[(1R)-1-[[tert-butyl(dimethyl)silyl]oxymethyl]-2-oxo-pent-3-enyl]carbamate (14)

A solution of compound (13) (1.84 g, 4.57 mmol) in anhydrous THF (5 mL) was dropwise added to a propen-1-ylmagnesium bromide solution 0.5M in THF (18.3 mL, 9.14 mmol) at 0° C. under nitrogen atmosphere. The mixture was stirred at 0° C. for 20 min. H$_2$O (15 mL) and a saturated solution of NH$_4$Cl (15 mL) were added. The mixture was extracted with tert-butyl methyl ether (2×20 mL). The organic layer was washed with 1M HCl (20 mL), dried over Na$_2$SO$_4$ and concentrated in vacuo to provide tert-butyl N-allyl-N-[(1R)-1-[[tert-butyl(dimethyl)silyl]oxymethyl]-2-oxo-pent-3-enyl]carbamate (14) (1.70 g, 4.43 mmol, 97%) which was used without further purification.

MS m/z ([M+Na]$^+$) 406.

Step 6: Preparation of Intermediate tert-butyl (2R)-2-[[tert-butyl(dimethyl)silyl]oxymethyl]-3-oxo-2,6-dihydropyridine-1-carboxylate (15)

A solution of compound (14) (2.48 g, 6.47 mmol) and (1,3-Bis-(2,4,6-trimethylphenyl)-2-imidazolidinylidene)dichloro(o-isopropoxyphenylmethylene)ruthenium (203 mg, 0.32 mmol) in DCM was refluxed for 1 h. The mixture was concentrated in vacuo. The residue was purified by flash chromatography on silica gel (DCM/EtOAc: 100/0 to 95/5) to provide tert-butyl (2R)-2-[[tert-butyl(dimethyl)silyl]oxymethyl]-3-oxo-2,6-dihydropyridine-1-carboxylate (15) (2.07 g, 6.06 mmol, 93%) as a greenish solid.

$^1$H NMR (400 MHz, CDCl$_3$) δ −0.04 (s, 3H), −0.01 (s, 3H), 0.82 (s, 9H), 1.47 (s, 6H), 1.50 (s, 3H), 3.70-4.19 (m, 3H), 4.38-4.75 (m, 2H), 6.18 (d, J=10.3, 1H), 6.82-7.08 (m, 1H).

Step 7: Preparation of Intermediate tert-butyl (2R)-2-[[tert-butyl(dimethyl)silyl]oxymethyl]-3-hydroxy-3-thiazol-2-yl-2,6-dihydropyridine-1-carboxylate (16)

To a solution of 2-bromothiazole (1.09 mL, 12.12 mmol) in anhydrous THF (12 mL) under nitrogen atmosphere at 0° C. was dropwise added a isopropylmagnesium chloride solution 2.0 M in THF (6.06 mL, 12.12 mmol). The mixture was stirred at 0° C. for 20 min then a solution of compound (15) (2.07 g, 6.06 mmol) in anhydrous THF (6 mL) was dropwise added. The mixture was stirred at rt for 45 min.

$H_2O$ (15 mL) and a saturated solution of $NH_4Cl$ (15 mL) were added. The layers were separated. The aqueous layer was extracted with EtOAc (2×15 mL). The combined organic layers were washed with brine (20 mL), dried over $Na_2SO_4$ and concentrated in vacuo. The residue was purified by flash chromatography on silica gel (cyclohexane/EtOAc: 80/20 to 40/60) to provide tert-butyl (2R)-2-[[tert-butyl (dimethyl)silyl]oxymethyl]-3-hydroxy-3-thiazol-2-yl-2,6-dihydropyridine-1-carboxylate (16) (1.77 g, 4.15 mmol, 68%) as a brown oil.

MS m/z ($[M+H]^+$) 427.

Step 8: Preparation of Intermediate tert-butyl (6S)-3-bromo-6-[[tert-butyl(dimethyl)silyl]oxymethyl]-5-thiazol-2-yl-3,6-dihydro-2H-pyridine-1-carboxylate (17)

Thionyl bromide (0.36 mL, 4.56 mmol) was dropwise added to a solution of TEA (0.64 mL, 4.56 mmol) and compound (16) (1.77 g, 4.15 mmol) in anhydrous DCM (18 mL) at 0° C. The mixture was stirred at 0° C. for 20 min then poured in a mixture of ice and $H_2O$ (50 mL). The layers were separated. The aqueous layer was extracted with DCM (2×20 mL). The combined organic layers were washed with brine (20 mL) dried over $Na_2SO_4$ and concentrated in vacuo to provide tert-butyl (6S)-3-bromo-6-[[tert-butyl(dimethyl) silyl]oxymethyl]-5-thiazol-2-yl-3,6-dihydro-2H-pyridine-1-carboxylate (17) (1.98 g, 4.04 mmol, 97%) as a brown oil which was used without further purification.

$^1$H NMR (300 MHz, $CDCl_3$) δ −0.26-0.05 (m, 6H), 0.63-0.89 (m, 9H), 1.47-1.53 (m, 9H), 3.78-4.19 (m, 3H), 4.38-4.90 (m, 2H), 5.15-5.56 (m, 1H), 6.73-6.78 (m, 1H), 7.24-7.28 (m, 1H), 7.77-7.82 (m, 1H).

Step 9: Preparation of Intermediate tert-butyl (3R, 6S)-3-(allyloxyamino)-6-[[tert-butyl(dimethyl)silyl] oxymethyl]-5-thiazol-2-yl-3,6-dihydro-2H-pyridine-1-carboxylate (18a) and tert-butyl (3S, 6S)-3-(allyloxyamino)-6-[[tert-butyl(dimethyl)silyl] oxymethyl]-5-thiazol-2-yl-3,6-dihydro-2H-pyridine-1-carboxylate (18b)

To a suspension of NaH 60% in oil (202 mg, 5.06 mmol) in anhydrous DMF (6 mL) at 0° C. under nitrogen atmosphere was portionwise added N-allyloxy-2-nitro-benzenesulfonamide (1.31 g, 5.07 mmol). The mixture was stirred at 0° C. for 15 min then a solution of compound (17) (1.98 g, 4.04 mmol) in anhydrous DMF (6 mL) was dropwise added. The mixture was stirred for 90 min at 0° C. then $H_2O$ (20 mL) was added. The mixture was extracted with EtOAc (2×20 mL). The organic layer was washed with brine (20 mL), dried over $Na_2SO_4$ and concentrated in vacuo. The residue was purified by flash chromatography on silica gel (dichloromethane). The fractions containing the nosylated intermediate were combined and concentrated in vacuo. The residue was dissolved in ACN (30 mL) and $K_2CO_3$ (2.92 g, 21.14 mmol) and thiophenol (2.17 mL, 21.14 mmol) were added. The mixture was stirred at rt for 1 h then concentrated in vacuo. The residue was dissolved in EtOAc (20 mL), washed with a NaOH 2.0 M solution (20 mL), dried over $Na_2SO_4$ and concentrated in vacuo. The residue was purified by flash chromatography on silica gel (dichloromethane/EtOAc: 100/0 to 80/20) to provide compound (18b) (713 mg, 1.48 mmol) and a mixture (18b)/(18a) (30/70) (868 mg, 1.80 mmol) (yield: 81%).

MS m/z ($[M+H]^+$) 482.

(18a) (3R, 6S):
$^1$H NMR (400 MHz, $CDCl_3$) δ −0.30-0.03 (m, 6H), 0.79 (s, 9H), 1.50 (s, 9H), 3.44 and 3.52 (dd, J=13.8, 3.4 Hz, 1H), 3.60-3.72 (m, 1H), 3.85-4.07 (m, 2H), 4.18-4.34 (m, 2H), 4.47 and 4.57 (d, J=13.8 Hz, 1H), 5.10-5.43 (m, 3H), 5.89-6.01 (m, 1H), 6.53 and 6.56 (d, J=5.3 Hz, 1H), 7.21 and 7.22 (d, J=3.3 Hz, 1H), 7.75 and 7.77 (d, J=3.3 Hz, 1H).

(18b) (3S, 6S):
$^1$H NMR (400 MHz, $CDCl_3$) δ −0.18-0.08 (m, 6H), 0.81 (s, 9H), 1.49 (s, 9H), 3.17 and 3.29 (t, J=11.4 Hz, 1H), 3.77-4.07 (m, 3H), 4.17-4.26 (m, 2H), 4.30 and 4.51 (dd, J=12.7, 6.3 Hz, 1H), 5.15-5.51 (m, 4H), 5.89-6.02 (m, 1H), 6.60 (s, 1H), 7.21 (s, 1H), 7.76 (s, 1H).

Step 10: Preparation of Intermediate (2S,5R)-6-allyloxy-2-(hydroxymethyl)-3-thiazol-2-yl-1,6-diazabicyclo[3.2.1]oct-3-en-7-one (19a) and (2S,5S)-6-allyloxy-2-(hydroxymethyl)-3-thiazol-2-yl-1,6-diazabicyclo[3.2.1]oct-3-en-7-one (19b)

To a solution of a mixture cis/trans (30/70) of compounds (18b/18a) (868 mg, 1.80 mmol) in anhydrous DCM (9 mL) at 0° C. under nitrogen were added TEA (0.50 mL, 3.60 mmol) and diphosgene (0.283 mL, 2.34 mmol). The mixture was stirred at 0° C. for 30 min, diluted with DCM (10 mL) and washed with brine (10 mL). The organic layer was dried over $Na_2SO_4$ and concentrated in vacuo. The residue was dissolved in anhydrous dioxane (2 mL) and dropwise added to 4 M HCl solution in dioxane (9 mL). The mixture was stirred at rt for 1 h and concentrated in vacuo. The residue was dissolved in anhydrous dichloromethane (18 mL) cooled at 0° C. and triethylamine (1.0 mL, 7.21 mmol) was added. The mixture was stirred at rt for 15 min then washed with brine (10 mL). The organic layer was dried over $Na_2SO_4$ and concentrated in vacuo. The residue was purified by flash chromatography on silica gel (DCM/EtOAc: 80/20 to 40/60) to provide (2S,5R)-6-allyloxy-2-(hydroxymethyl)-3-thiazol-2-yl-1,6-diazabicyclo[3.2.1]oct-3-en-7-one (19a) (290 mg, 0.99 mmol) and (2S,5S)-6-allyloxy-2-(hydroxymethyl)-3-thiazol-2-yl-1,6-diazabicyclo[3.2.1]oct-3-en-7-one (19b) (115 mg, 0.39 mmol) (yield: 76%).

MS m/z ($[M+H]^+$) 294.

(19a) (3R, 6S):
$^1$H NMR (400 MHz, $CDCl_3$) δ 3.23-3.43 (m, 2H), 3.67 (bs, 1H), 3.94 (dd, J=11.4, 7.2 Hz, 1H), 3.99-4.06 (m, 1H), 4.20 (dd, J=11.6, 4.5 Hz, 1H), 4.32-4.48 (m, 2H), 4.52-4.64 (m, 1H), 5.29 (d, J=10.3 Hz, 1H), 5.34 (dd, J=17.2, 1.5 Hz, 1H), 5.85-6.10 (m, 1H), 6.98 (d, J=5.2 Hz, 1H), 7.23 (d, J=3.3 Hz, 1H), 7.71 (d, J=3.3, 1H).

(19b) (3S, 6S):
$^1$H NMR (400 MHz, $CDCl_3$) δ 3.09 (dd, J=14.1, 3.3 Hz, 1H), 3.72-3.85 (m, 1H), 4.00-4.17 (m, 1H), 4.20-4.40 (m, 3H), 4.86-5.03 (m, 2H), 5.19 (d, J=10.4 Hz, 1H), 5.30 (dd, J=17.3, 1.7 Hz, 1H), 5.45 (d, J=5.4 Hz, 1H), 5.84-6.03 (m, 1H), 6.55 (d, J=5.8 Hz, 1H), 7.30 (d, J=3.2 Hz, 1H), 7.74 (d, J=3.2 Hz, 1H).

Step 11: Preparation of Intermediate [(2S,5R)-6-allyloxy-7-oxo-3-thiazol-2-yl-1,6-diazabicyclo [3.2.1]oct-3-en-2-yl]methyl methanesulfonate (20)

To a solution of compound (19a) (290 mg, 0.989 mmol) in anhydrous DCM (3 mL) at 0° C. under atmosphere of nitrogen were successively added TEA (0.200 mL, 1.43 mmol) and MsCl (92 μL, 1.18 mmol). The mixture was stirred at 0° C. $H_2O$ (5 mL) was added. The layers were separated. The aqueous layer was extracted with DCM (2×5 mL). The combined organic layers were washed with a saturated solution of NaHCO$_3$ (10 mL), dried over Na$_2$SO$_4$ and concentrated in vacuo to provide [(2S,5R)-6-allyloxy-7-oxo-3-thiazol-2-yl-1,6-diazabicyclo[3.2.1]oct-3-en-2-yl] methyl methanesulfonate (20) (337 mg, 0.907 mmol, 92%) as an off white solid.

MS m/z ([M+H]$^+$) 372.

$^1$H NMR (300 MHz, CDCl$_3$) δ 3.00 (s, 3H), 3.40 (ddd, J=11.4, 2.6, 1.3 Hz, 1H), 3.50 (dd, J=11.4, 0.8 Hz, 1H), 4.00-4.10 (m, 1H), 4.34-4.52 (m, 2H), 4.85 (s, 3H), 5.27-5.41 (m, 2H), 5.93-6.10 (m, 1H), 7.07 (d, J=5.2 Hz, 1H), 7.26 (d, J=3.3 Hz, 1H), 7.75 (d, J=3.3 Hz, 1H).

Step 12: Preparation of Intermediate tert-butyl N-[[(2S,5R)-6-allyloxy-7-oxo-3-thiazol-2-yl-1,6-diazabicyclo[3.2.1]oct-3-en-2-yl]methyl]carbamate (21)

A mixture of compound (20) (337 mg, 0.907 mmol) and NaN$_3$ (295 mg, 4.54 mmol) in anhydrous DMF (3.4 mL) was stirred at 65° C. for 20 h. The mixture was poured in H$_2$O (10 mL) and extracted with ethyl acetate (2×10 mL). The organic layer was washed with brine (10 mL), dried over Na$_2$SO$_4$ and concentrated in vacuo. The residue was dissolved in anhydrous THF (3 mL) and anhydrous toluene (3 mL) and cooled at 0° C. under nitrogen atmosphere. A trimethylphosphine solution 1M in THF (1.36 mL, 1.36 mmol) was dropwise added and the mixture was stirred at rt for 1 h. The mixture was cooled at 0° C. and a solution of 2-(Boc-oxyimino)-2-phenylacetonitrile (335 mg, 1.36 mmol) in anhydrous THF (2 mL) was added. The mixture was stirred at rt for 3 h. H$_2$O (10 mL) was added and the layers separated. The aqueous layer was extracted with EtOAc (2×10 mL). The combined organic layers were washed with brine (10 mL), dried over Na$_2$SO$_4$ and concentrated in vacuo. The residue was purified by flash chromatography on silica gel (cyclohexane/EtOAc: 70/30 to 0/100) then by preparative TLC (cyclohexane/EtOAc: 50/50) to provide tert-butyl N-[[(2S,5R)-6-allyloxy-7-oxo-3-thiazol-2-yl-1,6-diazabicyclo[3.2.1]oct-3-en-2-yl]methyl] carbamate (21) (115 mg, 0.292 mmol, 32%) as a white solid.

MS m/z ([M+H]$^+$) 393.

$^1$H NMR (300 MHz, CDCl$_3$) δ 1.44 (s, 9H), 3.18-3.42 (m, 3H), 3.97-4.10 (m, 2H), 4.33-4.51 (m, 2H), 4.61 (ddd, J=11.0, 4.4, 1.4 Hz, 1H), 5.13 (s, 1H), 5.25-5.42 (m, 2H), 5.92-6.11 (m, 1H), 6.94-7.00 (m, 1H), 7.23 (d, J=3.2 Hz, 1H), 7.75 (d, J=3.2 Hz, 1H).

Step 13: Preparation of Intermediate sodium [(2S,5R)-2-[(tert-butoxycarbonylamino)methyl]-7-oxo-3-thiazol-2-yl-1,6-diazabicyclo[3.2.1]oct-3-en-6-yl] sulfate (22)

To a solution of compound (21) (115 mg, 0.293 mmol) in anhydrous DCM (1 mL) under nitrogen atmosphere were successively added AcOH (34 μL, 0.586 mmol) and Pd(PPh$_3$)$_4$ (169 mg, 0.146 mmol). The mixture was stirred at rt for 1 h then concentrated in vacuo. The residue was purified by flash chromatography on silica gel (DCM/acetone: 100/0 to 0/100) to provide a mixture of expected intermediate and triphenylphosphine oxide. The mixture was dissolved in pyridine (2 mL) and sulfur trioxide trimethylamine complex (417 mg, 3.00 mmol) was added. The mixture was stirred at rt overnight then concentrated in vacuo. DCM (5 mL) was added to the residue and the precipitate filtered. The filtrate was concentrated and the residue purified by flash chromatography on silica gel (DCM/acetone: 60/40 to 0/100). The fractions containing the expected intermediate were combined and concentrated in vacuo. The residue was dissolved in H$_2$O (1 mL) and converted after ion exchange (Dowex sodium form column) to sodium [(2S,5R)-2-[(tert-butoxycarbonylamino)methyl]-7-oxo-3-thiazol-2-yl-1,6-diazabicyclo[3.2.1]oct-3-en-6-yl] sulfate (22) (38 mg, 0.083 mmol, 29%) as a white solid.

MS m/z ([M+H]$^+$) 433.

MS m/z ([M−H]$^−$) 431.

$^1$H NMR (400 MHz, D$_2$O) δ 1.39 (s, 9H), 3.34-3.68 (m, 5H), 4.43-4.54 (m, 2H), 7.03 (d, J=5.1 Hz, 1H), 7.52 (d, J=3.4 Hz, 1H), 7.75 (d, J=3.4 Hz, 1H).

Step 14: Preparation of sodium and 2,2,2-trifluoroacetate [(2S,5R)-2-(azaniumylmethyl)-7-oxo-3-thiazol-2-yl-1,6-diazabicyclo[3.2.1]oct-3-en-6-yl] sulfate (Example 2)

A solution of compound (22) (38 mg, 0.083 mmol) in anhydrous DCM (0.67 mL) was added to a mixture of DCM (1 mL) and TFA (1 mL) at 0° C. The mixture was stirred at 0° C. for 30 min then concentrated in vacuo. The residue was co-evaporated three times with DCM (3 mL). The residue was dissolved in H$_2$O (2 mL) and lyophilized to provide sodium and 2,2,2-trifluoroacetate disalt of [(2S,5R)-2-(azaniumylmethyl)-7-oxo-3-thiazol-2-yl-1,6-diazabicyclo[3.2.1]oct-3-en-6-yl] sulfate (Example 2) (35 mg, 0.074 mmol, 89%) as an off white solid.

MS m/z ([M+H]$^+$) 333.

MS m/z ([M−H]$^−$) 331.

$^1$H NMR (300 MHz, D$_2$O) δ 3.36 (dd, J=13.8, 11.4 Hz, 1H), 3.54 (d, J=1.6 Hz, 2H), 3.65 (dd, J=13.8, 3.9 Hz, 1H), 4.53 (dt, J=5.2, 1.6 Hz, 1H), 4.72 (ddd, J=11.4, 3.9, 1.6 Hz, 1H), 7.16 (dd, J=5.2, 1.6 Hz, 1H), 7.53 (d, J=3.3 Hz, 1H), 7.77 (d, J=3.3 Hz, 1H).

Example 3

Synthesis of Lithium and 2,2,2-trifluoroacetate [trans-2-(azaniumylmethyl)-4-oxazol-5-yl-7-oxo-1,6-diazabicyclo[3.2.1]oct-3-en-6-yl]oxyl-2,2-difluoro-acetate

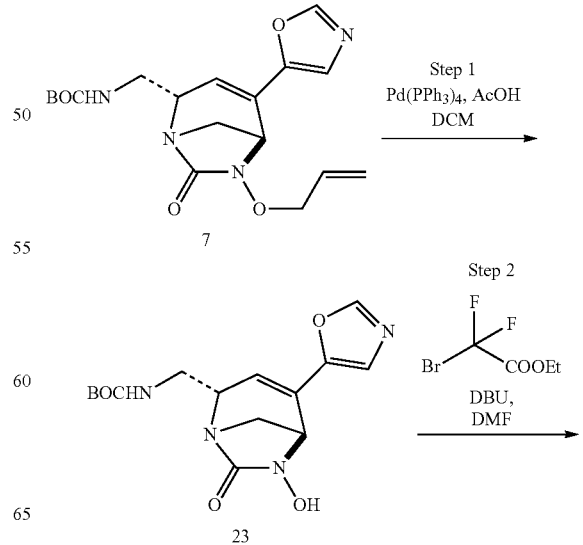

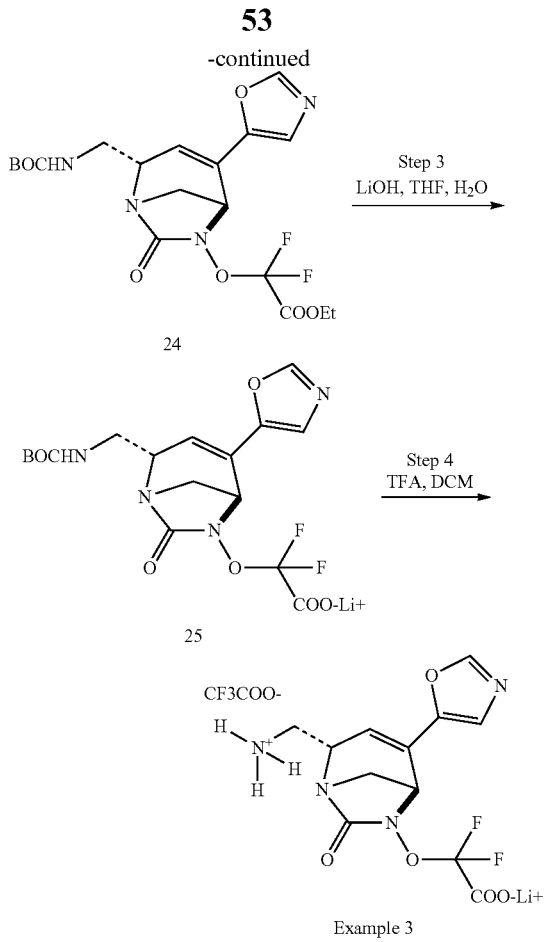

Example 3

Step 1: Preparation of Intermediate tert-butyl N-[[trans-6-hydroxy-4-oxazol-5-yl-7-oxo-1,6-diazabicyclo[3.2.1]oct-3-en-2-yl]methyl]carbamate (23)

To a solution of tert-butyl N-[[trans-6-allyloxy-4-oxazol-5-yl-7-oxo-1,6-diazabicyclo[3.2.1]oct-3-en-2-yl]methyl]carbamate (7) (200 mg, 0.53 mmol) and glacial acetic acid (49 μL, 0.85 mmol) in anhydrous DCM (5.3 mL) was added in one portion Pd(PPh₃)₄ (307 mg, 0.27 mmol). The mixture was stirred at rt for 30 min and concentrated under argon flow. The crude was purified by flash chromatography on silica gel (petroleum ether/acetone 100/0 to 40/60) to give tert-butyl N-[trans-6-hydroxy-4-oxazol-5-yl-7-oxo-1,6-diazabicyclo[3.2.1]oct-3-en-2-yl]methyl]carbamate (23) (176 mg, 0.52 mmol, 90.5%).

MS m/z ([M+H]$^+$) 337.

$^1$H NMR (400 MHz, CDCl₃): δ (ppm) 1.46 (s, 9H), 3.14-3.20 (m, 1H), 3.28 (d, J=11.2 Hz, 1H), 3.42 (dd, J=11.2/2.6 Hz, 1H), 3.58-3.64 (m, 1H), 4.01-4.05 (m, 1H), 4.15-4.16 (m, 1H), 5.10-5.11 (m, 1H), 5.97-5.98 (m, 1H), 7.11 (s, 1H), 7.79 (s, 1H).

Step 2: Preparation of Intermediate ethyl 2-[trans-2-[(tert-butoxycarbonylamino)methyl]-4-oxazol-5-yl-7-oxo-1,6-diazabicyclo[3.2.1]oct-3-en-6-yl]oxy]-2,2-difluoro-acetate (24)

tert-butyl N-[trans-6-hydroxy-4-oxazol-5-yl-7-oxo-1,6-diazabicyclo[3.2.1]oct-3-en-2-yl]methyl]carbamate (23) (161.5 mg, 0.48 mmol) was solubilized in DMF (5.30 mL) at −20° C. with DBU (80 μL, 0.53 mmol) and ethyl 2-bromo-2,2-difluoro-acetate (308 μL, 2.40 mmol). The reaction was stirred for 1h15 at −20° C. Water was added and the mixture was extracted twice with EtOAc. The organic layer was dried over Na₂SO₄, filtered, and concentrated in vacuo. The crude was purified by flash chromatography on silica gel (petroleum ether/acetone 100/0 to 60/40) to give ethyl 2-[trans-2-[(tert-butoxycarbonylamino)methyl]-4-oxazol-5-yl-7-oxo-1,6-diazabicyclo[3.2.1]oct-3-en-6-yl]oxy]-2,2-difluoro-acetate (24) (179 mg, 0.39 mmol, 81%).

MS m/z ([M+H]$^+$) 459.

$^1$H NMR (400 MHz, CDCl₃): δ (ppm) 1.32 (t, J=7.1 Hz, 3H), 1.46 (s, 9H), 3.21-3.29 (m, 1H), 3.37-3.39 (m, 1H), 3.46-3.50 (m, 1H), 3.58-3.64 (m, 1H), 4.11-4.15 (m, 1H), 4.34 (q, J=7.1 Hz, 2H), 4.37-4.38 (m, 1H), 5.0-5.01 (bs, 1H), 6.05-6.06 (m, 1H), 7.15 (s, 1H), 7.84 (s, 1H).

Step 3: Preparation of Intermediate lithium salt of trans-2-[[2-[(tert-butoxycarbonylamino)methyl]-4-oxazol-5-yl-7-oxo-1,6-diazabicyclo[3.2.1]oct-3-en-6-yl]oxy]-2,2-difluoro-acetate (25)

Ethyl 2-[trans-2-[(tert-butoxycarbonylamino)methyl]-4-oxazol-5-yl-7-oxo-1,6-diazabicyclo[3.2.1]oct-3-en-6-yl]oxy]-2,2-difluoro-acetate (24) (79 mg, 0.17 mmol) was solubilized in THF (1 mL) and water (0.31 mL) at 0° C. A solution of 1N LiOH (215 μL, 0.21 mmol) was then dropped. The mixture was stirred for 30 min at 0° C. The reaction mixture was acidified with 0.1N HCl (50 μL) and concentrated to remove THF. The resulting aqueous layer was frozen and lyophilized. The resulting salt was triturated with Et₂O to provide lithium trans-2-[[2-[(tert-butoxycarbonylamino)methyl]-4-oxazol-5-yl-7-oxo-1,6-diazabicyclo[3.2.1]oct-3-en-6-yl]oxy]-2,2-difluoro-acetate (25) (60 mg, 0.14 mmol, 80%) as a white solid.

MS m/z ([M+H]$^+$) 431.

$^1$H NMR (400 MHz, CDCl₃): δ (ppm) 1.39 (s, 9H), 3.19-3.28 (m, 3H), 3.37-3.40 (m, 1H), 3.86-3.91 (m, 1H), 4.52-4.53 (m, 1H), 6.0-6.01 (m, 1H), 7.45 (s, 1H), 8.37 (s, 1H).

Step 4: Preparation of lithium and 2,2,2-trifluoroacetate [trans-2-(azaniumylmethyl)-4-oxazol-5-yl-7-oxo-1,6-diazabicyclo[3.2.1]oct-3-en-6-yl]oxy]-2,2-difluoro-acetate (Example 3)

At 0° C. TFA (6.6 μL) was slowly added to a solution of compound (25) (25 mg, 0.057 mmol) in anhydrous DCM (1 mL). After 2 h at 0° C. an excess of TFA (600 μL) was added. The mixture was stirred at 0° C. for 1 h more and concentrated in vacuo. The residue was dissolved in H₂O (100 μL) and lyophilized to provide lithium and 2,2,2-trifluoroacetate [trans-2-(azaniumylmethyl)-4-oxazol-5-yl-7-oxo-1,6-diazabicyclo[3.2.1]oct-3-en-6-yl]oxy]-2,2-difluoro-acetate (Example 3) (26 mg, 0.057 mmol, 100%).

MS m/z ([M+H]$^+$) 331.

MS m/z ([M−H]$^-$) 329.

$^1$H NMR (400 MHz, DMSO-d₆) δ 3.22-3.63 (m, 4H), 4.17-4.22 (m, 1H), 4.66-4.67 (m, 1H), 6.11-6.12 (m, 1H), 7.33 (s, 1H), 8.06 (bs, 3H), 8.44 (s, 1H).

Example 4

Synthesis of Sodium [trans-2-(methoxymethyl)-4-oxazol-5-yl-1,6-diazabicyclo[3.2.1]oct-3-en-7-one] Sulfate

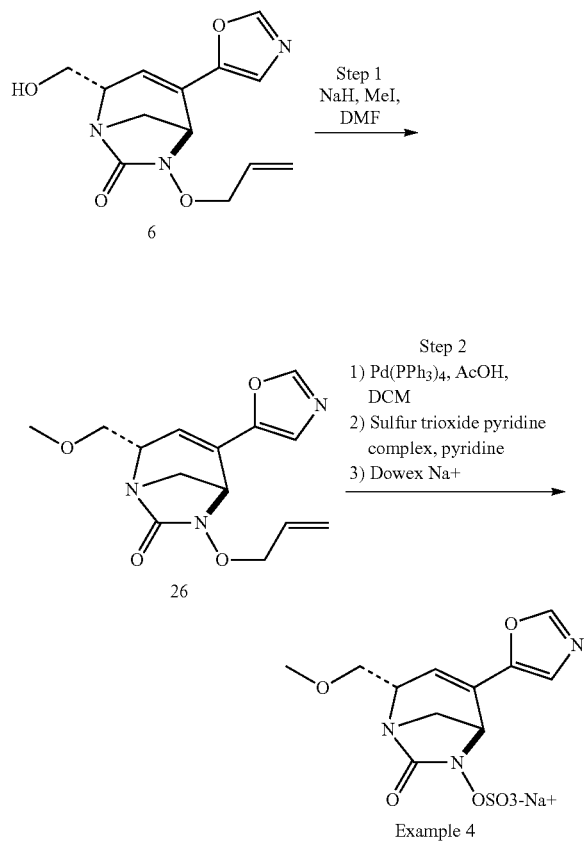

Step 1: Preparation of Intermediate trans-6-allyloxy-2-(methoxymethyl)-4-oxazol-5-yl-1,6-diazabicyclo[3.2.1]oct-3-en-7-one (26)

A solution of trans-6-allyloxy-2-(hydroxymethyl)-4-oxazol-5-yl-1,6-diazabicyclo[3.2.1]oct-3-en-7-one (6) (140 mg, 0.50 mmol) in anhydrous DMF (1.5 mL) was cooled to 0° C. Iodomethane (94 μL, 1.51 mmol) followed by NaH 60% in oil (24 mg, 0.61 mmol) were added and the reaction mixture was stirred at 0° C. for 15 min. Water (2 mL) was added carefully and the mixture was extracted with EtOAc (2×3 mL). The organic layer was dried over $Na_2SO_4$, filtered and concentrated in vacuo. The crude was purified by flash chromatography on silica gel (cyclohexane/EtOAc 100/0 to 20/80) to provide trans-6-allyloxy-2-(methoxymethyl)-4-oxazol-5-yl-1,6-diazabicyclo[3.2.1]oct-3-en-7-one (26) (60 mg, 0.21 mmol, 41%).

MS m/z ([M+H]$^+$) 292.

$^1$H NMR (300 MHz, $CDCl_3$): δ (ppm) 3.36-3.43 (m, 4H), 3.50 (dd, J=11.2, 0.8 Hz, 1H), 3.63-3.75 (m, 2H), 4.11-4.19 (m, 2H), 4.33-4.49 (m, 2H), 5.27-5.39 (m, 2H), 5.91-6.06 (m, 1H), 6.10 (d, J=3.2 Hz, 1H), 7.03 (s, 1H), 7.82 (s, 1H).

Step 2: Preparation of sodium [trans-2-(methoxymethyl)-4-oxazol-5-yl-1,6-diazabicyclo[3.2.1]oct-3-en-7-one] sulfate (example 4)

To a solution of trans-6-allyloxy-2-(methoxymethyl)-4-oxazol-5-yl-1,6-diazabicyclo[3.2.1]oct-3-en-7-one (26) (60 mg, 0.206 mmol) and glacial acetic acid (24 μL, 0.412 mmol) in anhydrous DCM (2.3 mL) was added in one portion Pd(PPh$_3$)$_4$ (119 mg, 0.103 mmo). After stirring for 2 h, a solution of sulfur trioxide pyridine complex (133 mg, 0.834 mmol) in anhydrous pyridine (2.6 mL) was added and the resulting mixture was stirred overnight. The mixture was concentrated in vacuo, diluted with DCM and the precipitate filtered. The filtrate was concentrated in vacuo. The crude was purified by flash chromatography on silica gel (DCM/acetone 100/0 to 0/100). The fractions containing the expected intermediate were combined and concentrated in vacuo. The residue, dissolved in a mixture of $H_2O$/THF 7/3 (0.5 mL), was applied on a Dowex sodium form column (Dowex® 50WX8 hydrogen form stored with an aqueous solution of 2N NaOH and washed until neutral pH with $H_2O$). The fractions containing the desired compound were combined and concentrated in vacuo. The product was dissolved in a minimum amount of water, freezed and lyophilized to afford sodium [trans-2-(methoxymethyl)-4-oxazol-5-yl-1,6-diazabicyclo[3.2.1]oct-3-en-7-one] sulfate (example 4) (18 mg, 0.05 mmol, 24%).

$^1$H NMR (300 MHz, DMSO-d$_6$): δ (ppm) 3.24-3.32 (m, 4H), 3.46 (d, J=11.4 Hz, 1H), 3.57-3.69 (m, 2H), 3.91-3.98 (m, 1H), 4.50-4.54 (m, 1H), 5.99 (d, J=2.9 Hz, 1H), 7.25 (s, 1H), 8.37 (s, 1H).

Example 5

Synthesis of Sodium and 2,2,2-trifluoroacetate [(2S,5R)-2-(azaniumylmethyl)-7-oxo-3-oxazol-2-yl-1,6-diazabicyclo[3.2.1]oct-3-en-6-yl] sulfate

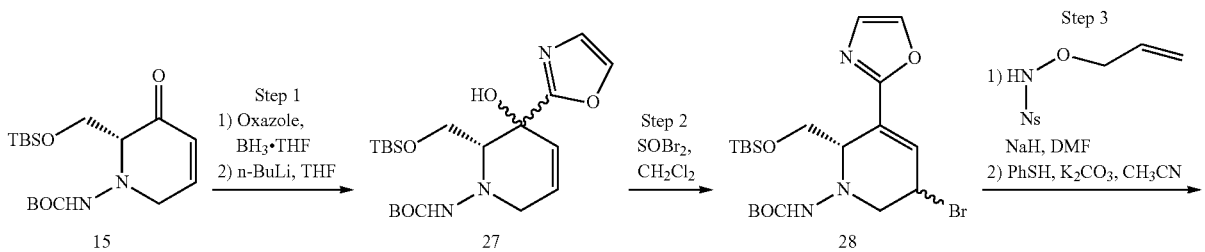

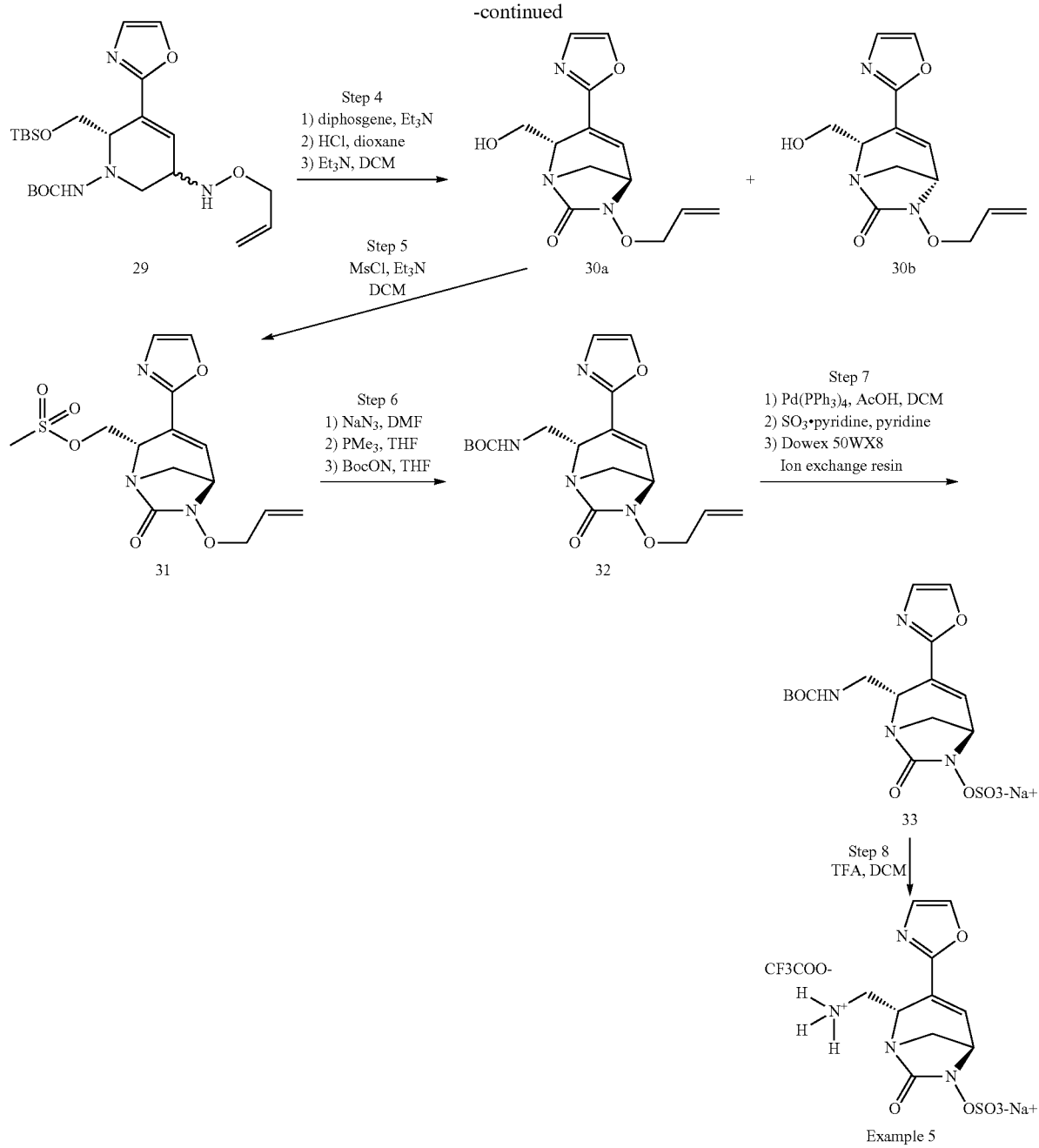

Step 1: Preparation of Intermediate tert-butyl (2R)-2-[[tert-butyl(dimethyl)silyl]oxymethyl]-3-hydroxy-3-oxazol-2-yl-2,6-dihydropyridine-1-carboxylate (27)

To a solution of borane tetrahydrofuran complex solution 1.0 M in THF (19 mL, 19 mmol) under nitrogen atmosphere at rt, was dropwise added oxazole (1.24 mL, 18.89 mmol). The mixture was stirred at rt for 1 h then cooled down to −78° C. A n-butyllithium solution 1.6 M in hexanes (12.2 ml, 19.5 mmol) was dropwise added and the mixture maintained at this temperature for 30 min. A solution of compound (15) (4.30 g, 12.6 mmol) in anhydrous THF (9 mL) was dropwise added. The mixture was stirred at −78° C. for 90 min. Ethanol containing 5% AcOH (30 mL) was added and the mixture was stirred at rt for 18 h. Water (50 mL) was added. The aqueous layer was extracted with EtOAc (2×50 mL). The combined organic layers were washed with a saturated solution of NaHCO$_3$ (50 mL), dried over Na$_2$SO$_4$ and concentrated in vacuo. The residue was purified by flash chromatography on silica gel (cyclohexane/EtOAc: 80/20 to 40/60) to provide compound (27) (1.12 g, 2.72 mmol, 21%) as a cis/trans mixture.

MS m/z ([M+H]$^+$) 411.

1H NMR (400 MHz, CDCl$_3$) δ 0.10 and 0.11 (s, 6H), 0.90 (s, 9H), 1.33 and 1.37 (s, 9H), 3.40-3.78 (m, 2H), 4.00-4.08 (m, 1H), 4.26 and 4.38 (d, J=19.4 Hz, 1H), 4.68 and 4.99 (bs, 1H), 4.88 and 4.74 (t, J=7.2 Hz, 1H), 5.86-6.04 (m, 2H), 7.01 and 7.07 (s, 1H), 7.61 (d, J=0.8 Hz, 1H).

Step 2: Preparation of Intermediate tert-butyl (6S)-3-bromo-6-[[tert-butyl(dimethyl)silyl]oxymethyl]-5-oxazol-2-yl-3,6-dihydro-2H-pyridine-1-carboxylate (28)

Using the procedure described in example 2 (step 8) the intermediate (27) (1.12 g, 2.73 mmol) is converted into intermediate (28) (1.25 g, 2.64 mmol, 96%) as a cis/trans mixture which was used without further purification.

Step 3: Preparation of Intermediate tert-butyl (6S)-3-(allyloxyamino)-6-[[tert-butyl(dimethyl)silyl]oxymethyl]-5-oxazol-2-yl-3,6-dihydro-2H-pyridine-1-carboxylate (29)

Using the procedure described in example 2 (step 9) the intermediate (28) (1.25 g, 2.64 mmol) is converted into intermediate (29) (750 mg, 1.61 mmol, 61%) as a mixture cis/trans (62/38) after purification by flash chromatography on silica gel (DCM/EtOAc from 100/0 to 70/30).

MS m/z ([M+H]$^+$) 466.

Step 4: Preparation of Intermediates (2S,5R)-6-allyloxy-2-(hydroxymethyl)-3-oxazol-2-yl-1,6-diazabicyclo[3.2.1]oct-3-en-7-one (30a) and (2S,5S)-6-allyloxy-2-(hydroxymethyl)-3-oxazol-2-yl-1,6-diazabicyclo[3.2.1]oct-3-en-7-one (30b)

Using the procedure described in example 2 (step 10) the intermediate (29) (750 mg, 1.61 mmol) is converted into intermediate (30a) (88 mg, 0.31 mmol, 20%) and intermediate (30b) (201 mg, 0.72 mmol, 45%) after purification and separation by preparative TLCs on silica gel (EtOAc).

MS m/z ([M+H]$^+$) 278.

30a:
1H NMR (400 MHz, CDCl$_3$) δ 3.33 (s, 2H), 3.51 (bs, 1H), 3.93 (dd, J=11.4, 7.5 Hz, 1H), 4.03-4.08 (m, 1H), 4.22 (dd, J=11.6, 4.7 Hz, 1H), 4.33-4.52 (m, 3H), 5.24-5.40 (m, 2H), 5.92-6.07 (m, 1H), 7.11 (s, 1H), 7.19 (d, J=5.3 Hz, 1H), 7.58 (s, 1H).

30b:
$^1$H NMR (400 MHz, CDCl$_3$) δ 3.19 (dd, J=14.1, 3.3 Hz, 1H), 3.90 (bs, 1H), 4.21 (t, J=8.5 Hz, 1H), 4.32-4.47 (m, 3H), 4.86-4.98 (m, 1H), 5.04 (t, J=9.0 Hz, 1H), 5.30 (dd, J=10.4, 1.0 Hz, 1H), 5.35-5.45 (m, 1H), 5.55 (s, 1H), 5.99-6.09 (m, 1H), 6.86 (d, J=5.9 Hz, 1H), 7.26 (d, J=0.8 Hz, 1H), 7.76 (d, J=0.8 Hz, 1H).

Step 5: Preparation of Intermediate [(2S,5R)-6-allyloxy-7-oxo-3-oxazol-2-yl-1,6-diazabicyclo[3.2.1]oct-3-en-2-yl]methyl methanesulfonate (31)

Using the procedure described in example 2 (step 11) the intermediate (30a) (119 mg, 0.43 mmol) is converted into intermediate (31) (153 mg, 0.43 mmol, 100%) as a yellow oil which was used without further purification.

MS m/z ([M+H]$^+$) 356.
1H NMR (400 MHz, CDCl$_3$) δ 3.05 (s, 3H), 3.40 (ddd, J=11.5, 2.7, 1.3 Hz, 1H), 3.48 (dd, J=11.5, 0.8 Hz, 1H), 4.07 (dd, J=5.2, 1.9 Hz, 1H), 4.35-4.50 (m, 2H), 4.66 (ddd, J=6.4, 3.9, 1.8 Hz, 1H), 4.85-4.89 (m, 2H), 5.29-5.41 (m, 2H), 5.95-6.07 (m, 1H), 7.14 (d, J=0.8 Hz, 1H), 7.27 (dt, J=5.2, 1.4 Hz, 1H), 7.59 (d, J=0.8 Hz, 1H).

Step 6: Preparation of Intermediate tert-butyl N-[[(2S,5R)-6-allyloxy-7-oxo-3-oxazol-2-yl-1,6-diazabicyclo[3.2.1]oct-3-en-2-yl]methyl]carbamate (32)

Using the procedure described in example 2 (step 12) the intermediate (31) (153 mg, 0.43 mmol) is converted into intermediate (32) (57 mg, 0.15 mmol, 35%) after purification by flash chromatography on silica gel (cyclohexane/EtOAc from 70/30 to 0/100) then by preparative TLCs on silica gel (cyclohexane/acetone 60/40).

MS m/z ([M+H]$^+$) 377.
$^1$H NMR (400 MHz, CDCl$_3$) δ 1.43 (s, 9H), 3.19-3.37 (m, 3H), 3.97-4.10 (m, 2H), 4.32-4.49 (m, 3H), 5.15 (bs, 1H), 5.24-5.40 (m, 2H), 5.89-6.07 (m, 1H), 7.11 (s, 1H), 7.16 (d, J=4.9, 1H), 7.56 (s, 1H).

Step 7: Preparation of Intermediate sodium [(2S,5R)-2-[(tert-butoxycarbonylamino)methyl]-7-oxo-3-oxazol-2-yl-1,6-diazabicyclo[3.2.1]oct-3-en-6-yl] sulfate (33)

Using the procedure described in example 2 (step 13) the intermediate (32) (57 mg, 0.15 mmol) is converted into intermediate (33) (28 mg, 0.064 mmol, 42%).

MS m/z ([M+H]$^+$) 417.
MS m/z ([M−H]$^−$) 415.
$^1$H NMR (400 MHz, D$_2$O) δ 1.43 (s, 9H), 3.41-3.58 (m, 2H), 3.64 (d, J=11.9 Hz, 1H), 3.74 (dd, J=14.8, 3.2 Hz, 1H), 4.40 (dd, J=9.9, 3.7 Hz, 1H), 4.53 (dd, J=5.3, 2.5 Hz, 1H), 7.22 (s, 1H), 7.27 (d, J=5.2 Hz, 1H), 7.85 (s, 1H).

Step 8: Preparation of Sodium and 2,2,2-trifluoroacetate [(2S,5R)-2-(azaniumylmethyl)-7-oxo-3-oxazol-2-yl-1,6-diazabicyclo[3.2.1]oct-3-en-6-yl] sulfate (Example 5)

Using the procedure described in example 2 (step 14) the intermediate (33) (28 mg, 0.064 mmol) is converted into Example 5 (22.8 mg, 0.050 mmol, 78%) as an off white solid.

MS m/z ([M+H]$^+$) 317.
MS m/z ([M−H]$^−$) 315.
$^1$H NMR (300 MHz, D$_2$O) δ 3.41 (dd, J=13.5, 11.9 Hz, 1H), 3.57 (d, J=1.6 Hz, 2H), 3.79 (dd, J=13.8, 3.9 Hz, 1H), 4.54-4.66 (m, 2H), 7.24 (d, J=0.9 Hz, 1H), 7.37 (dd, J=5.3, 1.6 Hz, 1H), 7.86 (d, J=0.9 Hz, 1H).

Example 6

Synthesis of [trans-2-(aminomethyl)-4-(1-methylpyrimidin-2(1H)-one-5-yl)-7-oxo-1,6-diazabicyclo[3.2.1]oct-3-en-6-yl] hydrogen sulfate

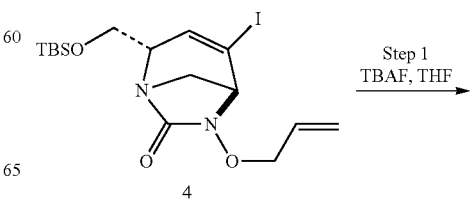

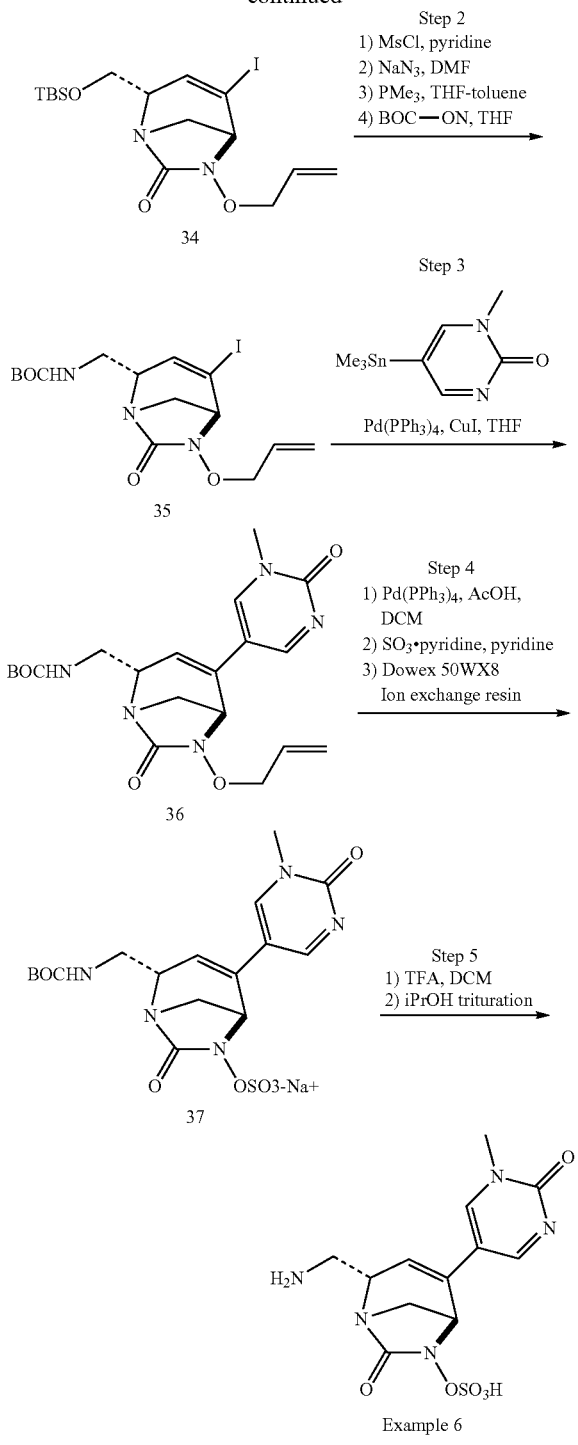

Step 1: Preparation of Intermediate trans-6-allyloxy-2-(hydroxymethyl)-4-iodo-1,6-diazabicyclo[3.2.1]oct-3-en-7-one (34)

Using the procedure described in example 1 (step 5) the intermediate (4) (514 mg, 1.14 mmol) is converted into intermediate (34) (384 mg, 1.14 mmol, quantitative yield) as a brown oil which was used without further purification.

MS m/z ([M+H]$^+$) 337.

Step 2: Preparation of Intermediate tert-butyl N-[[trans-6-allyloxy-4-iodo-7-oxo-1,6-diazabicyclo[3.2.1]oct-3-en-2-yl]methyl]carbamate (35)

A solution of trans-6-allyloxy-2-(hydroxymethyl)-4-iodo-1,6-diazabicyclo[3.2.1]oct-3-en-7-one (34) (384 mg, 1.14 mmol) in DCM (11 mL) was cooled to 0° C. TEA (0.95 mL, 6.85 mmol) and MsCl (0.44 mL, 5.71 mmol) were added and the reaction mixture was stirred at the same temperature for 1 h. After completion, the reacting mixture was concentrated in vacuo. The crude was dissolved in DMF (11 mL) and NaN$_3$ (371 mg, 5.71 mmol) was added. The reaction mixture was heated at 65° C. overnight and concentrated in vacuo. The crude was dissolved in a mixture of THF and toluene (3.8 mL/3.8 mL) and PMe$_3$ (1M in tetrahydrofuran) (1.71 mL, 1.71 mmol) was added at 0° C. After 1 h stirring at rt, the mixture was cooled to 0° C. and a solution of BocON (422 mg, 1.71 mmol) in THF (3.8 mL) was dropwise added. The mixture was stirred overnight at rt and concentrated in vacuo. The crude was purified by flash chromatography on silica gel (DCM/Acetone from 95/5 to 0/100) to give tert-butyl N-[[trans-6-allyloxy-4-iodo-7-oxo-1,6-diazabicyclo[3.2.1]oct-3-en-2-yl]methyl]carbamate (35) (43 mg, 0.10 mmol, 10% over 4 steps).

MS m/z ([M+H]$^+$) 436.

$^1$H NMR (400 MHz, CDCl$_3$): δ (ppm) 1.42 (s, 9H), 3.17-3.20 (m, 1H), 3.26-3.31 (m, 1H), 3.45-3.51 (m, 1H), 3.85-3.88 (m, 1H), 4.09 (d, J=2.0 Hz, 1H), 4.37-4.50 (m, 3H), 5.76-5.86 (m, 1H), 5.98-6.08 (m, 2H), 6.26 (d, J=2.0 Hz, 1H), 6.98 (bs, 1H).

Step 3: Preparation of Intermediate tert-butyl N-[[trans-6-allyloxy-4-(1-methylpyrimidin-2(1H)-one-5-yl)-7-oxo-1,6-diazabicyclo[3.2.1]oct-3-en-2-yl]methyl]carbamate (36)

In a sealed flask, a mixture of tert-butyl N-[[trans-6-allyloxy-4-iodo-7-oxo-1,6-diazabicyclo[3.2.1]oct-3-en-2-yl]methyl]carbamate (35) (43 mg, 0.10 mmol) and 5-trimethyltin-1-methylpyrimidin-2(1H)-one (32 mg, 0.12 mmol) in anhydrous THF (1.0 mL) was degassed under argon for 5 min before Pd(PPh$_3$)$_4$ (6 mg, 0.005 mmol) and CuI (2 mg, 0.01 mmol) were added. The mixture was heated at 60° C. overnight. After completion, the reacting mixture was concentrated in vacuo. The crude was purified by flash chromatography on silica gel (DCM/Acetone from 70/30 to 0/100) to give tert-butyl N-[[trans-6-allyloxy-4-(1-methylpyrimidin-2(1H)-one-5-yl)-7-oxo-1,6-diazabicyclo[3.2.1]oct-3-en-2-yl]methyl]carbamate (36) (12 mg, 0.03 mmol, 29%).

MS m/z ([M+H]$^+$) 418.

$^1$H NMR (400 MHz, (CD$_3$)$_2$CO): δ (ppm) 1.41 (s, 9H), 3.25-3.41 (m, 2H), 3.52 (s, 3H), 3.84-3.93 (m, 2H), 4.49-4.52 (m, 1H), 5.25 (d, J=10.4 Hz, 1H), 5.38 (dd, J=17.2, 1.2 Hz, 1H), 5.96 (d, J=2.0 Hz, 1H), 5.99-6.09 (m, 2H), 6.20-6.24 (m, 1H), 6.38 (dd, J=6.4, 4.0 Hz, 1H), 8.14 (dd, J=6.4, 2.8 Hz, 1H), 8.53 (d, J=2.8 Hz, 1H).

Step 4: Preparation of Intermediate sodium [trans-2-[(tert-butoxycarbonylamino)methyl]-4-(1-methyl-pyrimidin-2(1H)-one-5-yl)-7-oxo-1,6-diazabicyclo [3.2.1]oct-3-en-6-yl] sulfate (37)

To a solution of tert-butyl N-[[trans-6-allyloxy-4-(1-methylpyrimidin-2(1H)-one-5-yl)-7-oxo-1,6-diazabicyclo [3.2.1]oct-3-en-2-yl]methyl]carbamate (36) (12 mg, 0.03 mmol) and glacial AcOH (3 μL, 0.06 mmol) in anhydrous DCM (0.14 mL) was added in one portion Pd(PPh3)4 (17 mg, 0.014 mmol). After stirring for 2 h, a solution of sulfur trioxide pyridine complex (23 mg, 0.14 mmol) in dry pyridine (0.14 mL) was added and the resulting mixture was stirred overnight at 40° C. in the dark. The reaction mixture was concentrated in vacuo, diluted with DCM and filtered. The filtrate was concentrated in vacuo. The crude was dissolved in a mixture of H2O/MeCN 7/3 (1 mL) was applied on a Dowex sodium form column (Dowex® 50WX8 hydrogen form stored with an aqueous solution of 2N NaOH and washed until neutral pH with H2O). The fractions containing the desired compound were combined and concentrated in vacuo to give sodium [trans-2-[(tert-butoxycarbonylamino)methyl]-4-(1-methylpyrimidin-2(1H)-one-5-yl)-7-oxo-1,6-diazabicyclo[3.2.1]oct-3-en-6-yl] sulfate (37) (15 mg).

MS m/z ([M+H]+) 458.
MS m/z ([M−H]−) 456.

Step 5: Preparation of [trans-2-(aminomethyl)-4-(1-methylpyrimidin-2(1H)-one-5-yl)-7-oxo-1,6-diazabicyclo[3.2.1]oct-3-en-6-yl] hydrogen sulfate (Example 6)

The crude sodium [trans-2-[(tert-butoxycarbonylamino)methyl]-4-(1-methylpyrimidin-2(1H)-one-5-yl)-7-oxo-1,6-diazabicyclo[3.2.1]oct-3-en-6-yl] sulfate (37) (14 mg, 0.03 mmol) was dissolved in DCM (1.0 mL), cooled to 0° C., and a pre-cooled solution of TFA (0.67 mL, 8.76 mmol) in DCM (0.67 mL) was dropwise added. After 1 h stirring at the same temperature, the reaction mixture was poured into DCM and concentrated in vacuo (co-evaporations with DCM). The solid residue was washed with DCM twice, solubilized into water, filtered through Isodisc® and lyophilized to afford the crude sodium and 2,2,2-trifluoroacetate [trans-2-(azanium-ylmethyl)-4-(1-methylpyrimidin-2(1H)-one-5-yl)-7-oxo-1,6-diazabicyclo[3.2.1]oct-3-en-6-yl] sulfate. The crude sodium and 2,2,2-trifluoroacetate [trans-2-(azaniumylmethyl)-4-(1-methylpyrimidin-2(1H)-one-5-yl)-7-oxo-1,6-diazabicyclo[3.2.1]oct-3-en-6-yl] sulfate (7.1 mg, 0.014 mmol) was then triturated 3 times in propan-2-ol and dried under reduced pressure to afford [trans-2-(aminomethyl)-4-(1-methylpyrimidin-2(1H)-one-5-yl)-7-oxo-1,6-diazabicyclo [3.2.1]oct-3-en-6-yl] sulfate (Example 6) (5.2 mg, 0.01 mmol, 35% over 4 steps).

MS m/z ([M+H]+) 358.
MS m/z ([M−H]−) 356.
1H NMR (400 MHz, D2O): δ (ppm) 3.27-3.43 (m, 2H), 3.52 (d, J=11.6 Hz, 1H), 3.59 (dd, J=11.6, 2.8 Hz, 1H), 3.60 (s, 3H), 4.22-4.27 (ddd, J=11.6, 3.2, 2.8 Hz, 1H), 4.67 (d, J=2.8 Hz, 1H), 5.99 (d, J=2.8 Hz, 1H), 8.23 (d, J=3.2 Hz, 1H), 8.72 (d, J=3.2 Hz, 1H).

Example 7

Synthesis of [(2S,5R)-2-(quanidinomethyl)-7-oxo-3-thiazol-2-yl-1,6-diazabicyclo [3.2.1]oct-3-en-6-yl] hydrogen sulfate

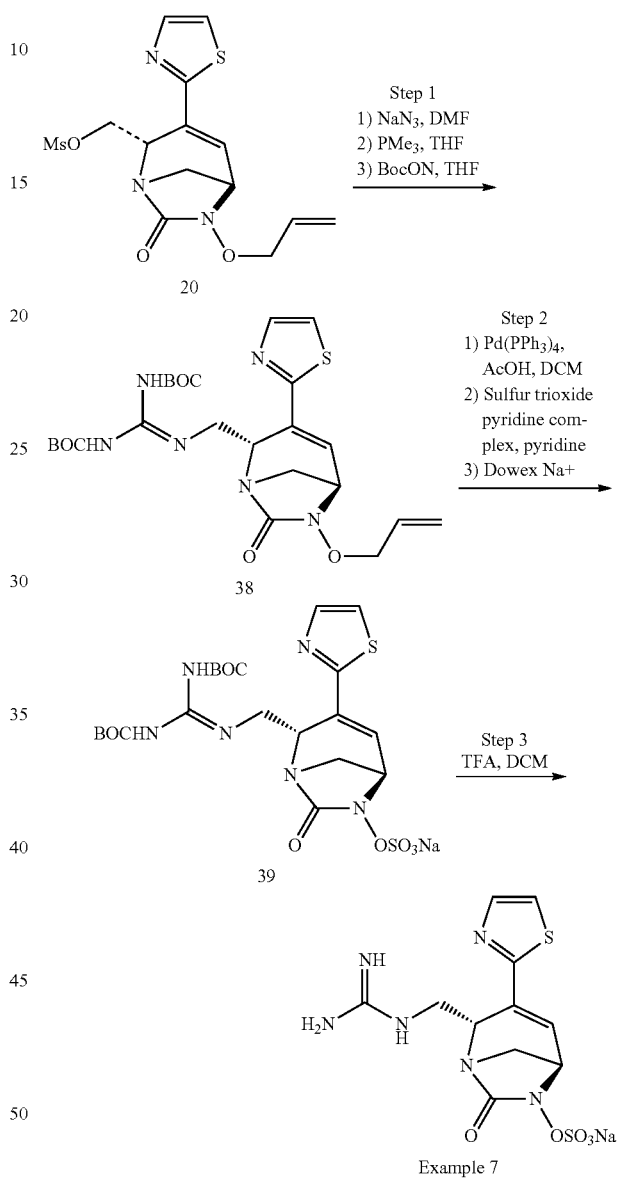

Example 7

Step 1: Preparation of Intermediate tert-butyl N—[N'-[[(2S,5R)-6-allyloxy-7-oxo-3-thiazol-2-yl-1,6-diazabicyclo[3.2.1]oct-3-en-2-yl]methyl]-N-tert-butoxycarbonyl-carbamimidoyl]carbamate (38)

A mixture of compound (20) (150 mg, 0.404 mmol) and NaN3 (131 mg, 2.02 mmol) in anhydrous DMF (2.0 mL) was stirred at 65° C. for 24 h. The mixture was poured in H2O (5 mL) and extracted with EtOAc (2×5 mL). The organic layer was washed with brine (5 mL), dried over Na2SO4 and concentrated in vacuo. The residue was dissolved in anhydrous THF (1 mL) and anhydrous toluene (1 mL) and cooled at 0° C. under nitrogen atmosphere. A PMe₃ solution 1M in THF (0.52 mL, 0.518 mmol) was dropwise added and the mixture was stirred at rt for 1 h. The mixture was cooled at 0° C. and a solution of BocON (161 mg, 0.518 mmol) in anhydrous THF (0.7 mL) was added. The mixture was stirred at rt for 1 h. Water (5 mL) was added and the layers separated. The aqueous layer was extracted with EtOAc (2×5 mL). The combined organic layers were washed with brine (5 mL), dried over Na₂SO₄ and concentrated in vacuo. The residue was purified by flash chromatography on silica gel (cyclohexane/EtOAc: 95/5 to 0/100) to provide tert-butyl N—[N'-[[(2S,5R)-6-allyloxy-7-oxo-3-thiazol-2-yl-1,6-diazabicyclo[3.2.1]oct-3-en-2-yl]methyl]-N-tert-butoxycarbonyl-carbamimidoyl]carbamate (38) (40 mg, 0.075 mmol, 22%) as a white solid.

MS m/z ([M+H]⁺) 535.

¹H NMR (400 MHz, CDCl₃) δ 1.47 (s, 9H), 1.50 (s, 9H), 3.29-3.36 (m, 1H), 3.40 (d, J=11.4 Hz, 1H), 3.65 (ddd, J=14.1, 11.4, 4.3 Hz, 1H), 4.02 (dd, J=5.0, 2.3 Hz, 1H), 4.19 (dt, J=14.2, 4.8 Hz, 1H), 4.35-4.48 (m, 2H), 4.76 (ddd, J=11.4, 4.3, 1.3 Hz, 1H), 5.27-5.38 (m, 2H), 5.95-6.08 (m, 1H), 6.96 (d, J=5.1 Hz, 1H), 7.21 (d, J=3.2 Hz, 1H), 7.74 (d, J=3.2 Hz, 1H), 8.80 (s, 1H), 11.43 (s, 1H).

Step 2: Preparation of Intermediate sodium [(2S,5R)-2-[[bis(tert-butoxycarbonylamino)methyleneamino]methyl]-7-oxo-3-thiazol-2-yl-1,6-diazabicyclo[3.2.1]oct-3-en-6-yl] sulfate (39)

To a solution of tert-butyl N—[N'-[[(2S,5R)-6-allyloxy-7-oxo-3-thiazol-2-yl-1,6-diazabicyclo[3.2.1]oct-3-en-2-yl]methyl]-N-tert-butoxycarbonyl-carbamimidoyl]carbamate (38) (40 mg, 0.075 mmol) and glacial AcOH (9 µL, 0.150 mmol) in anhydrous DCM (0.3 mL) was added in one portion Pd(PPh₃)₄ (43 mg, 0.037 mmo). The mixture was stirred at rt for 1 h then concentrated in vacuo. The residue was purified by flash chromatography on silica gel (DCM/acetone: 100/0 to 0/100) to provide a mixture of expected intermediate and triphenylphosphine oxide. The mixture was dissolved in pyridine (0.55 mL) and sulfur trioxide pyridine complex (131 mg, 0.823 mmol) was added. The mixture was stirred at rt overnight then concentrated in vacuo. DCM (2 mL) was added to the residue and the precipitate filtered. The filtrate was concentrated and the residue purified by flash chromatography on silica gel (DCM/acetone: 50/50 to 0/100). The fractions containing the expected intermediate were combined and concentrated in vacuo. The residue was dissolved in a mixture of H₂O/THF 7/3 (0.5 mL), and converted after ion exchange (Dowex sodium form column) to sodium [(2S,5R)-2-[[bis(tert-butoxycarbonylamino)methyleneamino]methyl]-7-oxo-3-thiazol-2-yl-1,6-diazabicyclo[3.2.1]oct-3-en-6-yl] sulfate (39) (12 mg, 0.020 mmol, 28%).

MS m/z ([M+H]⁺) 575.

MS m/z ([M-H]⁻) 573.

Step 3: Preparation of [(2S,5R)-2-(guanidinommethyl)-7-oxo-3-thiazol-2-yl-1,6-diazabicyclo[3.2.1]oct-3-en-6-yl] hydrogen sulfate (Example 7)

A solution of sodium [(2S,5R)-2-[[bis(tert-butoxycarbonylamino)methyleneamino]methyl]-7-oxo-3-thiazol-2-yl-1,6-diazabicyclo[3.2.1]oct-3-en-6-yl] sulfate (39) (12 mg, 0.020 mmol) in anhydrous DCM (0.25 mL) was added to a mixture of DCM (0.45 mL) and TFA (0.45 mL) at 00° C. The mixture was stirred at 0° C. for 30 min and allowed to reach rt for 1 h. TFA (0.3 mL) was added and the mixture was stirred at rt for a further 3 h, then concentrated in vacuo. The residue was co-evaporated three times with DCM (2 mL). Water (0.5 mL) was added and the precipitate was filtered to provide [(2S,5R)-2-(guanidinommethyl)-7-oxo-3-thiazol-2-yl-1,6-diazabicyclo[3.2.1]oct-3-en-6-yl] hydrogen sulfate (Example 7) (3.2 mg, 0.006 mmol, 42%) as a light pink solid.

MS m/z ([M+H]⁺) 375.

MS m/z ([M-H]⁻) 373.

¹H NMR (300 MHz, DMSO) δ 3.21-3.31 (m, 1H), 3.43-3.58 (m, 2H), 3.68-3.80 (m, 1H), 4.28-4.36 (m, 1H), 4.39 (dd, J=5.3, 2.4 Hz, 1H), 7.21 (d, J=5.3 Hz, 1H), 7.79 (d, J=3.2 Hz, 1H), 7.75-7.82 (m, 2H).

Example 8

Synthesis of Sodium and 2,2,2-trifluoroacetate disalt of [(2S,5R)-2-[(3-aminopropanoylamino)methyl]-7-oxo-3-thiazol-2-yl-1,6-diazabicyclo[3.2.1]oct-3-en-6-yl]sulfate

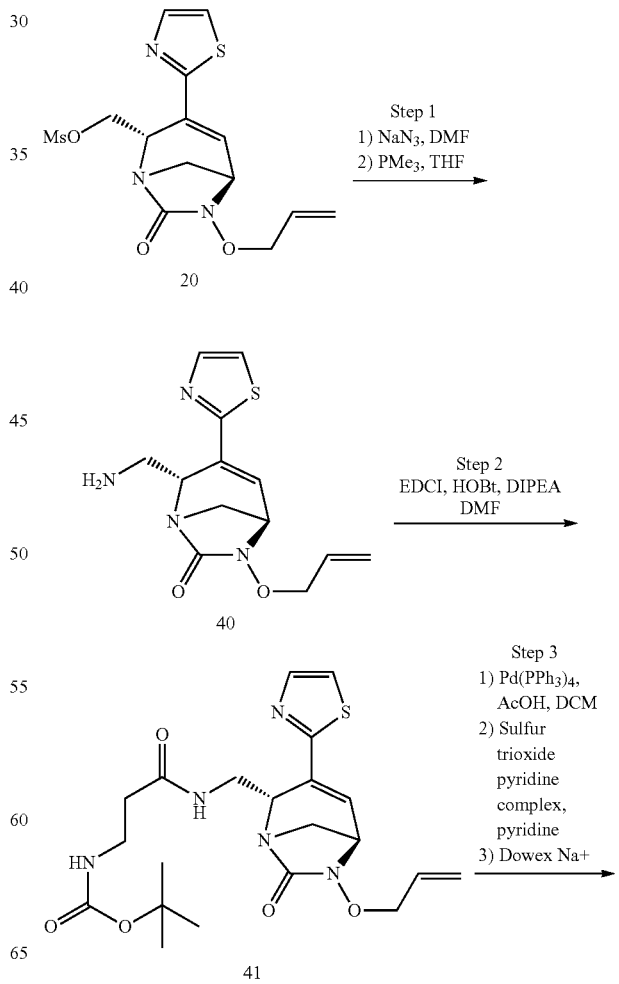

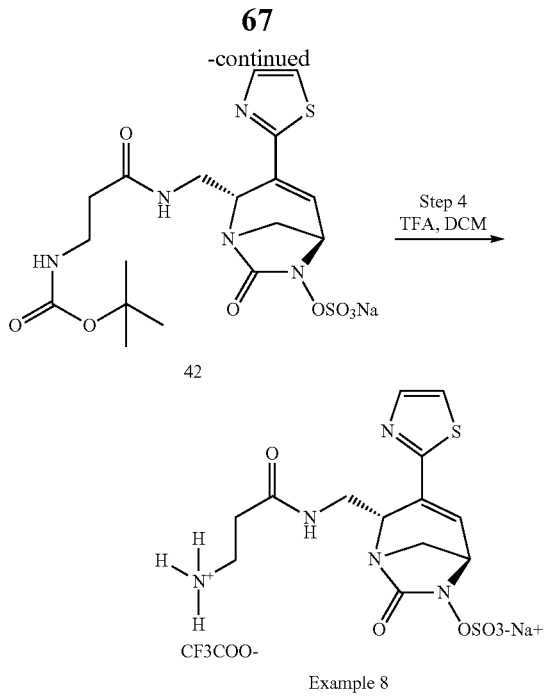

Example 8

Step 1: Preparation of Intermediate (2S,5R)-6-allyloxy-2-(aminomethyl)-3-thiazol-2-yl-1,6-diazabicyclo[3.2.1]oct-3-en-7-one (40)

A mixture of compound (20) (253 mg, 0.68 mmol) and NaN$_3$ (221 mg, 3.41 mmol) in anhydrous DMF (3.0 mL) was stirred at 65° C. for 24 h. The mixture was poured in H$_2$O (5 mL) and extracted with EtOAc (2×5 mL). The organic layer was washed with brine (5 mL), dried over Na$_2$SO$_4$ and concentrated in vacuo. The residue was dissolved in anhydrous THF (2 mL) and anhydrous toluene (2 mL) and cooled at 0° C. under nitrogen atmosphere. A PMe$_3$ solution 1M in THF (1.02 mL, 1.02 mmol) was dropwise added, the mixture was stirred at rt for 1 h and concentrated in vacuo. The residue was purified by flash chromatography on silica gel (DCM/iPrOH: 100/0 to 50/50) to provide (2S,5R)-6-allyloxy-2-(aminomethyl)-3-thiazol-2-yl-1,6-diazabicyclo[3.2.1]oct-3-en-7-one (40) (100 mg, 0.34 mmol, 50%).

MS m/z ([M+H]$^+$) 293.

$^1$H NMR (400 MHz, CDCl$_3$) δ 2.81 (dd, J=14.1, 10.3 Hz, 1H), 3.31 (s, 2H), 3.44 (dd, J=14.1, 3.5 Hz, 1H), 3.98-4.04 (m, 1H), 4.37-4.49 (m, 3H), 5.27-5.32 (m, 2H), 5.33-5.39 (m, 1H), 5.95-6.08 (m, 1H), 6.93 (d, J=5.2 Hz, 1H), 7.24 (d, J=3.3 Hz, 1H), 7.75 (d, J=3.3 Hz, 1H).

Step 2: Preparation of Intermediate tert-butyl N-[3-[[(2S,5R)-6-allyloxy-7-oxo-3-thiazol-2-yl-1,6-diazabicyclo[3.2.1]oct-3-en-2-yl]methylamino]-3-oxo-propyl]carbamate (41)

To a solution of N-Boc-β-alanine (78 mg, 0.410 mmol) in anhydrous DMF (2 mL) at 0° C. under inert atmosphere was added HOBt hydrate (63 mg, 0.410 mmol), EDCI (72 mg, 0.376 mmol) and DIPEA (0.12 mL, 0.684 mmol). The mixture was stirred for 30 min at this temperature and a solution of compound (40) (100 mg, 0.342 mmol) in anhydrous DMF (2 mL) was added. The reaction mixture is allowed to reach rt and stirred for 1 hour. H$_2$O was added and the mixture was extracted with EtOAc. The organic layer was washed with brine (5 mL), dried over Na$_2$SO$_4$, filtered and evaporated in vacuo. The crude was purified by flash chromatography on silica gel (DCM/EtOAc 100/0 to 0/100) to provide tert-butyl N-[3-[[(2S,5R)-6-allyloxy-7-oxo-3-thiazol-2-yl-1,6-diazabicyclo[3.2.1]oct-3-en-2-yl]methylamino]-3-oxo-propyl]carbamate (41) (95 mg, 0.205 mmol, 60%).

MS m/z ([M+H]$^+$) 464.

$^1$H NMR (400 MHz, CDCl$_3$) δ 1.43 (s, 9H), 2.42 (t, J=6.0 Hz, 2H), 5.30 (dd, J=11.3, 1.5 Hz, 1H), 3.36 (d, J=11.3 Hz, 1H), 3.39-3.48 (m, 3H), 4.04 (dd, J=5.3, 2.4 Hz, 1H), 4.10-4.20 (m, 1H), 4.36-4.49 (m, 2H), 4.62 (ddd, J=11.0, 4.5, 1.4 Hz, 1H), 5.25 (bs, 1H), 5.31 (dd, J=10.3, 1.4 Hz, 1H), 5.36 (dd, J=17.0, 1.4 Hz, 1H), 5.96-6.06 (m, 1H), 6.17 (bs, 1H), 6.98 (d, J=5.2 Hz, 1H), 7.24 (d, J=3.3 Hz, 1H), 7.75 (d, J=3.3 Hz, 1H).

Step 3: Preparation of Intermediate sodium [(2S,5R)-2-[[3-(tert-butoxycarbonylamino)propanoylamino]methyl]-7-oxo-3-thiazol-2-yl-1,6-diazabicyclo[3.2.1]oct-3-en-6-yl] sulfate (42)

To a solution of compound (41) (85 mg, 0.183 mmol) in anhydrous DCM (1.85 mL) under nitrogen atmosphere were successively added AcOH (21 µL, 0.367 mmol) and Pd(PPh$_3$)$_4$ (106 mg, 0.091 mmol). After stirring for 2 h, dry pyridine (1.85 mL) and sulfur trioxide pyridine complex (145 mg, 0.915 mmol) were added and the resulting mixture was stirred for 2 hours. The reaction mixture was concentrated in vacuo, diluted with DCM (2 mL) and filtered. The filtrate was concentrated in vacuo. The crude was purified by flash chromatography on silica gel (DCM/acetone: 100/0 to 0/100). The fractions containing the expected intermediate were combined and concentrated in vacuo. The residue was dissolved in H$_2$O (1 mL) and converted after ion exchange (Dowex sodium form column), and a chromatography on reverse phase C-18 (water/ACN: 100/0 to 0/100) to sodium [(2S,5R)-2-[[3-(tert-butoxycarbonylamino)propanoylamino]methyl]-7-oxo-3-thiazol-2-yl-1,6-diazabicyclo[3.2.1]oct-3-en-6-yl] sulfate (42) (20 mg, 0.038 mmol, 21%) as a white solid.

MS m/z ([M−H]$^−$) 502.

$^1$H NMR (400 MHz, D$_2$O) δ 1.41 (s, 9H), 2.42 (t, J=6.4 Hz, 2H), 3.29-3.40 (m, 2H), 3.45-3.53 (m, 1H), 3.57-3.68 (m, 2H), 3.75 (dd, J=14.6, 4.5 Hz, 1H), 4.51 (dd, J=5.3, 2.5 Hz, 1H), 4.60 (ddd, J=10.4, 4.5, 1.4 Hz, 1H), 7.11 (d, J=5.3 Hz, 1H), 7.57 (d, J=3.3 Hz, 1H), 7.82 (d, J=3.3 Hz, 1H).

Step 4: Preparation of Intermediate sodium and 2,2,2-trifluoroacetate disalt of [(2S,5R)-2-[(3-aminopropanoylamino)methyl]-7-oxo-3-thiazol-2-yl-1,6-diazabicyclo[3.2.1]oct-3-en-6-yl] sulfate (example 8)

Using the procedure described in example 2 (step 14) the intermediate (42) (17 mg, 0.032 mmol) is converted into Example 8 (16.1 mg, 0.030 mmol, 93%).

MS m/z ([M+H]$^+$) 404.

MS m/z ([M−H]$^−$) 402.

$^1$H NMR (300 MHz, D$_2$O) δ 2.69 (d, J=6.7 Hz, 2H), 3.26 (d, J=6.7 Hz, 2H), 3.44-3.67 (m, 3H), 3.72 (dd, J=14.7, 4.1 Hz, 1H), 4.50-4.58 (m, 1H), 7.14-7.19 (m, 1H), 7.66 (d, J=3.5 Hz, 1H), 7.87 (d, J=3.5 Hz, 1H).

Example 9

Biological Activity

Method 1: β-lactamase inhibitory activity, determination of $IC_{50}$ (table 1)

Enzyme activity was monitored by spectrophotometric measurement of nitrocefin (NCF-TOKU-E, N005) hydrolysis at 485 nm, at room temperature and in assay buffer A: 100 mM Phosphate pH7, 2% glycerol and 0.1 mg/mL Bovine serum albumin (Sigma, B4287). Enzymes were cloned in E. coli expression vector, expressed and purified in house using classical procedures. To a transparent polystyrene plate (Corning, 3628) were added in each well 5 µL DMSO or inhibitor dilutions in DMSO and 80 µL enzyme in buffer A. Plates were immediately read at 485 nm in a microplate spectrophotometer (BioTek, PowerWave HT) to enable background subtraction. After 30 min of pre-incubation at room temperature, 15 µL of NCF (200 µM final) were finally added in each well. Final enzyme concentrations were 0.1 nM (TEM-1), 0.075 nM (SHV-1), 0.4 nM (CTX-M-15), nM (KPC-2), 0.2 nM (P99 AmpC), 0.2 nM (CMY-37), 0.4 nM (AmpC P. aeruginosa), 0.2 nM (OXA-1), 1.2 nM (OXA-11), 0.4 nM (OXA-15) and 0.3 nM (OXA-48). After 20 min incubation at room temperature, plates were once again read at 485 nm. Enzyme activity was obtained by subtracting the final signal by the background, and was converted to enzyme inhibition using non inhibited wells. $IC_{50}$ curves were fitted to a classical Langmuir equilibrium model with Hill slope using XLFIT (IDBS).

Method 2: MIC of Compounds and Synergy with Ceftazidime Against Bacterial Isolates (Tables 2-4)

Compounds of the present invention were assessed against genotyped bacterial strains alone or in combination with the β-lactam ceftazidime. In the assays, MICs of said compounds, or of ceftazidime at fixed concentrations of said compounds were determined by the broth microdilution method according to the Clinical Laboratory Standards Institute (CLSI—M7-A7). Briefly, compounds alone according to the invention were prepared in DMSO and spotted (2 µL each) on sterile polystyrene plates (Corning, 3788). Compounds and ceftazidime dilutions were prepared in DMSO and spotted (1 µL each) on sterile polystyrene plates (Corning, 3788). Log phase bacterial suspensions were adjusted to a final density of $5\times10^5$ cfu/mL in cation-adjusted Mueller-Hinton broth (Becton-Dickinson) and added to each well (98 µL). Microplates were incubated for 16-20 h at 35° C. in ambient air. The MIC of the compounds was defined as the lowest concentration of said compounds that prevented bacterial growth as read by visual inspection.

The MIC of ceftazidime at each compound concentration was defined as the lowest concentration of ceftazidime that prevented bacterial growth as read by visual inspection.

TABLE 2

Bacterial species used in MIC determination

| Strain | | Resistance mechanism |
|---|---|---|
| E. cloacae | 260508 | TEM-1, CTX-M-15 |
| E. coli | UFR61O | TEM-1, KPC-2 |
| K. pneumoniae | BAA-1898 | TEM-1, SHV-11, SHV-12, KPC-2 |
| K. pneumoniae | 160143 | TEM-1, SHV-1, CTX-M-15, KPC-2, OXA-1 |
| K. pneumoniae | UFR68 | TEM-1, SHV-11, CTX-M-15, KPC-3 |
| E. cloacae | P99 | Derepressed ampC |
| E. cloacae | UFR85 | TEM-1, CTX-M-15, derepressed ampC |
| E. cloacae | UFR70 | TEM-1, CTX-M-15, CMY-2, OXA-1, Porin loss |
| K. pneumoniae | UFR77 | CMY-2 |
| E. coli | UFR74 | SHV-1, DHA-1 |
| E. coli | UFR18 | CTX-M-15, OXA-204 |
| E. coli | 131119 | TEM-1, OXA-48 |
| K. oxytoca | UFR21 | TEM-1, CTX-M-15, OXA-48 |
| K. pneumoniae | UFR24 | TEM-1, SHV-2, SHV-11, OXA-1, OXA-48, OXA-47 |
| K. pneumoniae | 6299 | TEM-1, SHV-11, OXA-163 |
| E. coli | RGN238 | OXA-1 |
| K. pneumoniae | 200047 | TEM-1, SHV-32, CTX-M-15, OXA-1 |
| E. coli | 190317 | TEM-1, SHV-12, CTX-M-15, OXA-1 |
| E. coli | UFR32 | TEM-1, VEB-1, OXA-10 |
| E. cloacae | UFR38 | CTX-M-15, NDM-1 |

TABLE 1

$IC_{50}$ (µM) for β-lactamase Inhibitory Activity $IC_{50}$ β-lactamase (µM)

| | (A) | | | | (C) | | | (D) | | |
| | | | | AmpC | | AmpC | | | | |
| | TEM-1 | SHV-1 | CTX-M-15 | KPC-2 | (P99) | CMY-37 | (PAE) | OXA-1 | OXA-11 | OXA-15 | OXA-48 |
|---|---|---|---|---|---|---|---|---|---|---|---|
| Example 1 | 0.0032 | 0.0013 | 0.0054 | 0.0078 | 0.0041 | 0.0099 | 0.037 | 0.080 | 0.0041 | 0.00065 | 0.00051 |
| Example 2 | 0.0017 | 0.00074 | 0.00076 | 0.0039 | 0.0032 | 0.017 | 0.11 | 0.0061 | 0.0068 | 0.00084 | 0.0035 |
| Example 3 | 0.0030 | 0.0046 | 0.0020 | 0.033 | 0.0074 | 0.025 | 0.22 | 0.017 | 0.048 | 0.0016 | 0.0057 |
| Example 4 | 0.014 | 0.020 | 0.0030 | 0.068 | 0.035 | 0.012 | 0.40 | 0.061 | 0.16 | 0.0073 | 0.027 |
| Example 5 | 0.11 | 0.064 | 0.13 | 1.8 | 11 | 12 | 12 | 0.37 | 0.43 | 0.0080 | 0.18 |
| Example 6 | 0.28 | 0.34 | 0.51 | 5.1 | 6.4 | 6.8 | 38 | 1.2 | 1.6 | 0.068 | 0.84 |

TABLE 2-continued

Bacterial species used in MIC determination

| Strain | | Resistance mechanism |
|---|---|---|
| C. murliniae | 210102 | VIM-4 |
| E. coli | UFR52 | TEM-1, SHV-12, IMP-8 |
| P. aeruginosa | CIP107051 | TEM-24 |
| P. aeruginosa | CIP105250 | OXA-15 |
| P. aeruginosa | UFR35 | OXA-23 |
| P. aeruginosa | UFR90 | Derepressed ampC, OprD- |
| P. aeruginosa | UFR92 | Derepressed ampC, OprD- |
| P. aeruginosa | UFR93 | Derepressed ampC, OprD-, MexAB+, MexXY+ |
| P. aeruginosa | UFR47 | VIM-1 |
| P. aeruginosa | UFR48 | VIM-2 |
| P. aeruginosa | UFR59 | IMP-29 |

TABLE 3

MIC of compounds

MIC compounds of the invention alone (μg/mL)

| Strains | Example 1 | Example 2 | Example 3 | Example 4 | Example 5 | Example 6 | Example 7 |
|---|---|---|---|---|---|---|---|
| 260508 | 0.063 | ≤0.016 | | | 8 | | |
| UFR61O | 0.031 | 0.031 | | | 0.5 | | |
| BAA-1898 | >32 | 16 | >32 | >32 | 16 | >32 | >32 |
| 160143 | >32 | 8 | | | 32 | | |
| UFR68 | >32 | 16 | | | 32 | | |
| P99 | 0.031 | ≤0.016 | 0.063 | >32 | ≤0.016 | 0.125 | 0.031 |
| UFR85 | >32 | 16 | | | 8 | | |
| UFR70 | 16 | 4 | | | 8 | | |
| UFR77 | >32 | 32 | | | >32 | | |
| UFR74 | >32 | 16 | | | 16 | | |
| UFR18 | 0.031 | ≤0.016 | | | ≤0.016 | | |
| 131119 | 32 | ≤0.016 | 0.5 | >32 | 0.063 | >32 | 0.031 |
| UFR21 | >32 | 16 | | | 32 | | |
| UFR24 | >32 | >32 | | | >32 | | |
| 6299 | >32 | >32 | >32 | >32 | >32 | >32 | >32 |
| RGN238 | >32 | 8 | >32 | >32 | 16 | >32 | 16 |
| 200047 | >32 | 16 | | | 16 | | |
| 190317 | 0.031 | ≤0.016 | 0.25 | >32 | ≤0.016 | 0.125 | 0.063 |
| UFR32 | 0.031 | ≤0.016 | | | 0.063 | | |
| UFR38 | ≤0.016 | 32 | | | ≤0.016 | | |
| 210102 | >32 | 4 | | | 4 | | |
| UFR52 | 2 | 4 | | | 4 | | |
| CIP107051 | 2 | 2 | 16 | >32 | 2 | 16 | 8 |
| CIP105250 | >32 | 8 | >32 | >32 | 4 | 32 | 32 |
| UFR35 | 1 | 2 | 2 | | 0.25 | | |
| UFR90 | 0.5 | 1 | 1 | | 0.25 | | |
| UFR92 | 2 | 2 | 8 | | 1 | | |
| UFR93 | 8 | 4 | 16 | | 4 | | |
| UFR47 | 2 | 2 | 4 | | 1 | | |
| UFR48 | 4 | 2 | 8 | | 2 | | |
| UFR59 | 8 | 8 | 16 | | 2 | | |

TABLE 4

MIC of Ceftazidime/compound combinations combination of CAZ and compounds of the invention et 4 μg/mL: MIC (μg/mL)

| Strains | CAZ | Example 1 | Example 2 | Example 3 | Example 4 | Example 5 | Example 6 | Example 7 |
|---|---|---|---|---|---|---|---|---|
| 260508 | 128 | ≤0.125 | <0.25 | | | <0.25 | | |
| UFR610 | 128 | <0.25 | <0.25 | | | <0.25 | | |
| BAA-1898 | 256 | 0.5 | ≤0.125 | 1 | 64 | ≤0.125 | 4 | ≤0.125 |
| 160143 | 128 | 1 | ≤0.125 | | | <0.25 | | |
| UFR68 | >128 | 1 | ≤0.125 | | | ≤0.25 | | |
| P99 | 128 | <0.25 | <0.25 | <0.125 | 64 | <0.25 | ≤0.125 | <0.125 |
| UFR85 | 128 | 2 | ≤0.125 | | | <0.25 | | |
| UFR70 | >128 | 1 | <0.25 | | | <0.25 | | |
| UFR77 | 64 | 2 | 2 | | | <0.25 | | |
| UFR74 | 64 | 4 | ≤0.125 | | | <0.25 | | |
| UFR18 | >128 | <0.25 | <0.25 | | | <0.25 | | |
| 131119 | 0.5 | <0.25 | <0.25 | | | <0.25 | | |
| UFR21 | 128 | 0.5 | ≤0.125 | | | <0.25 | | |
| UFR24 | >128 | 4 | 0.25 | | | <0.25 | | |
| 6299 | 256 | 0.5 | 4 | 1 | 128 | 8 | 4 | 2 |
| RGN238 | 0.5 | ≤0.125 | ≤0.125 | | | <0.25 | | |
| 200047 | 128 | 0.5 | ≤0.125 | | | <0.25 | | |
| 190317 | 128 | <0.25 | <0.25 | <0.125 | 4 | <0.25 | <0.125 | <0.125 |
| UFR32 | >128 | <0.25 | <0.25 | | | <0.25 | | |
| UFR38 | >128 | <0.25 | <0.25 | | | <0.25 | | |
| 210102 | >128 | 0.5 | ≤0.125 | | | <0.25 | | |
| UFR52 | >128 | <0.25 | <0.25 | | | <0.25 | | |
| CIP107051 | 256 | <0.25 | <0.25 | ≤0.25 | 64 | <0.25 | 32 | 1 |
| CIP105250 | 256 | ≤0.125 | ≤0.125 | 8 | 128 | <0.25 | 64 | 32 |
| UFR35 | 2 | <0.25 | <0.25 | <0.25 | | <0.25 | | |
| UFR90 | 64 | <0.25 | <0.25 | <0.25 | | <0.25 | | |
| UFR92 | 32 | <0.25 | <0.25 | ≤0.25 | | <0.25 | | |
| UFR93 | >128 | <0.25 | <0.25 | 0.5 | | <0.25 | | |

TABLE 4-continued

MIC of Ceftazidime/compound combinations combination of CAZ and compounds of the invention et 4 μg/mL:
MIC (μg/mL)

| Strains | CAZ | Example 1 | Example 2 | Example 3 | Example 4 | Example 5 | Example 6 | Example 7 |
|---|---|---|---|---|---|---|---|---|
| UFR47 | >128 | <0.25 | <0.25 | <0.25 | | | <0.25 | |
| UFR48 | 256 | <0.25 | <0.25 | 16 | | | <0.25 | |
| UFR59 | 128 | <0.25 | <0.25 | 2 | | | <0.25 | |

The invention claimed is:

1. A compound of formula (I)

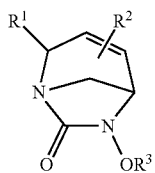

(I)

wherein:

R$^1$ is selected from the group consisting of a carbon-linked 4- or 5- or 6-member monocyclic heterocycle comprising a nitrogen heteroatom and optionally one or two or three further heteroatoms selected from the group consisting of N, O, S, S(O)$_2$ and that is saturated or partially unsaturated or totally unsaturated or aromatic and optionally substituted by one or more T$^1$, —CN, —(CH$_2$)$_m$—OQ$^1$, —(CH$_2$)$_m$—OC(O)Q$^1$, —C(O)OQ$^1$, —(CH$_2$)$_m$—OC(O)OQ$^1$, —(CH$_2$)$_m$—OC(O)NQ$^1$Q$^2$, —C(O)NHQ$^1$, —C(O)NHOQ$^1$, —(CH$_2$)$_m$—NHS(O)$_2$NQ$^1$Q$^2$, —C(O)NH—NHQ$^1$, —C(O)O—NHQ$^1$, —(CH$_2$)$_m$—NHC(O)Q$^1$, —(CH$_2$)$_m$—HS(O)$_2$Q$^1$, —(CH$_2$)$_m$—NHC(O)OQ$^1$, —(CH$_2$)$_m$—NHC(O)NQ$^1$Q$^2$, —(CH$_2$)$_m$—NHQ$^3$, —(CH$_2$)$_m$—NH—C(NHQ$^3$)=NQ$^4$, —(CH$_2$)$_m$—NH—CH=NQ$^3$, and —C(NHQ$^3$)=NQ$^4$;

R$^2$ is a 4- to 10-member monocyclic or bicyclic heterocycle comprising a nitrogen heteroatom and optionally one or two or three further heteroatoms selected from the group consisting of N, O, S, S(O), and S(O)$_2$ and that is saturated or partially unsaturated or totally unsaturated or aromatic and optionally substituted by one or more T$^2$;

R$^3$ is —SO$_3$H, —CFHCOOH, or —CF$_2$COOH;

T$^1$, identical or different, is independently selected from the group consisting of F, C$_1$-C$_3$ alkyl that is optionally substituted by one or more T$^3$, C$_1$-C$_3$ fluoroalkyl that is optionally substituted by one or more T$^3$, O—C$_1$-C$_3$ fluoroalkyl that is optionally substituted by one or more T$^3$, —(CH$_2$)$_n$-(4- or 5- or 6-member monocyclic heterocycle comprising a nitrogen heteroatom and optionally one or two or three further heteroatoms selected from the group consisting of N, O, S, S(O), and S(O)$_2$ and that is saturated or partially unsaturated or totally unsaturated or aromatic) that is optionally substituted by one or more T$^3$, —(CH$_2$)$_n$OQ$^1$, —(CH$_2$)$_n$—C(O)ONHQ$^1$, —(CH$_2$)$_n$—CN, —(CH$_2$)$_n$—OC(O)Q$^1$, —(CH$_2$)$_n$—C(O)OQ$^1$, —(CH$_2$)—NHS(O)$_2$NQ$^1$Q$^2$, —(CH$_2$)$_n$—OC(O)OQ$^1$, —(CH$_2$)$_n$—OC(O)NHQ$^1$, —(CH$_2$)$_n$—C(O)NHQ$^1$, —(CH$_2$)$_n$—C(O)NHOQ$^1$, —(CH$_2$)$_n$—C(O)NH—NHQ$^1$, —(CH$_2$)$_n$—NHC(O)Q$^1$, —(CH$_2$)$_n$—NHS(O)$_2$Q$^1$, —(CH$_2$)$_n$—NHC(O)OQ$^1$, —(CH$_2$)$_n$—NHC(O)NQ$^1$Q$^2$, —(CH$_2$)$_n$—NHQ$^1$, —(CH$_2$)$_n$—NH—C(NHQ$^3$)=NQ$^4$, —(CH$_2$)$_n$—NH—CH=NQ$^3$, and (CH$_2$)$_n$—C(NHQ$^3$)=NQ$^4$;

Q$^1$ and Q$^2$ is one of the following:

Q$^1$ and Q$^2$, identical or different, are independently selected from the group consisting of H, C$_1$-C$_3$ alkyl that is optionally substituted by one or more T$^3$, —(CH$_2$)$_q$—NHQ$^3$, —(CH$_2$)$_q$—NH—C(NHQ$^3$)=NQ$^4$, (CH$_2$)$_q$—NH—CH=NQ$^3$, (CH$_2$)$_r$—C(NHQ$^3$)=NQ$^4$, —(CH$_2$)$_q$—OQ$^3$, —(CH$_2$)$_r$—CONHQ$^3$, —(CH$_2$)$_n$-(4- or 5- or 6-member monocyclic heterocycle comprising a nitrogen heteroatom and optionally one or two or three further heteroatoms selected from the group consisting of N, O, S, S(O), and S(O)$_2$ and that is saturated or partially unsaturated or totally unsaturated or aromatic) that is optionally substituted by one or more T$^3$; or Q$^1$ and Q$^2$ and the nitrogen atom to which they are bonded form together 4- or 5- or 6-member monocyclic heterocycle comprising a nitrogen heteroatom and optionally one or two or three further heteroatoms selected from the group consisting of N, O, S, S(O), and S(O)$_2$ and that is saturated or partially unsaturated and optionally substituted by one or more T$^3$;

Q$^3$ and Q$^4$, identical or different, are independently selected from the group consisting of H and C$_1$-C$_3$ alkyl;

T$^2$, identical or different, is independently selected from the group consisting of F, C$_1$-C$_3$ alkyl that is optionally substituted by one or more T$^3$, C$_1$-C$_3$ fluoroalkyl that is optionally substituted by one or more T$^3$, O—C$_1$-C$_3$ fluoroalkyl that is optionally substituted by one or more T$^3$, (X)$_p$—(CH$_2$)$_n$—C$_3$-C$_6$ cycloalkyl that is optionally substituted by one or more T$^3$, (X)$_p$—(CH$_2$)$_n$—C$_3$-C$_6$ cyclofluoroalkyl, —(X)$_p$—(CH$_2$)$_n$-(4- or 5- or 6-member monocyclic heterocycle comprising a nitrogen heteroatom and optionally one or two or three further heteroatoms selected from the group consisting of N, O, S, S(O), and S(O)$_2$ and that is saturated or partially unsaturated or totally unsaturated or aromatic) that is optionally substituted by one or more T$^3$, —(X)$_p$(CH$_2$)$_t$OQ$^5$, (X)$_p$—(CH$_2$)$_u$—CN, —(X)$_p$—(CH$_2$)$_t$—OC(O)Q$^5$, (X)$_p$—(CH$_2$)$_u$—C(O)OQ$^5$, (X)$_p$—(CH$_2$)$_t$—OC(O)OQ$^5$, (X)$_p$—(CH$_2$)$_t$—OC(O)NQ$^5$Q$^6$, (X)$_p$—(CH$_2$)$_u$—C(O)NQ$^5$Q$^6$, (X)$_p$—(CH$_2$)$_u$—C(O)ONQ$^5$Q$^6$, (X)$_p$—(CH$_2$)$_u$—C(O)NQ$^5$OQ$^6$, (X)$_p$—(CH$_2$)$_u$—C(O)NQ$^5$-NQ$^5$Q$^6$, (X)$_p$—(CH$_2$)$_t$—NQ$^5$C(O)Q$^6$, (X)$_p$—(CH$_2$)$_t$—NQ$^5$S(O)$_2$NQ$^5$Q$^6$, (X)$_p$—(CH$_2$)$_t$—NQ$^5$S(O)$_2$Q$^6$, (X)$_p$—(CH$_2$)$_t$—NQ$^5$C(O)OQ$^6$, (X)$_p$—(CH$_2$)$_t$—NQ$^5$C(O)NQ$^5$Q$^6$, (X)$_p$—(CH$_2$)$_t$—NQ$^5$Q$^6$, (X)$_p$—(CH$_2$)$_t$—NH—C(NHQ$^3$)=NQ$^4$, (X)$_p$—(CH$_2$)$_t$—NH—CH=NQ$^3$, (X)$_p$—(CH$_2$)$_u$—C(NHQ$^3$)=NQ$^4$;

$Q^5$ and $Q^6$ is one of the following:
- $Q^5$ and $Q^6$, identical or different, are independently selected from the group consisting of H, $C_1$-$C_3$ alkyl that is optionally substituted by one or more $T^3$, —$(CH_2)_q$—$NHQ^3$, —$(CH_2)_q$—NH—C($NHQ^3$)=$NQ^4$, —$(CH_2)_q$—NH—CH=$NQ^3$, —$(CH_2)_r$—C($NHQ^3$)=$NQ^4$, —$(CH_2)_q$—$OQ^3$, —$(CH_2)_r$—$CONHQ^3$, and —$(CH_2)_n$-(4- or 5- or 6-member monocyclic heterocycle comprising a nitrogen heteroatom and optionally one or two or three further heteroatoms selected from the group consisting of N, O, S, S(O), and $S(O)_2$ and that is saturated or partially saturated totally unsaturated or aromatic) that is optionally substituted by one or more $T^3$; or
- $Q^5$ and $Q^6$ and the nitrogen atom to which they are bonded form together a saturated or partially unsaturated 4- to 6-member monocyclic heterocycle comprising a nitrogen heteroatom and optionally one or two or three further heteroatoms selected from the group consisting of N, O, S, S(O), and $S(O)_2$ and that is optionally substituted by one or more $T^3$;

$T^3$, identical or different, is independently selected from the group consisting of —OH, —$NH_2$, and —$CONH_2$;

m, identical or different, is independently selected from the group consisting of 1 and 2;

n, identical or different, is independently selected from the group consisting of 0, 1, 2, and 3;

t, identical or different, is independently selected from the group consisting of 0, 1, 2, and 3 if p is 0, but if p is 1 then t, identical or different, is independently selected from the group consisting of 2 and 3;

u, identical or different, is independently selected from the group consisting of 0, 1, 2, and 3 if p is 0, but if p is 1 then u, identical or different is independently selected from the group consisting of 1, 2, and 3;

q, identical or different, is independently selected from the group consisting of 2 and 3;

r, identical or different, is independently selected from the group consisting of 1, 2, and 3;

p, identical or different, is independently selected from the group consisting of 0 and 1;

X, identical or different, is independently selected from the group consisting of O, S, S(O), $S(O)_2$ and N($Q^3$);

wherein any carbon atom present within any of the foregoing alkyls, cycloalkyls, fluoralkyls, cyclofluoroalkyls, heterocycles may be oxidized to form a C(O) group;

wherein any sulphur atom present within any of the foregoing heterocycles may be oxidized to form a S(O) group or a $S(O)_2$ group;

wherein any nitrogen atom present within a heterocycle or a tertiary amine group may be further quaternized by a methyl group; or a pharmaceutically acceptable salt, a corresponding zwitterion, an optical isomer, a racemate, a diastereoisomer, an enantiomers, or a tautomer of formula (I).

2. The compound according to claim 1, wherein $R^1$ is one of the following:
- $R^1$ is selected from the group consisting of a carbon-linked 4- or 5- or 6-member monocyclic heterocycle comprising a nitrogen heteroatom and optionally one or two or three further heteroatoms selected from the group consisting of N, O, S, S(O), and $S(O)_2$ and that is saturated or partially unsaturated, or totally unsaturated or aromatic and is optionally substituted by one or more $T^1$, —CN, —$(CH_2)_m$—$OQ^1$, —$(CH_2)_m$—OC(O)$Q^1$, —C(O)$OQ^1$, —$(CH_2)_m$—OC(O)$OQ^1$, —$(CH_2)_m$—OC(O)N$Q^1Q^2$, —C(O)NH$Q^1$, —$(CH_2)_m$NHS$(O)_2$N$Q^1Q^2$, —C(O)NHO$Q^1$, —C(O)NH—NH$Q^1$, —C(O)O—NH$Q^1$, —$(CH_2)_m$—NHC(O)$Q^1$, —$(CH_2)_m$—NHS$(O)_2Q^1$, —$(CH_2)_m$—NHC(O)O$Q^1$, —$(CH_2)_m$—NHC(O)N$Q^1Q^2$; or
- $R^1$ is selected from the group consisting of —$(CH_2)_m$NH$Q^3$, —$(CH_2)_m$—NH—C(NH$Q^3$)=N$Q^4$, $(CH_2)_m$—NH—CH=N$Q^3$, and —C(NH$Q^3$)=N$Q^4$.

3. The compound according to claim 1, wherein $R^1$ is one of the following:
- $R^1$ is selected from the group consisting of a carbon-linked 4- or 5- or 6-member heterocycle comprising a nitrogen heteroatom and optionally one or two or three further heteroatoms selected from the group consisting of N, O, S, S(O), and $S(O)_2$ and that is saturated or partially unsaturated or totally unsaturated or aromatic and optionally substituted by one or more $T^1$, —CN, —C(O)NH$Q^1$, —C(O)NHO$Q^1$, —C(O)NH—NH$Q^1$ and —$(CH_2)_m$O$Q^1$; or
- $R^1$ is selected from the group consisting of —$(CH_2)_m$NH$Q^3$, —$(CH_2)_m$—NH—C(NH$Q^3$)=N$Q^4$, wherein m is 1, and wherein $Q^3$ and $Q^4$ are H.

4. The compound according to claim 1, wherein $R^1$ is selected from the group consisting of —CN, —C(O)O$Q^1$, —C(O)NH$Q^1$, —C(O)NHO$Q^1$, and —C(O)NH—NH$Q^1$.

5. The compound according to claim 1, wherein $R^1$ is selected from the group consisting of —$(CH_2)_m$—O$Q^1$, —$(CH_2)_m$—NHC(O)$Q^1$, —$(CH_2)_m$—NHC(O)O$Q^1$, and —$(CH_2)_m$—NHC(O)N$Q^1Q^2$.

6. The compound according to claim 1, wherein $R^1$ is a carbon-linked 4- or 5- or 6-member monocyclic heterocycle comprising a nitrogen heteroatom and that is saturated or partially unsaturated or totally unsaturated or aromatic and optionally substituted by one or more $T^1$ and further comprises one or two or three additional heteroatoms wherein each additional heteroatom is selected from the group consisting of N, O, S, S(O), and $S(O)_2$.

7. The compound according to claim 1, wherein $R^1$ is selected from the group consisting of —$(CH_2)_m$NH$Q^3$, —$(CH_2)_m$—NH—C(NH$Q^3$)=N$Q^4$, —CN, —C(O)NH$Q^1$, —C(O)NHO$Q^1$, —C(O)NH—NH$Q^1$, —$(CH_2)_m$—O$Q^1$, —$(CH_2)_m$—NHC(O)$Q^1$, —$(CH_2)_m$—NHC(O)N$Q^1Q^2$, —$(CH_2)_m$—NHC(O)O$Q^1$, and a carbon-linked 4- or 5- or 6-member monocyclic heterocycle comprising a nitrogen heteroatom and that is saturated or partially unsaturated or totally unsaturated or aromatic and optionally substituted by one or more $T^1$ and further comprises one or two or three additional heteroatoms wherein each heteroatom is selected from the group consisting of N, O, S, S(O) and $S(O)_2$; and wherein $Q^3$ and $Q^4$ are H.

8. The compound according to claim 1, wherein $R^2$ is selected from the group consisting of a 4- or 5 or 6-member monocyclic heterocycle comprising a nitrogen heteroatom and that is saturated or partially unsaturated or totally unsaturated or aromatic and optional substituted by one or more $T^2$ and further comprises one or two or three additional heteroatoms wherein each additional heteroatom is selected from the group consisting of N, O, S, S(O), and $S(O)_2$.

9. A compound according to claim 1, wherein:
$R^1$ is one of the following:
- $R^1$ is —$(CH_2)_m$NH$Q^3$ or —$(CH_2)_m$—NH—C(NH$Q^3$)=N$Q^4$, wherein m is 1; or
- $R^1$ is selected from the group consisting of —CN; C(O)NH$Q^1$, —C(O)NHO$Q^1$, and —C(O)NH—NH$Q^1$;

R[1] is selected from the group consisting of —(CH$_2$)$_m$—OQ$^1$, —(CH$_2$)$_m$—NHC(O)Q$^1$, —(CH$_2$)$_m$—NHC(O)OQ$^1$, and —(CH$_2$)$_m$—NHC(O)NQ$^1$Q$^2$;

R[1] is a carbon-linked 4- or 5- or 6-member monocyclic heterocycle comprising at least one nitrogen atom that is saturated or partially unsaturated or totally unsaturated or aromatic and optionally substituted by one or more T$^1$ and further comprises one or two or three additional heteroatoms wherein each additional heteroatom is selected from the group consisting of N, O, S, S(O), and S(O)$_2$ and is monocyclic;

R[1] is selected from the group consisting of —(CH$_2$)$_m$NHQ$^3$, —(CH$_2$)$_m$—NH—C(NHQ$^3$)=NQ$^4$, —(CH$_2$)$_m$—OQ$^1$, —(CH$_2$)$_m$—NHC(O)Q$^1$, —(CH$_2$)$_m$—NHC(O)OQ$^1$, —(CH$_2$)$_m$—NHC(O)NQ$^1$Q$^2$, a carbon-linked 4- or 5- or 6-member monocyclic heterocycle comprising at least one nitrogen atom that is saturated or partially unsaturated or totally unsaturated or aromatic and optionally substituted by one or more T$^1$ and further comprises one or two or three additional heteroatoms wherein each additional heteroatom is selected from the group consisting of N, O, S, S(O), and S(O)$_2$; and Q$^1$ and Q$^2$, identical or different, are independently selected from the group consisting of H, methyl, —CH$_2$—CH$_2$—NH$_2$, —CH$_2$—CH$_2$—NH—CNH$_2$=NH, —CH$_2$—CH$_2$—NH—CH=NH, —CH$_2$—C(NH$_2$)=NH, CH$_2$—CH$_2$—OH, —CH$_2$—CONH$_2$, and —(CH$_2$)$_n$-(4- or 5- or 6-member monocyclic heterocycle comprising a nitrogen heteroatom and optionally one or two or three heteroatoms selected from the group consisting of N, O, S, S(O), and S(O)$_2$ and that is saturated or partially unsaturated or totally unsaturated or aromatic and optionally substituted by one or more T$^3$); and Q$^3$ and Q$^4$ are H.

10. The compound according to claim 1, wherein:

R[1] is one of the following:

R[1] is selected from the group consisting of —(CH$_2$)$_m$NHQ$^3$ and —(CH$_2$)$_m$—NH—C(NHQ$^3$)=NQ$^4$, wherein m is 1;

R[1] is selected from the group consisting of —CN, C(O)NHQ$^1$, —C(O)NHOQ$^1$, and C(O)NH—NHQ$^1$;

R[1] is selected from the group consisting of —(CH$_2$)$_m$—OQ$^1$ and —(CH$_2$)$_m$—NHC(O)OQ$^1$;

R[1] is a carbon-linked 4- or 5- or 6-member monocyclic heterocycle comprising a nitrogen heteroatom and that is saturated or partially unsaturated or totally unsaturated or aromatic and optionally substituted by one or more T$^1$, and further comprises one or two or three additional heteroatoms wherein each additional heteroatom is selected from the group consisting of N, O, S, S(O), and S(O)$_2$; or R[1] is selected from the group consisting of —(CH$_2$)$_m$NHQ$^3$, —(CH$_2$)$_m$—NH—C(NHQ$^3$)=NQ$^4$, —(CH$_2$)$_m$—OQ$^1$, —(CH$_2$)$_m$—NHC(O)Q$^1$, —(CH$_2$)$_m$—NHC(O)OQ$^1$, —(CH$_2$)$_m$—NHC(O)NQ$^1$Q$^2$, a carbon-linked 4- or 5- or 6-member monocyclic heterocycle comprising a nitrogen heteroatom and that is saturated or partially unsaturated or totally unsaturated or aromatic and optionally substituted by one or more T$^1$, and further comprises one or two or three additional heteroatoms wherein each additional heteroatom is selected from the group consisting of N, O, S, S(O), and S(O)$_2$;

R[2] is a monocyclic or bicyclic 4- to 10-member heterocycle comprising a nitrogen heteroatom and optionally one or two or three further heteroatoms selected from the group consisting of N, O, S, S(O), and S(O)$_2$ and that is saturated or partially unsaturated or totally unsaturated or aromatic and optionally substituted by one or more T$^2$;

R[3] is SO$_3$H or CF$_2$COOH;

Q$^1$ and Q$^2$, identical or different, independently selected from the group consisting of H, methyl, —CH$_2$—CH$_2$—NH$_2$, —CH$_2$—CH$_2$—NH—CNH$_2$=NH, —CH$_2$—CH$_2$—NH—CH=NH, —CH$_2$—C(NH$_2$)=NH, CH$_2$—CH$_2$—OH, —CH$_2$—CONH$_2$, a —(CH$_2$)$_n$-(4- or 5- or 6-member monocyclic heterocycle comprising a nitrogen heteroatom and optionally one or two or three further heteroatoms selected from the group consisting of N, O, S, S(O), and S(O)$_2$ and that is saturated or partially unsaturated or totally unsaturated or aromatic and optionally substituted by one or more T$^3$; and Q$^3$ and Q$^4$ are H.

11. The compound according to claim 1 of formula (I*)

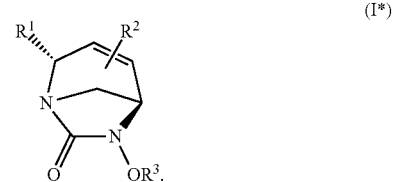

12. A compound selected from the group consisting of

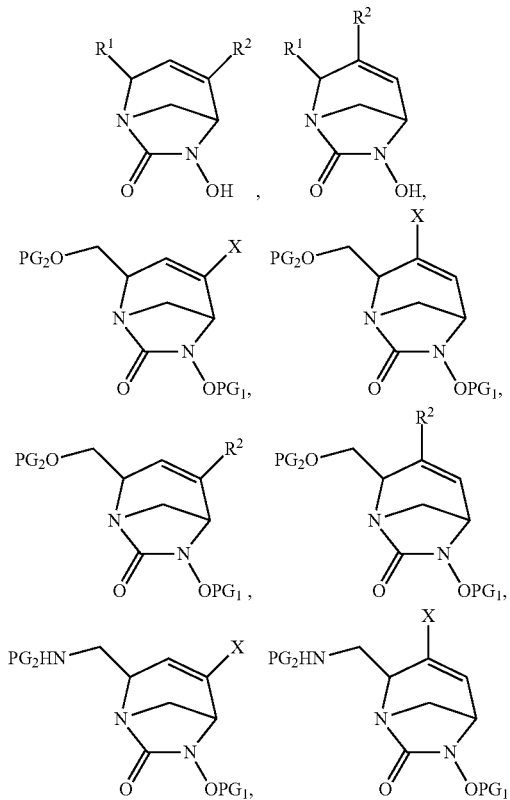

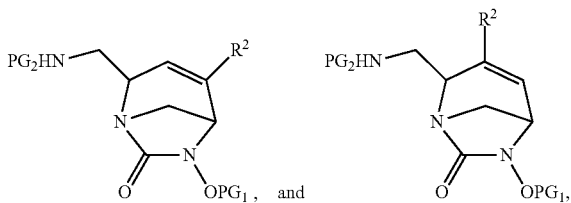
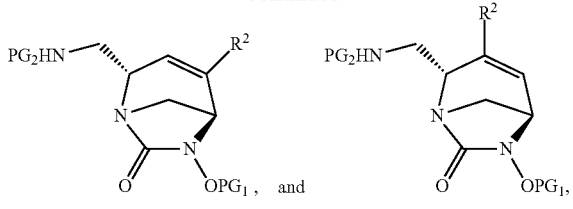

wherein:

X is selected from the group consisting of halogen, B(OR)₂, —OTf, and —SnR₃, wherein R is alkyl or the OR are linked together with the B to form a cycle; and PG₁ and PG₂, which are different, are protective groups.

13. A compound selected from the group consisting of

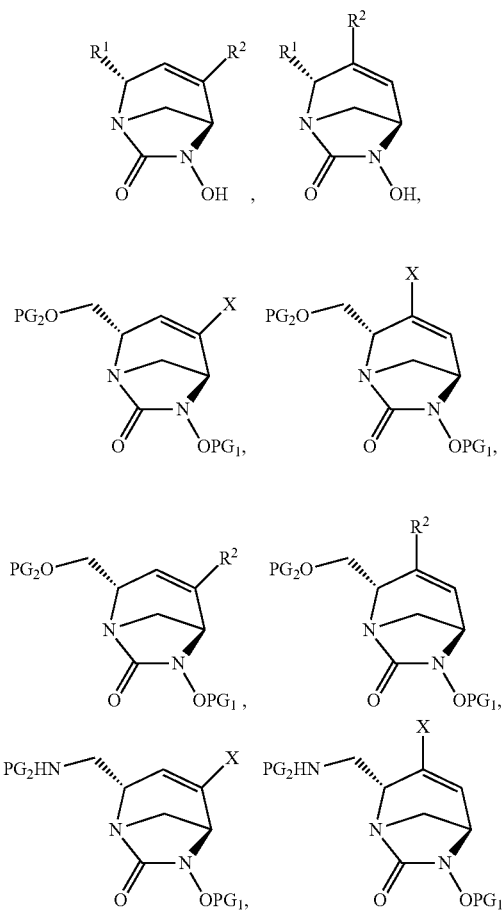

wherein:

X is selected from the group consisting of halogen, B(OR)₂, —OTf, and —SnR₃, wherein R is alkyl or the OR are linked together with the B to form a cycle comprising 5 members; and PG₁ and PG₂, which are different, are protective groups selected from the group consisting of allyl, benzyl, tertbutyldimethylsilyl (TBDMS), and tert-butoxycarbonyl (Boc).

14. A pharmaceutical composition comprising at least one compound according to claim 1 at an effective amount and a pharmaceutically acceptable excipient.

15. The pharmaceutical composition according to claim 14, further comprising an antibacterial agent selected from group consisting of aminoglycosides, beta-lactams, glycylcyclines, tetracyclines, quinolones, fluoroquinolones, glycopeptides, lipopeptides, macrolides, ketolides, lincosamides, streptogramins, oxazolidinones, polymyxins, and combinations thereof.

16. The pharmaceutical composition according to claim 15, wherein the antibacterial agent is selected from the group consisting of penicillin, cephalosporins, penems, carbapenems, monobactam, and combinations thereof.

17. A pharmaceutical composition comprising the compound according to claim 1 at an effective amount and ceftazidime.

18. A kit comprising:
a pharmaceutical composition comprising at least the compound according to claim 12 at an effective amount; and
at least another composition comprising one or more antibacterial agent(s).

19. A kit according comprising:
a pharmaceutical composition comprising at least the compound according to claim 1 at an effective amount; and
a pharmaceutical composition comprising ceftazidime.

20. A method for the treatment of bacterial infections in a patient, the method comprising the administration of a therapeutically effective amount of a compound according to claim 1.

21. The method according to claim 20, wherein the bacterial infection is caused by bacteria producing one or more beta-lactamases.

22. The method according to claim 20, wherein the bacterial infection is caused by gram-negative bacteria.

* * * * *